(12) United States Patent
Baasov et al.

(10) Patent No.: US 8,895,519 B2
(45) Date of Patent: Nov. 25, 2014

(54) AMINOGLYCOSIDES AND USES THEREOF IN TREATING GENETIC DISORDERS

(75) Inventors: Timor Baasov, Haifa (IL); Dana Atia-Glikin, Haifa (IL); Jeyakumar Kandasamy, Nesher (IL); Valery Belakhov, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/885,715

(22) PCT Filed: Nov. 17, 2011

(86) PCT No.: PCT/IL2011/000889
§ 371 (c)(1),
(2), (4) Date: May 16, 2013

(87) PCT Pub. No.: WO2012/066546
PCT Pub. Date: May 24, 2012

(65) Prior Publication Data
US 2013/0237489 A1     Sep. 12, 2013

Related U.S. Application Data

(60) Provisional application No. 61/414,956, filed on Nov. 18, 2010.

(51) Int. Cl.
| | | |
|---|---|---|
| A61K 31/70 | (2006.01) | |
| C07H 15/00 | (2006.01) | |
| C07H 17/00 | (2006.01) | |
| C07H 15/23 | (2006.01) | |
| C07H 5/06 | (2006.01) | |
| C07H 13/04 | (2006.01) | |

(52) U.S. Cl.
CPC .................. C07H 15/23 (2013.01); C07H 5/06 (2013.01); C07H 13/04 (2013.01)
USPC ............................ 514/38; 536/17.9; 536/18.1

(58) Field of Classification Search
None
See application file for complete search history.

(56) References Cited

FOREIGN PATENT DOCUMENTS

| WO | WO 2007/113841 | 10/2007 |
|---|---|---|
| WO | WO2007/113841 | * 10/2007 |
| WO | WO 2012/066546 | 5/2012 |

OTHER PUBLICATIONS

International Preliminary Report on Patentability Dated May 29, 2013 From the International Bureau of WIPO Re. Application No. PCT/IL2011/000889.
Brendel et al. "Readthrough of Nonsense Mutations in Rett Syndrome: Evaluation of Novel Aminoglycosides and Generation of a New Mouse Model", Journal of Molecular Medicine, 89(4): 389-398, Apr. 2011.
Brendel et al. "Suppression of Nonsense Mutations in Rett Syndrome by Aminoglycoside Antibiotics", Pediatric Research, 65(5): 520-523, 2009.
Kerem "Pharmacologic Therapy for Stop Mutations: How Much CFTR Activity Is Enough?", Current Opinion in Pulmonary Medicine, 10: 547-552, 2004.
Vecsler et al. "Ex Vivo Treatment With a Novel Synthetic Aminoglycoside NB54 in Primary Fibroblasts From Rett Syndrome Patients Suppresses MECP2 Nonsense Mutations", PLoS One, 6(6): e20733-1-e20722-8, Jun. 13, 2011.
Keeling et al. "Pharmacological Suppression of Premature Stop Mutations That Cause Genetic Diseases", Current Pharmacogenomics, 3(4): 259-269, 2005.
Keeling et al. "Suppression of Nonsense Mutations as a Therapeutic Approach to Treat Genetic Diseases", RNA. 2: 837-852, Nov./Dec. 2011.
Linde et al. "Introducing Sense Into Nonsense in Treatments of Human Genetic Diseases", Trends in Genetics, 24(11): 552-563, Oct. 18, 2008.
International Search Report and the Written Opinion Dated Mar. 27, 2012 from the International Searching Authority Re. Application No. PCT/IL2011/000889.
Azimov et al. "G418-Mediated Ribosmal Read-Through of a Nonsense Mutation Causing Autosomal Recessive Proximal Renal Tubular Acidosis", American Journal of Physiology, Renal Physiology, 295(3): F633-F641, Sep. 2008.

(Continued)

Primary Examiner — Traviss C McIntosh, III

(57) ABSTRACT

A new class of pseudo-trisaccharide aminoglycosides having an alkyl group at the 5" position, exhibiting efficient stop codon mutation readthrough activity, low cytotoxicity and high selectivity towards eukaryotic translation systems are provided. Also provided are pharmaceutical compositions containing the same, and uses thereof in the treatment of genetic disorders, as well as processes of preparing these aminoglycosides. The disclosed aminoglycosides can be represented by the general formula I:

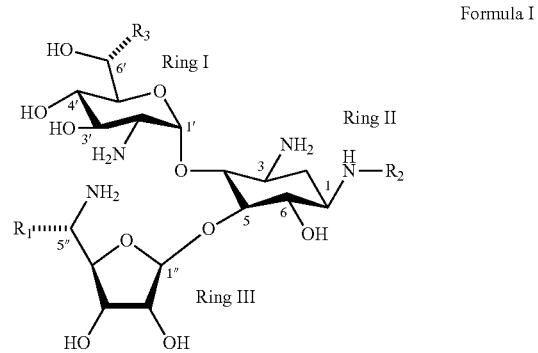

Formula I or a pharmaceutically acceptable salt thereof, wherein $R_1$ is selected from the group consisting of alkyl, cycloalkyl and aryl; and all other variables and features are as described in the specification.

42 Claims, 13 Drawing Sheets
(1 of 13 Drawing Sheet(s) Filed in Color)

(56) References Cited

OTHER PUBLICATIONS

Brendel et al. "Readthrough of Nonsense Mutations in Rett Syndrome: Evaluation of Novel Aminoglycosides and Generation of a New Mouse Model", Journal of Molecular Medicine, 89(4): 389-398, Published Online Dec. 1, 2010.
Goldmann et al. "Beneficial Read-Through of a USH1C Nonsense Mutation by Designed Aminoglycoside NB30 in the Retina", Investigative Ophthamology & Visual Science, 51(12): 6671-6680, Dec. 2010.
Hainrichson et al. "Designer Aminoglycosides: The Race to Develop Improved Antibiotics and Compounds for the Treatment of Human Genetic Diseases", Organic and Biomolecular Chemistry, 6(2): 227-239, Jan. 21, 2008.
Hobbie et al. "Engineering the rRNA Decoding Site of Eukaryotic Cytosolic Ribosomes in Bacteria", Nucleic Acids Research, 35(18): 6086-6093, Aug. 30, 2007.
Hobbie et al. "Genetic Analysis of Interactions With Eukayotic rRNA Identify the Mitoribosome as Target in Aminoglycoside Ototoxicity", Proc. Natl. Acad. Sci. USA, PNAS, 105(52): 20888-20893, Dec. 30, 2008.
Hobbie et al. "Mitochondrial Deafness Alleles Confer Misreading of the Genetic Code", Proc. Natl. Acad. Sci. USA, PNAS, 105(9): 3244-3249, Mar. 4, 2008.
Kandasamy et al. "Repairing Faulty Genes by Aminoglycosides: Identification of New Pharmacophore With Enhanced Suppression of Disease-Causing Nonsense Mutations", MedChemComm, 7 P., Jan. 14, 2011.
Kondo et al. "Differential Selectivity of Natural and Synthetic Aminoglycosides Towards the Eukaryotic and Prokaryotic Decoding A Sites", ChemBioChem, 8: 1700-1709, 2007.
Lopez-Novoa et al. "New Insights Into the Mechanism of Aminoglycoside Nephrotoxicity: An Integrative Point of View", Kidney International, Online Publication, 79(1): 33-45, Sep. 22, 2010.
Malik et al. "Aminoglycoside-Induced Mutation Suppression (Stop Codon Readthrough) as a Therapeutic Strategy for Duchenne Muscular Dystrophy", Therapeutic Advances in Neurological Disorders, 3(3): 379-389, Nov. 2010.
Nudelman "Combined Chemical-Enzymatic Assembly of Aminoglycoside Derivatives With N-1-AHB Side Chain", Advanced Synthesis & Catalysis, 350(11-12): 1682-1688, 2008.
Nudelman et al. "Development of Novel Aminoglycoside (NB54) With Reduced Toxicity and Enhanced Suppression of Disease-Causing Premature Stop Mutations", Journal of Medicinal Chemistry, 52(9): 2836-2845, 2009.
Nudelman et al. "Redesign of Aminoglycosides for Treatment of Human Genetic Diseases Caused by Premature Stop Mutations", Bioorganic & Medicinal Chemistry Letters, 16(24): 6310-6315, Dec. 15, 2006.
Nudelman et al. Repairing Faulty Genes by Aminoglycosides: Development of New Derivatives of Geneticin (G418) With Enhanced Suppression of Diseases-Causing Nonsense Mutations, Bioorganic & Medicinal Chemistry, XP055017979, 18(11): 3735-3746, Jun. 1, 2010. p. 3736, Compounds 1-2, 7-8, p. 3738, Compounds 11-16.
Pokrovskaya et al. "Aminoglycosides: Redesign Strategies for Improved Antibiotics and Compounds for Treatment of Human Genetic Diseases", Methods in Enzymology. 478(Chap.21): 437-462, 2010.
Rebibo-Sabbah et al. "In Vitro and Ex Vivo Suppressing by Aminoglycosides of PCDH15 Nonsense Mutations Underlying Type 1 Usher Syndrome", Human Genetics, 122: 373-381,2007.
Rowe et al. "Suppression CFTR Termination Codons and Rescue of CFTR Protein and Function by the Synthetic Aminoglycoside NB54", American Journal of Respiratory Cell and Molecular Biology, p. 1-43.
Venkataraman et al. "Reawakening Retrocyclins: Ancestral Human Defensins Active Against HIV-1", PLoS Biology, 7(4/e1000095): 0720-0729, Apr. 2009.
Warchol "Cellular Mechanisms of Aminoglycoside of Aminoglycoside Ototoxicity", Current Opinion in Otolaryngology & Head and Neck Surgery, 18(5): 454-458, Oct. 2010.

* cited by examiner

AMINOGLYCOSIDES AND USES THEREOF IN TREATING GENETIC DISORDERS

RELATED APPLICATIONS

This application is a National Phase of PCT Patent Application No. PCT/IL2011/000889 having International filing date of Nov. 17, 2011, which claims the benefit of priority under 35 USC §119(e) of U.S. Provisional Patent Application No. 61/414,956 filed on Nov. 18, 2010. The contents of the above applications are all incorporated by reference as if fully set forth herein in their entirety.

SEQUENCE LISTING STATEMENT

The ASCII file, entitled 56188SequenceListing.txt, created on May 13, 2013, comprising 5,337 bytes, submitted concurrently with the filing of this application is incorporated herein by reference.

FIELD AND BACKGROUND OF THE INVENTION

The present invention, in some embodiments thereof, relates to a new class of aminoglycosides and more particularly, but not exclusively, to novel aminoglycosides with improved efficacy towards treatment of genetic disorders.

Many human genetic disorders result from nonsense mutations, where one of the three stop codons (UAA, UAG or UGA) replaces an amino acid-coding codon, leading to premature termination of the translation and eventually to truncated inactive proteins. Currently, hundreds of such nonsense mutations are known, and several were shown to account for certain cases of fatal diseases, including cystic fibrosis (CF), Duchenne muscular dystrophy (DMD), ataxia-telangiectasia, Hurler syndrome, hemophilia A, hemophilia B, Tay-Sachs, and more. For many of those diseases there is presently no effective treatment, and although gene therapy seems like a potential possible solution for genetic disorders, there are still many critical difficulties to be solved before this technique could be used in humans.

Certain aminoglycosides have been shown to have therapeutic value in the treatment of several genetic diseases because of their ability to induce ribosomes to read-through stop codon mutations, generating full-length proteins from part of the mRNA molecules.

Typically, aminoglycosides are highly potent, broad-spectrum antibiotics commonly used for the treatment of life-threatening infections. It is accepted that the mechanism of action of aminoglycoside antibiotics, such as paromomycin, involves interaction with the prokaryotic ribosome, and more specifically involved binding to the decoding A-site of the 16S ribosomal RNA, which leads to protein translation inhibition and interference with the translational fidelity.

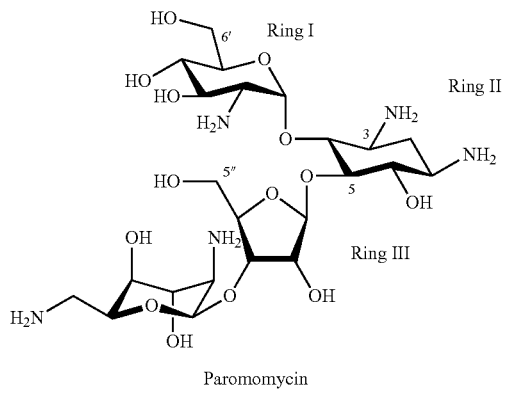

Paromomycin

Several achievements in bacterial ribosome structure determination, along with crystal and NMR structures of bacterial A-site oligonucleotide models, have provided useful information for understanding the decoding mechanism in prokaryote cells and understanding how aminoglycosides exert their deleterious misreading of the genetic code. These studies and others have given rise to the hypothesis that the affinity of the A-site for a non-cognate mRNA-tRNA complex is increased upon aminoglycosides binding, preventing the ribosome from efficiently discriminating between non-cognate and cognate complexes.

The enhancement of termination suppression by aminoglycosides in eukaryotes is thought to occur in a similar mechanism to the aminoglycosides' activity in prokaryotes of interfering with translational fidelity during protein synthesis, namely the binding of certain aminoglycosides to the ribosomal A-site probably induce conformational changes that stabilize near-cognate mRNA-tRNA complexes, instead of inserting the release factor. Aminoglycosides have been shown to suppress various stop codons with notably different efficiencies (UGA>UAG>UAA), and the suppression effectiveness is further dependent upon the identity of the fourth nucleotide immediately downstream from the stop codon (C>U>A≥grams) as well as the local sequence context around the stop codon.

The desired characteristics of an effective read-through drug would be oral administration and little or no effect on bacteria. Antimicrobial activity of read-through drug is undesirable as any unnecessary use of antibiotics, particularly with respect to the gastrointestinal (GI) biota, due to the adverse effects caused by upsetting the GI biota equilibrium and the emergence of resistance. In this respect, in addition to the abovementioned limitations, the majority of clinical aminoglycosides are greatly selective against bacterial ribosomes, and do not exert a significant effect on cytoplasmic ribosomes of human cells.

In an effort to circumvent the abovementioned limitations, the biopharmaceutical industry is seeking new stop mutations suppression drugs by screening large chemical libraries for nonsense read-through activity. Using this approach, a non-aminoglycoside compound, 3-[5-(2-fluorophenyl)-1,2,4-oxadiazol-3-yl]benzoic acid (PTC124), has been discovered. The facts that PTC124 is reported to have no antibacterial activity and no reported toxicity, suggest that its mechanism of action on the ribosome is different than that of the aminoglycosides.

The fact that aminoglycosides could suppress premature nonsense mutations in mammalian cells was first demonstrated by Burke and Mogg in 1985, who also noted the therapeutic potential of these drugs in the treatment of genetic disorders. The first genetic disease examined was cystic fibrosis (CF), the most prevalent autosomal recessive disorder in the Caucasian population, affecting 1 in 2,500 newborns. CF is caused by mutations in the cystic fibrosis transmembrane conductance regulator (CFTR) protein. Currently, more than 1,000 different CF-causing mutations in the CFTR gene were identified, and 5-10% of the mutations are premature stop codons. In Ashkenazi Jews, the W1282X mutation and other nonsense mutations account for 64% of all CFTR mutant alleles.

The first experiments of aminoglycoside-mediated suppression of CFTR stop mutations demonstrated that premature stop mutations found in the CFTR gene could be suppressed by members of the gentamicin family and geniticin (G-418), as measured by the appearance of full-length, functional CFTR in bronchial epithelial cell lines.

sides, including the use of antioxidants to reduce free radical levels, as well as the use of poly-L-aspartate and daptomycin, to reduce the ability of aminoglycosides to interact with phospholipids. The role of megalin (a multiligand endocytic receptor which is especially abundant in the kidney proximal tubules and the inner ear) in the uptake of aminoglycosides has recently been demonstrated. The administration of agonists that compete for aminoglycoside binding to megalin also resulted in a reduction in aminoglycoside uptake and toxicity. In addition, altering the administration schedule and/or the manner in which aminoglycosides are administered has been investigated as means to reduce toxicitys.

Despite extensive efforts to reduce aminoglycoside toxicity, few results have matured into standard clinical practices and procedures for the administration of aminoglycosides to suppress stop mutations, other than changes in the adminis-

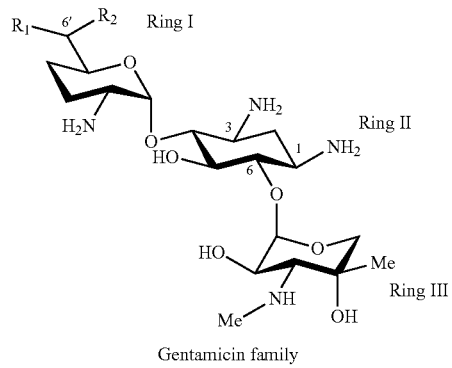

Gentamicin family

| | $R_1$ | $R_2$ |
|---|---|---|
| Gentamicin $C_1$ | $CH_3$ | $NHCH_3$ |
| Gentamicin $C_2$ | $CH_3$ | $NH_2$ |
| Gentamicin $C_{1A}$ | H | $NH_2$ |

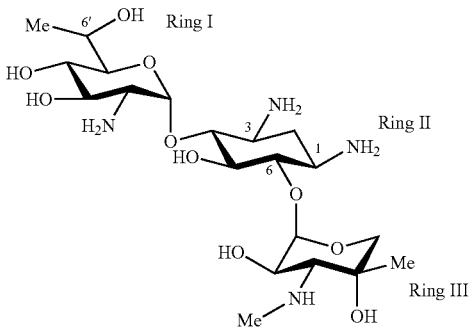

Geneticin (G-418)

Suppression experiments of intestinal tissues from CFTR−/− transgenic mice mutants carrying a human CFTR-G542X transgene showed that treatment with gentamicin, and to lesser extent tobramycin, have resulted in the appearance of human CFTR protein at the glands of treated mice. Most importantly, clinical studies using double-blind, placebo-controlled, crossover trails have shown that gentamicin can suppress stop mutations in affected patients, and that gentamicin treatment improved transmembrane conductance across the nasal mucosa in a group of 19 patients carrying CFTR stop mutations. Other genetic disorders for which the therapeutic potential of aminoglycosides was tested in in-vitro systems, cultured cell lines, or animal models include DMD, Hurler syndrome, nephrogenic diabetes insipidus, nephropathic cystinosis, retinitis pigmentosa, and ataxia-telangiectasia.

However, one of the major limitations in using aminoglycosides as pharmaceuticals is their high toxicity towards mammals, typically expressed in kidney (nephrotoxicity) and ear-associated (ototoxicity) illnesses. The origin of this toxicity is assumed to result from a combination of different factors and mechanisms such as interactions with phospholipids, inhibition of phospholipases and the formation of free radicals. Although considered selective to bacterial ribosomes, most aminoglycosides bind also to the eukaryotic A-site but with lower affinities than to the bacterial A-site. The inhibition of translation in mammalian cells is also one of the possible causes for the high toxicity of these agents. Another factor adding to their cytotoxicity is their binding to the mitochondrial ribosome at the 12S rRNA A-site, whose sequence is very close to the bacterial A-site.

Many studies have been attempted to understand and offer ways to alleviate the toxicity associated with aminoglycotration schedule. For example, the use of sub-toxic doses of gentamicin in the clinical trails probably caused the reduced read-through efficiency obtained in the in-vivo experiments compared to the in-vitro systems. The aminoglycoside geneticin® (G-418 sulfate) showed the best termination suppression activity in in-vitro translation-transcription systems, however, its use as a therapeutic agent is not possible since it is lethal even at very low concentrations. For example, the $LD_{50}$ of G-418 against human fibroblast cells is 0.04 mg/ml, compared to 2.5-5.0 mg/ml for gentamicin, neomycin and kanamycin.

The increased sensitivity of eukaryotic ribosomes to some aminoglycoside drugs, such as G-418 and gentamicin, is intriguing but up to date could not be rationally explained because of the lack of sufficient structural data on their interaction with eukaryotic ribosomes. Since G-418 is extremely toxic even at very low concentrations, presently gentamicin is the only aminoglycoside tested in various animal models and clinical trials. Although some studies have shown that due to their relatively lower toxicity in cultured cells, amikacin and paromomycin can represent alternatives to gentamicin for stop mutation suppression therapy, no clinical trials with these aminoglycosides have been reported yet.

To date, nearly all suppression experiments have been performed with clinical, commercially available aminoglycosides, however, only a limited number of aminoglycosides, including gentamicin, amikacin, and tobramycin, are in clinical use as antibiotics for internal administration in humans. Among these, tobramycin do not have stop mutations suppression activity, and gentamicin is the only aminoglycoside tested for stop mutations suppression activity in animal models and clinical trials. Recently, a set of neamine derivatives were shown to promote read-through of the SMN protein in fibroblasts derived from spinal muscular atrophy (SPA) patients; however, these compounds were originally designed as antibiotics and no conclusions were derived for further improvement of the read-through activity of these derivatives.

WO 2007/113841, by some of the present inventors, which is incorporated by reference as if fully set forth herein, teaches a class of paromomycin-derived aminoglycosides, which were designed specifically to exhibit high premature stop-codon mutations readthrough activity while exerting low cytotoxicity in mammalian cells and low antimicrobial activity, and can thus be used in the treatment of genetic diseases. This class of paromomycin-derived aminoglycosides was designed by introducing certain manipulations of a paromamine core, which lead to enhanced readthrough activity and reduced toxicity and antimicrobial activity. The manipulations were made on several positions of the paromamine core.

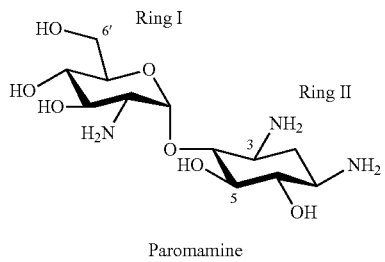

Paromamine

One such manipulation of the paromamine core which has been described in WO 2007/113841 is the determination of the beneficial role of a hydroxyl group at position 6' of the aminoglycoside core (see, for example, NB30 and NB54 below).

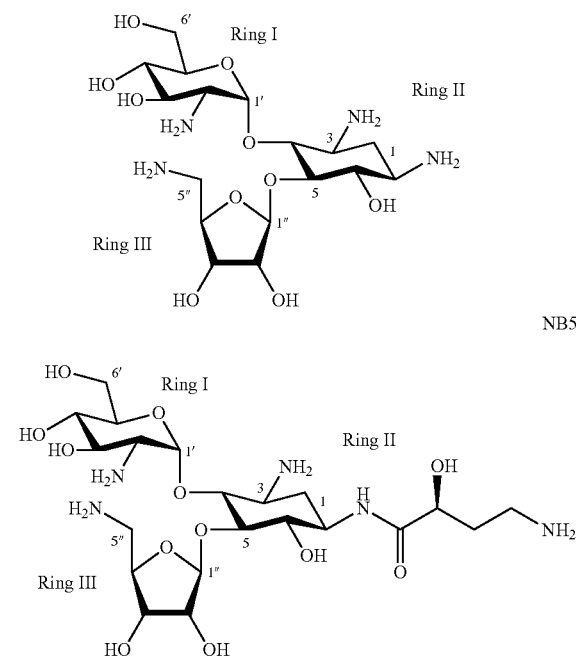

Another manipulation of the paromamine core which has been defined and demonstrated in WO 2007/113841 is the introduction of one or more monosaccharide moieties or an oligosaccharide moiety at position 3', 5 and/or 6 of the aminoglycoside core. This manipulation is reflected as "Ring III" in the exemplary compounds NB30 and NB54 shown hereinabove.

An additional manipulation of the paromamine core which has been defined and demonstrated in WO 2007/113841 is the introduction of an (S)-4-amino-2-hydroxybutyryl (AHB) moiety at position 1 of the paromamine core. This manipulation is reflected in exemplary compound NB54 shown hereinabove. It has been demonstrated that such an introduction of an AHB moiety provides for enhanced readthrough activity and reduced toxicity.

An additional manipulation of the paromamine core which has been described in WO 2007/113841 is the substitution of hydrogen at position 6' by an alkyl such as a methyl substituent. This manipulation has been exemplified in a derivative of compounds NB30 and NB54, referred to as NB74 and NB84 respectively.

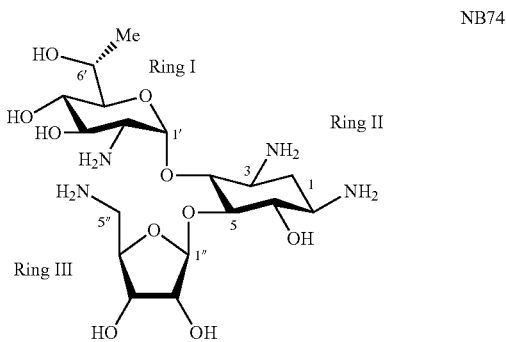

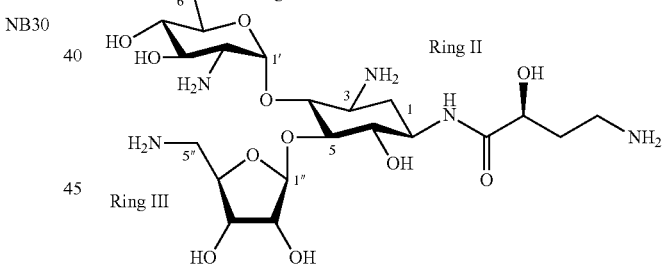

Additional background art includes Nudelman, I., et al., Bioorg Med Chem Lett, 2006. 16(24): p. 6310-5; Hobbie, S, N., et al., Nucleic Acids Res, 2007. 35(18): p. 6086-93; Kondo, J., et al., Chembiochem, 2007. 8(14): p. 1700-9; Rebibo-Sabbah, A., et al., Hum Genet, 2007. 122(3-4): p. 373-81; Azimov, R., et al., Am J Physiol Renal Physiol, 2008. 295(3): p. F633-41; Hainrichson, M., et al., Org Biomol Chem, 2008. 6(2): p. 227-39; Hobbie, S, N., et al., Proc Natl Acad Sci USA, 2008. 105(52): p. 20888-93; Hobbie, S, N., et al., Proc Natl Acad Sci USA, 2008. 105(9): p. 3244-9; Nudelman, I., et al., Adv. Synth. Catal., 2008. 350: p. 1682-1688; Nudelman, I., et al., J Med Chem, 2009. 52(9): p. 2836-45; Venkataraman, N., et al., PLoS Biol, 2009. 7(4): p. e95; Brendel, C., et al., J Mol Med (Berl), 2010. 89(4): p. 389-98; Goldmann, T., et al., Invest Ophthalmol Vis Sci, 2010. 51(12): p. 6671-80; Malik, V., et al., Ther Adv Neurol Disord, 2010. 3(6): p. 379-89; Nudelman, I., et al., Bioorg Med Chem, 2010. 18(11): p. 3735-46; Warchol, M. E., Curr Opin Otolaryngol Head Neck Surg, 2010. 18(5): p. 454-8; Lopez-Novoa, J. M., et al., Kidney Int, 2011. 79(1): p. 33-45; Rowe, S. M., et al., J Mol Med (Berl), 2011. 89(11): p. 1149-61; and Vecsler, M., et al., PLoS One, 2011. 6(6): p. e20733.

SUMMARY OF THE INVENTION

The present invention relates to a new class of pseudo-trisaccharide aminoglycosides, which can be beneficially used in the treatment of genetic diseases, such as cystic fibrosis, by exhibiting high premature stop-codon mutations read-through activity while exerting low toxicity in mammalian cells and low antimicrobial activity. The presently disclosed aminoglycosides are characterized by a core structure based on Rings I, II and III of paromomycin with the addition of an alkyl in position 5" on Ring III.

Thus, according to an aspect of some embodiments of the present invention there is provided a compound having the general formula I:

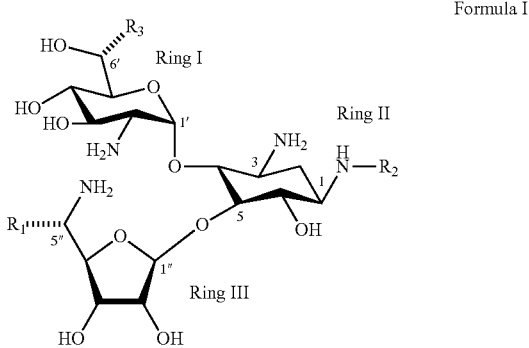

Formula I or a pharmaceutically acceptable salt thereof,
wherein:

$R_1$ is selected from the group consisting of alkyl, cycloalkyl and aryl;

$R_2$ is hydrogen or (S)-4-amino-2-hydroxybutyryl (AHB);

$R_3$ is selected from the group consisting of hydrogen, alkyl, cycloalkyl and aryl; and a stereo-configuration of each of position 6' and position 5" is independently an R configuration or an S configuration.

According to some embodiments of the invention, $R_1$ is alkyl.

According to some embodiments of the invention, the alkyl is methyl.

According to some embodiments of the invention, $R_2$ and $R_3$ are each hydrogen.

According to some embodiments of the invention, $R_2$ is AHB and $R_3$ is hydrogen.

According to some embodiments of the invention, $R_2$ is hydrogen and $R_3$ is alkyl.

According to some embodiments of the invention, $R_2$ is AHB and $R_3$ is alkyl. According to some embodiments of the invention, the alkyl is methyl.

According to some embodiments of the invention, the compounds presented herein are selected from the group consisting of the compounds NB118, NB119, NB122, NB123, NB124, NB125, NB127 and NB128.

According to some embodiments of the invention, the compounds presented herein are characterized by exhibiting a ratio of $IC_{50}$ translation inhibition in eukaryotes to $IC_{50}$ translation inhibition in prokaryotes lower than 15. According to some embodiments of the invention, the ratio is lower than 1.

According to some embodiments of the invention, the compounds presented herein are characterized by a MIC in Gram-negative bacteria higher than 200 μM and a MIC in Gram-positive bacteria higher than 20 μM.

According to another aspect of some embodiments of the present invention, there is provided a pharmaceutical composition which includes any one of the compounds presented herein and a pharmaceutically acceptable carrier.

According to some embodiments of the invention, the pharmaceutical composition is packaged in a packaging material and identified in print, in or on the packaging material, for use in the treatment of a genetic disorder.

According to another aspect of some embodiments of the present invention, there is provided a method for treating a genetic disorder, the method is effected by administering to a subject in need thereof a therapeutically effective amount of any one of the compounds presented herein.

According to some embodiments of the invention, the compounds presented herein are for use in the treatment of a genetic disorder.

According to another aspect of some embodiments of the present invention, there is provided a use of any one of the compounds presented herein in the manufacture of a medicament for treating a genetic disorder.

According to some embodiments of the invention, the genetic disorder is associated with a premature stop codon mutation and/or a protein truncation phenotype.

According to some embodiments of the invention, the genetic disorder is selected from the group consisting of cystic fibrosis (CF), Duchenne muscular dystrophy (DMD), ataxia-telangiectasia, Hurler syndrome, hemophilia A, hemophilia B, Usher syndrome and Tay-Sachs.

According to some embodiments of the invention, the genetic disorder is cystic fibrosis.

According to another aspect of some embodiments of the present invention, there is provided a process of preparing the compound presented herein, the process is effected by:

(a) providing a donor compound having the general Formula II:

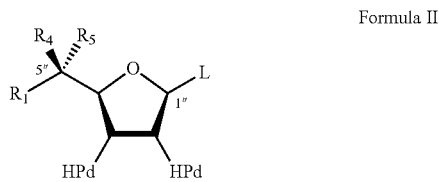

Formula II wherein:

$R_1$ is selected from the group consisting of alkyl, cycloalkyl and aryl;

$R_4$ is hydrogen or a donor amino-protecting group;

$R_5$ is a donor amino-protecting group if $R_4$ is hydrogen or hydrogen if $R_4$ is a donor amino-protecting group;

each of HPd is a donor hydroxyl-protecting group; and

L is a leaving group;

(b) coupling the donor compound with an acceptor compound having the general formula III

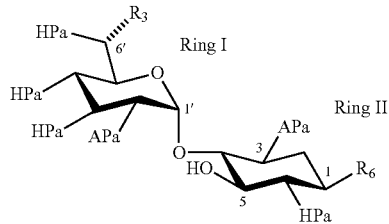

Formula III wherein:
the dashed line indicates an R configuration or an S configuration;
$R_3$ is selected from the group consisting of hydrogen, alkyl, cycloalkyl and aryl;
$R_6$ is an acceptor amino-protecting group or (S)-4-azido-2-O-acetyl-1-butyryl;
HPa is an acceptor hydroxyl-protecting group; and
APa is an acceptor amino-protecting group; and
(c) removing each of the amino-protecting group and the hydroxyl-protecting group, thereby obtaining the compound.

According to some embodiments of the invention, the leaving group is trichloroacetimidate.

According to some embodiments of the invention, the donor hydroxyl-protecting group is O-benzoyl and the donor amino-protecting group is azido.

According to some embodiments of the invention, the acceptor hydroxyl-protecting group is O-acetyl and the acceptor amino-protecting group is azido.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
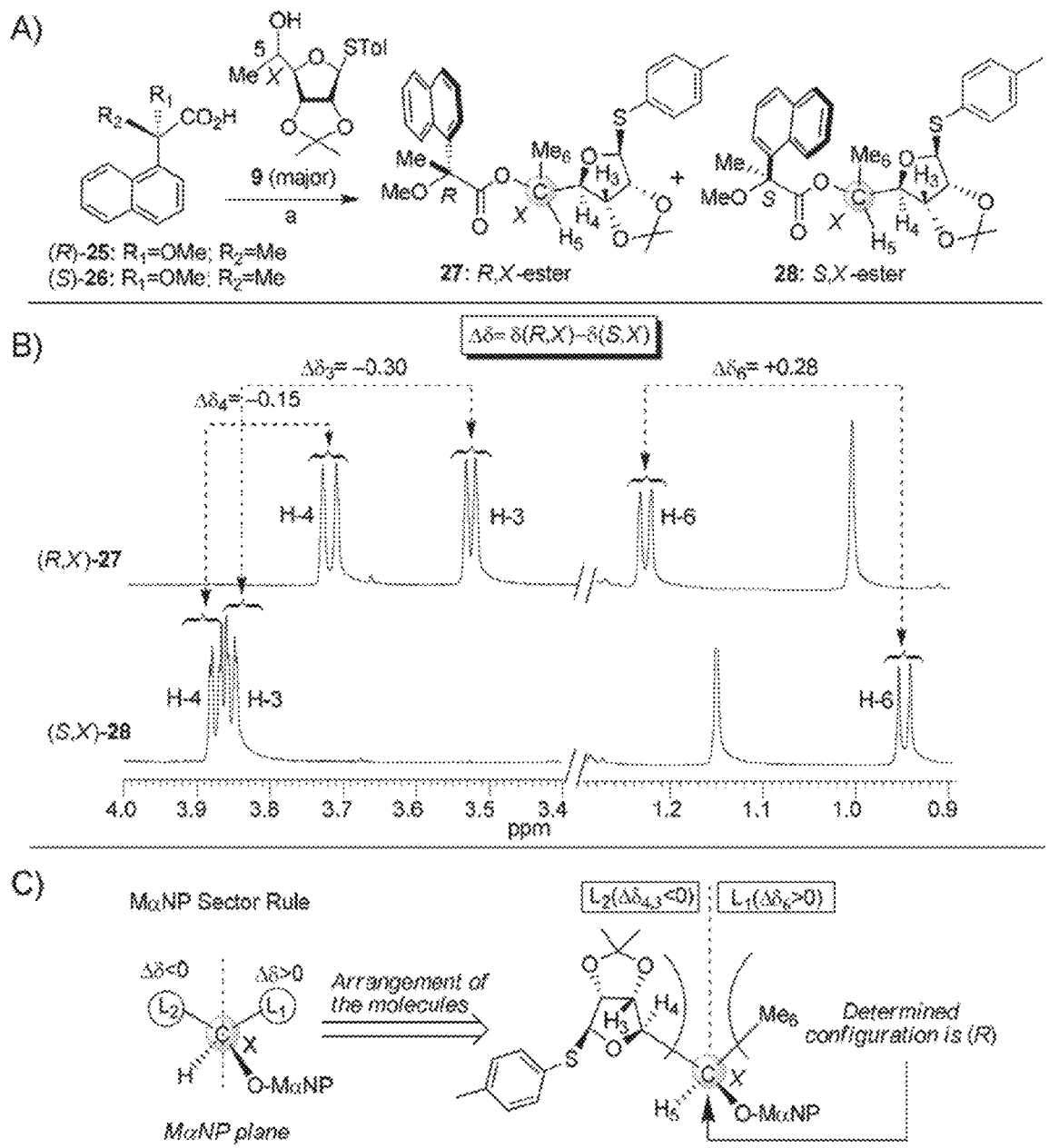
Figure 6:
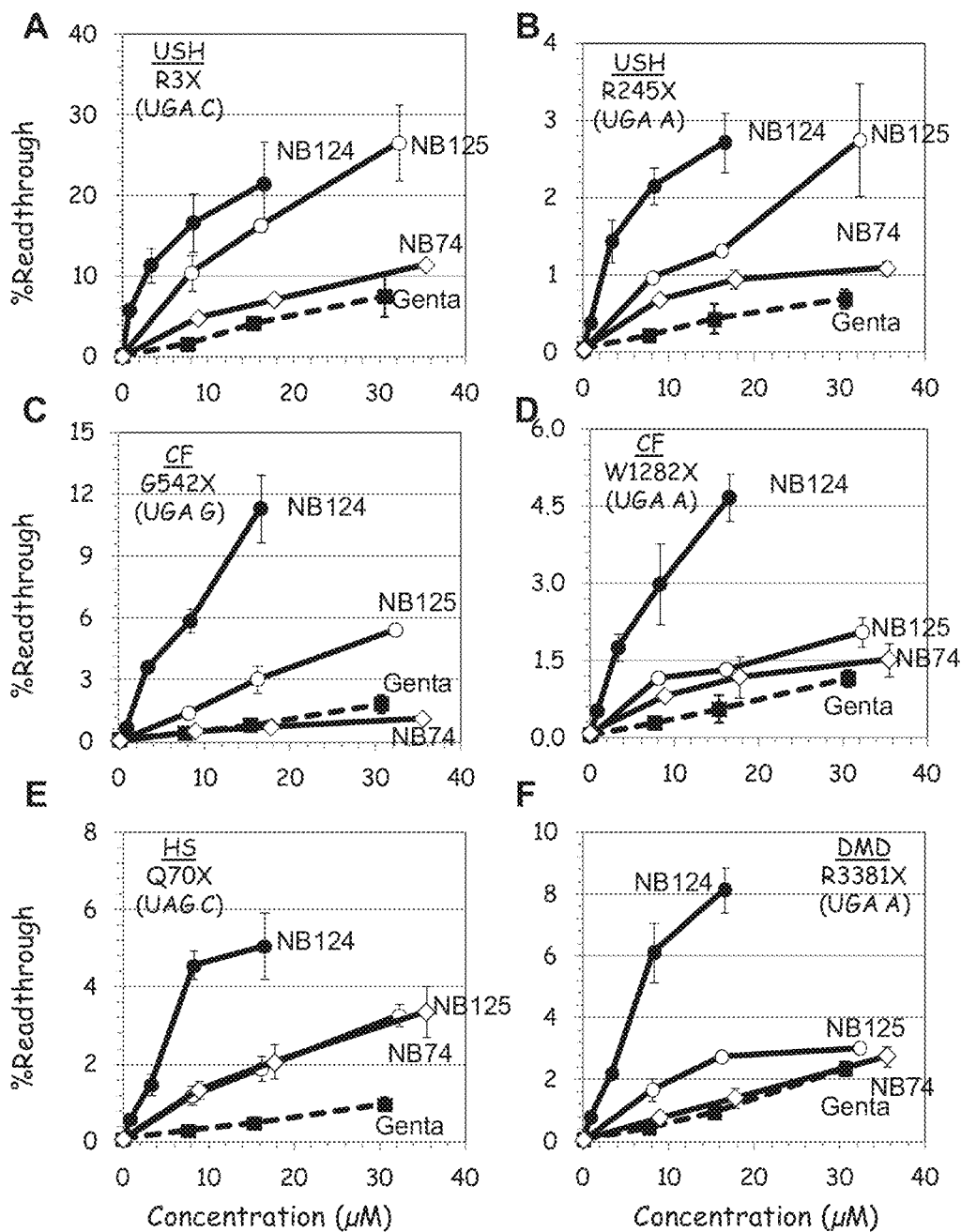
Figure 7:
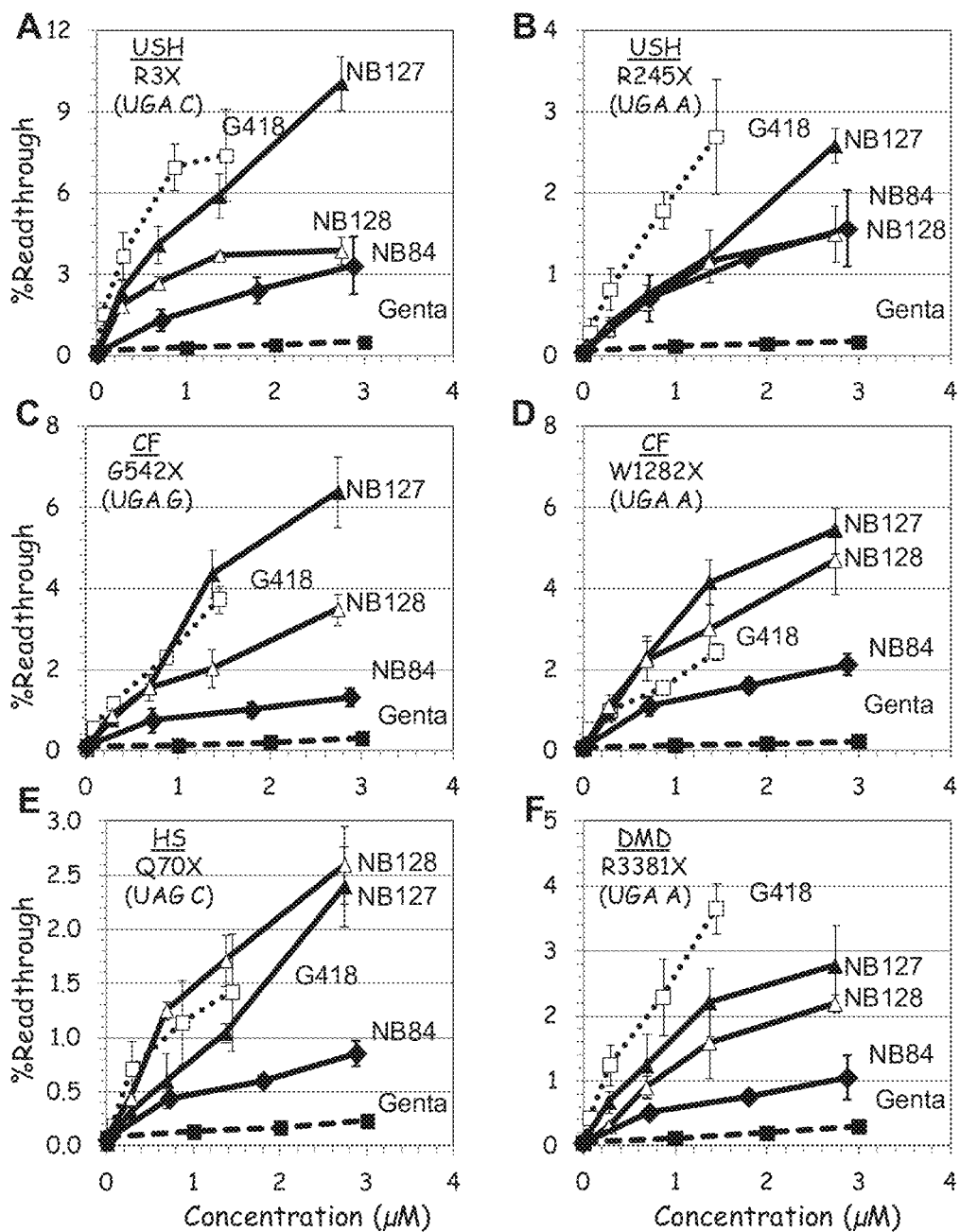
Figure 11:
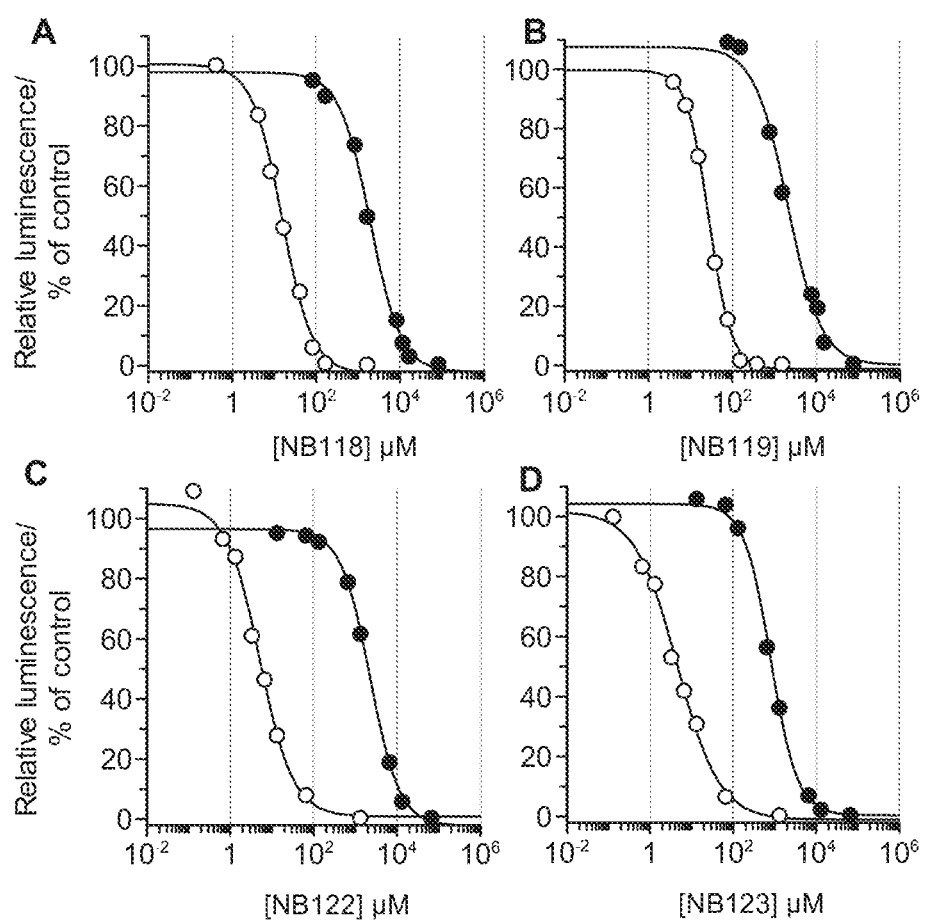
Figure 12:
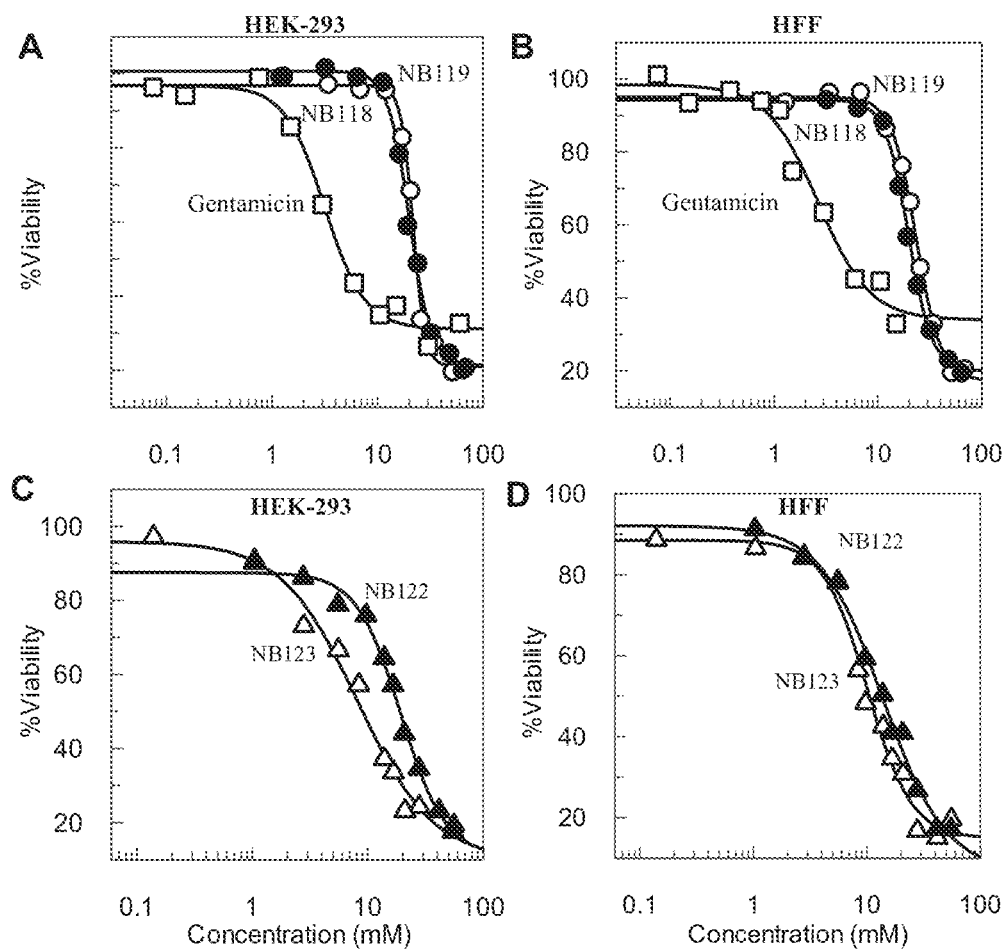

FIGS. 1A-C present a synthetic pathway for preparing C5-diasteromeric esters (R,X)-27 and (S,X)-28, according to some embodiments of the invention, wherein "a" represents DCC, 4-DMAP, CSA, DCM, at room temperature (FIG. 1A); $^1$H NMR spectra of (R,X)-27 and (S,X)-28, wherein the chemical shift differences ( ) between particular protons of (R,X)-27 and (S,X)-28 are highlighted (FIG. 1B); and an assignment of absolute configuration at the 5-carbon (denoted by X) of the major alcohol Compound 9 by Sector rule (FIG. 1C);

FIGS. 2A-F present the results of the stop codon readthrough assay showing comparative graphs of in vitro stop codon suppression levels induced by the previously reported NB30 (marked by empty circles), by exemplary compounds according to some embodiments of the present invention, NB118 (marked by black triangles) and NB119 (marked by empty triangles), and by the control drug gentamicin (marked by black rectangles) in a series of nonsense mutation context constructs representing various genetic diseases (in parenthesis), wherein results pertaining to the R3X (USH1) construct are shown in FIG. 2A, R245X (USH1) in FIG. 2B, G542X (CF) in FIG. 2C, W1282X (CF) in FIG. 2D, Q70X (HS) in FIG. 2E, and R3381X (DMD) in FIG. 2F;

FIGS. 3A-F present the results of the stop codon readthrough assay showing comparative graphs of in vitro stop codon suppression levels induced by the previously reported NB54 (marked by black circles), by exemplary compounds according to some embodiments of the present invention, NB122 (marked by black triangles) and NB123 (marked by empty triangles), and by gentamicin as a control drug (marked by black rectangles) in a series of nonsense mutation context constructs representing various genetic diseases (in parenthesis), wherein results pertaining to the R3X (USH1) construct are shown in FIG. 3A, R245X (USH1) in FIG. 3B, G542X (CF) in FIG. 3C, W1282X (CF) in FIG. 3D, Q70X (HS) in FIG. 3E, and R3381X (DMD) in FIG. 3F;

FIGS. 4A-D present ex vivo suppression of the PCDH15-R3X (FIG. 4A), PCDH15-R245X (FIG. 4B), IDUA-Q70X (FIG. 4C), and CFTR-W1282X (FIG. 4D) nonsense mutations, effected by the previously reported NB54 (marked by black circles), by exemplary compounds according to some embodiments of the present invention, NB122 (marked by black triangle) and NB123 (marked by empty triangles) and by the control drug gentamicin (marked by black rectangles);

FIGS. 5A-D present comparative plots of the results of in vitro premature stop codon mutation suppression assays of the CFTR-G542X (FIGS. 5A and 5C), and CFTR-W1282X (FIGS. 5B and D) effected by exemplary compounds according to some embodiments of the present invention, NB124 (marked by black circles), NB125 (marked by empty circles), NB127 (marked by black triangles), and NB128 (marked by empty triangles), by the previously reported NB74 (marked by empty rhombs) and NB84 (marked by black rhombs), and by the control drugs gentamicin (marked by black rectangles) and G418 (marked by empty rectangles);

FIGS. 6A-F present the results of the stop codon readthrough assay showing comparative graphs of in vitro stop codon readthrough levels induced by exemplary compounds according to some embodiments of the present invention, NB124 (marked by black circles) and NB125 (marked by empty circles), by the previously reported NB74 (marked by empty rhombs) and by the control drug gentamicin (marked by black rectangles), in a series of nonsense mutation context constructs representing various genetic diseases (in parenthesis), wherein results pertaining to the R3X (USH1) construct are shown in FIG. 6A, R245X (USH1) in FIG. 6B, G542X (CF) in FIG. 6C, W1282X (CF) in FIG. 6D, Q70X (HS) in FIG. 6E, and R3381X (DMD) in FIG. 6F;

FIGS. 7A-F present the results of the stop codon readthrough assay showing comparative graphs of in vitro stop codon suppression levels induced by the previously reported NB84 (marked by black rhombs), by exemplary compounds according to some embodiments of the present invention, NB127 (marked by black triangles) and NB128 (marked by empty triangles), and by the control drugs G418 (marked by empty rectangles) and gentamicin (marked by black rectangles), in a series of nonsense mutation context constructs representing various genetic diseases (in parenthesis), wherein results pertaining to the R3X (USH1) construct are shown in FIG. 7A, R245X (USH1) in FIG. 7B, G542X (CF) in FIG. 7C, W1282X (CF) in FIG. 7D, Q70X (HS) in FIG. 7E, and R3381X (DMD) in FIG. 7F;

FIGS. 8A-D present comparative plots of results of ex vivo premature stop codon mutation suppression assays conducted for the constructs CFTR-G542X (FIGS. 8A and 8C) and CFTR-W1282X (FIGS. 8B and 8D), effected by exemplary compounds according to some embodiments of the present invention, NB124 (marked by black circles), NB125 (marked by empty circles), NB127 (marked by black triangles) and NB128 (marked by empty triangles), by the previously reported NB74 (marked by empty rhombs) and NB84 (marked by black rhombs), and by the control drugs gentamicin (marked by black rectangles) and G418 (marked by empty rectangles);

FIGS. 9A-E present the results of the stop codon readthrough assay showing comparative graphs of ex vivo stop codon suppression levels induced by exemplary compounds according to some embodiments of the present invention, NB124 (marked by black circles) and NB125 (marked by empty circles), by the previously reported NB74 (marked by black rhombs), and by the control drugs gentamicin (marked by black rectangles) and G418 (marked by empty rectangles) in a series of nonsense mutation context constructs representing various genetic diseases (in parenthesis), wherein results pertaining to the R3X (USH1) construct are shown in FIG. 9A, R245X (USH1) in FIG. 9B, Q70X (HS) in FIG. 9C, W1282X (CF) in FIG. 9D and G542X (CF) in FIG. 9E;

FIGS. 10A-E present the results of the stop codon readthrough assay showing comparative graphs of ex vivo stop codon suppression levels induced by exemplary compounds according to some embodiments of the present invention, NB127 (marked by black rectangles) and NB128 (marked by empty triangles), by the previously reported NB84 (marked by black rhombs) and by the control drugs gentamicin (marked by black rectangles) and G418 (marked by empty rectangles), in a series of nonsense mutation context constructs representing various genetic diseases (in parenthesis), wherein results pertaining to the R3X (USH1) construct are shown in FIG. 10A, R245X (USH1) in FIG. 10B, Q70X (HS) in FIG. 10C, W1282X (CF) in FIG. 10D and G542X (CF) in FIG. 10E;

FIGS. 11A-D present semi-logarithmic plots of in vitro translation inhibition in prokaryotic (marked by black circles) and eukaryotic (marked by empty circles) systems measured for the exemplary compounds according to some embodiments of the present invention, NB118 (FIG. 11A), NB119 (FIG. 11B) NB122 (FIG. 11C) and NB123 (FIG. 11D);

FIGS. 12A-D present semi-logarithmic plots of the percentages of ex vivo cell viability versus concentration of the tested compound in HEK-293 (FIG. 12A and FIG. 12C) and in human foreskin fibroblasts (HFF) (FIG. 12B and FIG. 12D) cells, for gentamicin (marked by empty rectangles), and for exemplary compounds according to some embodiments of the present invention, NB118 (marked by empty circles), NB119 (marked by black circles), NB122 (marked by empty triangles), and NB123 (marked by black triangle); and FIGS. 13A-B present scatter plots for identifying possible correlation between readthrough activity and protein translation inhibition in vitro in eukaryotic systems as observed for a series of known compounds and exemplary compounds according to some embodiments of the present invention, wherein increasing inhibition of protein synthesis (lower $IC_{50}$ values) is associated with the increase of readthrough activity, whereas FIG. 13A is a semilogarithmic plot of eukaryotic inhibition of translation versus in vitro readthrough activity at 1.4 μM concentration of the tested aminoglycosides (shown on the X-axis) using six different nonsense mutations (W1282X, Q70X, R3X, R245X, G542X and R3381X) and FIG. 1B is a linear plot of the same data presented in FIG. 13A.

DESCRIPTION OF SPECIFIC EMBODIMENTS OF THE INVENTION

The present invention, in some embodiments thereof, relates to a new class of aminoglycosides and more particularly, but not exclusively, to novel aminoglycosides with improved efficacy towards treatment of genetic disorders.

Specifically, the present invention, in some embodiments thereof, relates to a new class of compounds, derived from paromomycin, which exhibit high premature stop codon mutations readthrough activity while exerting low toxicity in mammalian cells. The present invention is thus further of pharmaceutical compositions containing these compounds, and of uses thereof in the treatment of genetic disorders, such as cystic fibrosis (CF). The present invention is further of processes of preparing these compounds.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed above, several structural manipulations on the structure of paromamine have given rise to synthetic aminoglycosides which have been shown to exert improved premature stop-codon mutations readthrough activity while exerting low toxicity in mammalian cells. Following these structural manipulations has lead to the development of the exemplary compounds NB30 and NB54 as pseudo-trisaccharide derivatives of the clinical aminoglycoside paromomycin. The structural concept demonstrated in NB30 exhibited significantly reduced cytotoxicity in comparison to gentamicin and paromomycin, and promoted dose-dependent suppression of nonsense mutations of the PCDH15 gene, the underlying cause of type 1 Usher syndrome (USH1), but its suppression potency was notably lower relative to that of gentamicin and paromomycin. NB54, which was developed as the second-generation concept structure, exhibited significantly reduced cell, cochlear and acute toxicities, and has substantially higher readthrough efficiency than those of gentamicin and paromomycin.

While further deciphering the structure-activity relationship of such aminoglycosides, in an attempt to further improve their therapeutic effect in the context of genetic disorders, the present inventors have investigated numerous additional modifications, at varying positions of the paromamine structure, and have surprisingly found that by substituting a hydrogen on the 5" side-chain on the ribosamine ring (ring III) with a methyl group, the resulting aminoglycoside show significantly reduced cell toxicity while in parallel exhibit substantially higher readthrough activity of disease-causing nonsense mutations, even when compared to those of gentamicin. Hence, the present inventors have identified another significant position in the pharmacophore that constitutes viable drug candidates that can fight diseases that stem from genetic mutation.

Without being bound to any particular theory, it is suggested that introducing a modification at the ribosamine ring (Ring III) preserves already well established impacts of the rings I and II in the previous concept structures (see, for example, compounds NB30 and NB54 described supra), while introducing a new structural motif with significant suppression activity and reduced toxicity.

While reducing the present invention to practice, the present inventors have successfully prepared aminoglycosides (e.g., NB30, NB54 NB74 and NB84) to which the side-chain (S)-5"-methyl group was introduced to a ribosamine ring (ring III), and have thereby generated a new family of aminoglycosides. The present inventors have demonstrated that these newly designed compounds show significantly reduced cell toxicity while in parallel exhibit substantially higher readthrough activity of disease-causing nonsense mutations, as compared, for example, to gentamicin. It was also observed that the installation of (S)-5"-methyl group does not affect cell toxicity significantly, while it greatly enhances the stop-codon readthrough activity and specificity to the eukaryotic ribosome of the resulted structures in comparison to those of the previously reported structures.

Since the installation of a methyl group at C5"-position of the ribosamine ring generates a new stereogenic center, the present inventors have prepared both C5"-diastereomers with defined absolute configuration and compared their biological properties.

Hence, a new pharmacophore point, (S)-5"-methyl group, has been discovered as a valuable structural element of the ribosamine ring (ring III) that significantly affects suppression activity and has no significant influence on cell toxicity.

This new pharmacophore point is a fifth point now added to the previous four points discovered and disclosed in, for example, WO 2007/113841. Scheme 1 presents the paromamine core with all five pharmacophore points discovered hitherto, numbered i-iv according to the sequence of their discovery. Specifically, the pharmacophore point denoted "i" refers to the provision of a hydroxyl group in position 6'; the point denoted "ii" refers to the provision of an AHB group in position N1; point "iii" refers to the provision of a third saccharide moiety (Ring III) attached to the second saccharide ring; "iv" is the provision of a modification at position 6' (exemplified in Scheme 1 as a lower alkyl); and the pharmacophore point disclosed herein is denoted "v" and refers to the provision of modification at position 5" (exemplified in Scheme 1 as a lower alkyl).

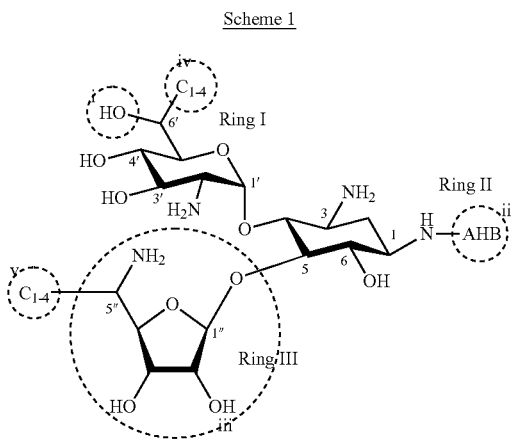

Scheme 1

Hence, according to an aspect of embodiments of the present invention, there is provided a compound having the general formula I:

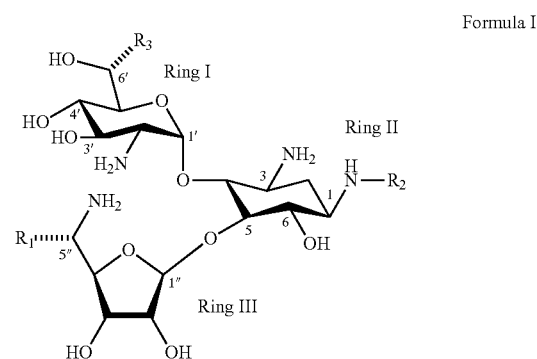

Formula I or a pharmaceutically acceptable salt thereof,
wherein:
$R_1$ is selected from the group consisting of alkyl, cycloalkyl and aryl, and is preferably alkyl;
$R_2$ is hydrogen or (S)-4-amino-2-hydroxybutyryl (AHB);
$R_3$ is selected from the group consisting of hydrogen, alkyl, cycloalkyl or aryl, and is preferably hydrogen or alkyl; and
a stereo-configuration of each of position 6' and position 5" is independently an R configuration or an S configuration.

It is noted herein that while the position of Ring III at position O5 on Ring II has been shown to exhibit optimal results, other positions for Ring III are contemplated, such as position O6 on Ring II and positions 3' and 4' on Ring I.

The terms "hydroxyl" or "hydroxy", as used herein, refer to an —OH group.

As used herein, the term "amine" describes a —NR'R" group where each of R' and R" is independently hydrogen, alkyl, cycloalkyl, heteroalicyclic, aryl or heteroaryl, as these terms are defined herein.

As used herein, the term "alkyl" describes an aliphatic hydrocarbon including straight chain and branched chain groups. The alkyl may have 1 to 20 carbon atoms, or 1-10 carbon atoms, and may be branched or unbranched. According to some embodiments of the present invention, the alkyl is a low alkyl, having 1-4 carbon atoms (namely, methyl, ethyl, propyl and butyl).

The term "cycloalkyl" refers to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. Exemplary cycloalkyl groups include, for example, cyclopropyl, cyclobutyl, cyclopentyl, cyclohexyl, or cyclododecyl.

Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms. An alkyl can be substituted or unsubstituted. When substituted, the substituent can be, for example, an alkyl (forming a branched alkyl), an alkenyl, an alkynyl, a cycloalkyl, an aryl, a heteroaryl, a halo, a hydroxy, an alkoxy and a hydroxyalkyl as these terms are defined hereinbelow. The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and i-propenyl. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, alkyl cycloalkyl, alkenyl, alkynyl, aryl, heteroaryl and heteroalicyclic. Representative examples are morpholine, piperidine, piperazine, tetrahydrofurane, tetrahydropyrane and the like.

The term "halide", as used herein, refers to the anion of a halo atom, i.e. $F^-$, $Cl^-$, $Br^-$ and $I^-$.

The term "halo" refers to F, Cl, Br and I atoms as substituents.

The term "alkoxy" refers to an $R'—O^-$ anion, wherein R' is as defined hereinabove.

The term "hydroxyalkyl," as used herein, refers to an alkyl group substituted with one hydroxy group, e.g., hydroxymethyl, p-phydroxyethyl and 4-hydroxypentyl.

The term "alkoxyalkyl," as used herein, refers to an alkyl group substituted with one alkoxy group, e.g., methoxymethyl, 2-methoxyethyl, 4-ethoxybutyl, n-propoxyethyl and t-butylethyl.

The moiety (S)-4-amino-2-hydroxybutyryl, is also referred to herein as AHB. According to some embodiments of the present invention, an alternative to the AHB moiety can be the α-hydroxy-β-aminopropionyl (AHP) moiety. These so-called side chains or optional moieties are believed to block the access of aminoglycoside-modifying enzymes to the target sites. Moreover, AHB or AHP contain a 1,3- or 1,2-hydroxylamine moiety that binds to phosphodiesters and to the hoogsten base face of guanosine of the A-site of 16S rRNA. It is noted herein that according to some embodiments of the present invention, other moieties which involve a combination of carbonyl(s), hydroxyl(s) and amino group(s) along a lower alkyl exhibiting any stereochemistry, are contemplated as optional substituents in place of AHB and/or AHP. For example, 2-amino-3-hydroxybutanoyl, 3-amino-2-hydroxypentanoyl, 5-amino-3-hydroxyhexanoyl and the likes.

Herein, it is to be understood that whenever reference is made to AHB, equivalent groups as described herein (e.g., AHP) are also encompassed.

As used herein, the phrase "moiety" describes a part, and preferably a major part, of a chemical entity, such as a molecule or a group, which has underwent a chemical reaction and is now covalently linked to another molecular entity.

According to some embodiments of the present invention, $R_1$ is alkyl.

According to some embodiments, $R_1$ is a lower alkyl as defined herein, including, but not limited to, methyl, ethyl, propyl, butyl, and isopropyl. According to other embodiments of the present invention, $R_1$ is methyl.

Alternatively, $R_1$ is cycloalkyl, including, but not limited to, cyclopropyl, cyclobutyl, cyclopentyl and cyclohexyl.

Further alternatively, $R_1$ is aryl, such as substituted or unsubstituted phenyl. Non-limiting examples include phenyl and toluene.

In some embodiments of the present invention, R1 is alkyl, as described herein, and $R_2$ and $R_3$ are each hydrogen. In terms of the pharmacophore points presented in Scheme 1 (vide supra), these compounds possess the fifth (v) point and do not possess the second (ii) and fourth (iv) points. These compounds exhibit superior pharmacologic profile compared to previously known compounds and drugs which are considered for use in treating genetic disorders, namely these compounds are less toxic and more efficient in reading-through premature stop codon mutations, as demonstrated in the Examples section that follows below.

Exemplary aminoglycoside compounds which exhibit hydrogen in positions $R_2$ and $R_3$ include:

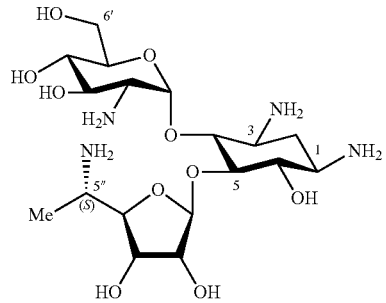

NB118 and

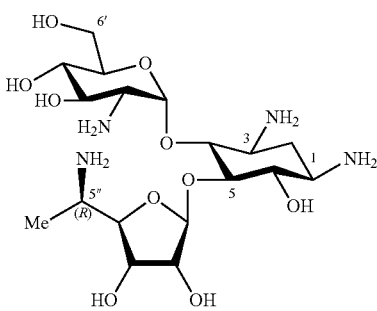

NB119 which differ from each other in the stereo-configuration of the chiral center at position 5" of Ring III.

Optionally, $R_1$ is cycloalkyl, as described herein, and $R_2$ and $R_3$ are each hydrogen.

Optionally, $R_1$ is aryl, as described herein, and $R_2$ and $R_3$ are each hydrogen.

In some embodiments of the present invention, $R_1$ is alkyl, as described herein, $R_2$ is AHB and $R_3$ is a hydrogen atom. In terms of the pharmacophore points presented in Scheme 1 (vide supra), other than possessing the fifth (v) point, these compounds possess the second (ii) point and do not possess the fourth (iv) point. These compounds exhibit superior pharmacologic profile compared to previously known compounds and drugs which are considered for use in treating genetic disorders, namely these compounds are less toxic and more efficient in reading-through premature stop codon mutations, as demonstrated in the Examples section that follows below.

Exemplary aminoglycoside compounds having an AHB moiety at position $R_2$ and hydrogen in $R_3$ include:

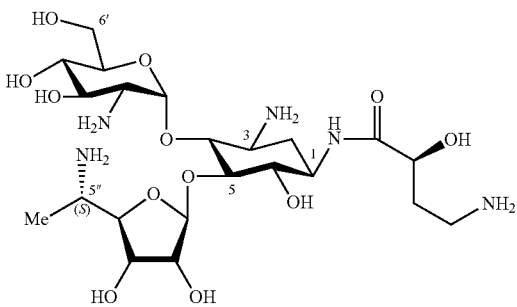

NB122 and

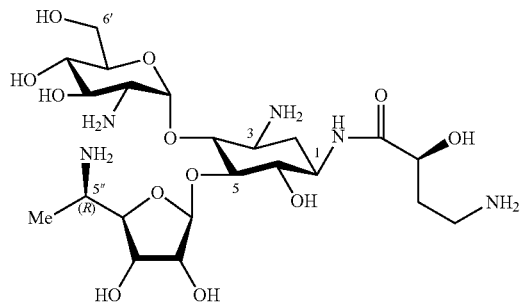

NB123 which differ from each other in the stereo-configuration of the chiral center at position 5" of Ring III.

Optionally, $R_1$ is cycloalkyl, as described herein, $R_2$ is AHB and $R_3$ is a hydrogen atom.

Optionally, $R_1$ is aryl, as described herein, $R_2$ is AHB and $R_3$ is a hydrogen atom.

In some embodiments of the present invention, $R_1$ is alkyl, as described herein, $R_2$ is hydrogen and $R_3$ is alkyl. In terms of the pharmacophore points presented in Scheme 1 (vide supra), other than possessing the fifth (v) point, these compounds do not possess the second (ii) point and do possess the fourth (iv) point. These compounds exhibit superior pharmacologic profile compared to previously known compounds and drugs which are considered for use in treating genetic disorders, namely these compounds are less toxic and more efficient in reading-through premature stop codon mutations, as demonstrated in the Examples section that follows below.

Optionally, $R_1$ is cycloalkyl, as described herein, $R_2$ is hydrogen and $R_3$ is alkyl.

Optionally, $R_1$ is aryl, as described herein, $R_2$ is hydrogen and $R_3$ is alkyl.

According to some embodiments of the present invention, in any of the above-described embodiments where $R_3$ is alkyl, $R_3$ is a lower alkyl, as defined herein. According to these embodiments, $R_3$ is methyl.

Optionally, $R_1$ is alkyl, as described herein, $R_2$ is hydrogen and $R_3$ is cycloalkyl.

Optionally, $R_1$ is cycloalkyl, as described herein, $R_2$ is hydrogen and $R_3$ is cycloalkyl.

Optionally, $R_1$ is aryl, as described herein, $R_2$ is hydrogen and $R_3$ is cycloalkyl.

Optionally, $R_1$ is alkyl, as described herein, $R_2$ is hydrogen and $R_3$ is aryl.

Optionally, $R_1$ is cycloalkyl, as described herein, $R_2$ is hydrogen and $R_3$ is aryl.

Optionally, $R_1$ is aryl, as described herein, $R_2$ is hydrogen and $R_3$ is aryl.

Exemplary aminoglycoside compounds which exhibit hydrogen in position $R_2$ and alkyl in position $R_3$ include:

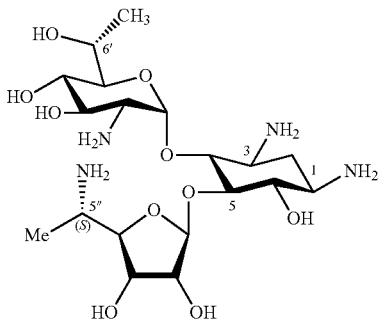

NB124

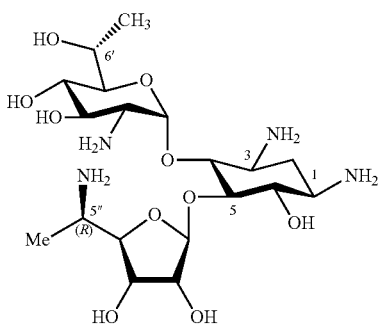

NB125 which differ from each other in the stereo-configuration of the chiral center at position 5" of Ring III.

In some embodiments of the present invention, $R_2$ is AHB and $R_3$ is alkyl. In terms of the pharmacophore points presented in Scheme 1 (vide supra), these compounds possess all five points; These compounds exhibit the most superior pharmacologic profile compared to previously known compounds and drugs in terms of lower cytotoxicity and higher in readthrough efficiency, as demonstrated in the Examples section that follows below.

Exemplary aminoglycoside compounds wherein $R_2$ is AHB and $R_3$ is alkyl include:

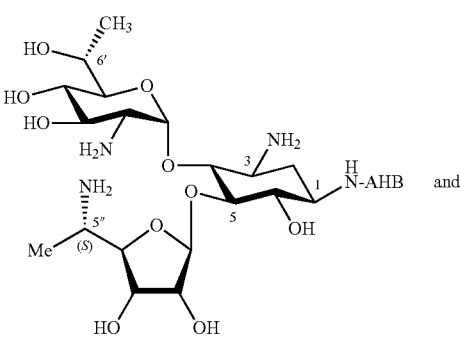

NB127 and

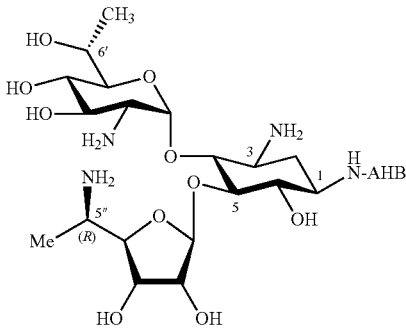

NB128 which differ from each other in the stereo-configuration of the chiral center at position 5" of Ring III.

Optionally, $R_1$ is cycloalkyl, as described herein, $R_2$ is AHB and $R_3$ is alkyl.

Optionally, $R_1$ is aryl, as described herein, $R_2$ is AHB and $R_3$ is alkyl.

According to some embodiments of the present invention, in any of the above-described embodiments where $R_3$ is alkyl, $R_3$ is a lower alkyl, as defined herein. According to these embodiments, $R_3$ is methyl.

Optionally, $R_1$ is alkyl, as described herein, $R_2$ is AHB and $R_3$ is cycloalkyl.

Optionally, $R_1$ is cycloalkyl, as described herein, $R_2$ is AHB and $R_3$ is cycloalkyl.

Optionally, $R_1$ is aryl, as described herein, $R_2$ is AHB and $R_3$ is cycloalkyl.

Optionally, $R_1$ is alkyl, as described herein, $R_2$ is AHB and $R_3$ is aryl.

Optionally, $R_1$ is cycloalkyl, as described herein, $R_2$ is AHB and $R_3$ is aryl.

Optionally, $R_1$ is aryl, as described herein, $R_2$ is AHB and $R_3$ is aryl.

While searching for a way to predict and evaluate quantitatively the capacity of a synthetic aminoglycoside to constitute a drug candidate for treating genetic diseases caused by premature stop codon mutations (exhibit readthrough activity) and at the same time exhibit low or no cytotoxicity, it was found that high selectivity of the compound to eukaryotic cytoplasmic translation systems (i.e., eukaryotic cytoplasmic ribosomes) compared to prokaryotic translation systems, which are similar or resembles to some extent the mitochondrial translation system, can be used as a predictive measure. A numeric value that can readily be used to quantify this selectivity is the ratio $IC_{50}^{Euk}/IC_{50}^{Pro}$ which correlates an inhibition of translation in eukaryotes to inhibition of translation in prokaryotes (see, Table 3 hereinbelow). As demonstrated in the Examples section below, a notable selectivity of any given aminoglycoside compound, such as the compounds according to some embodiments of the present invention, towards inhibiting translation in eukaryote over inhibiting translation in prokaryote can be used to predict its effectiveness and safety as a drug candidate for treating genetic disorders associated with premature stop codon mutations.

Nonetheless, it is noted herein that the $IC_{50}^{Euk}/IC_{50}^{Pro}$ ratio which indicates selectivity, is not a sufficient criteria for selecting drug candidates from this family of aminoglycosides; one must also consider the mechanism of translation inhibition. For example, it was found that the aminoglycoside NB33, which is a dimer of the parent compound paromamine, exhibits a ratio value of about 2, which is regarded as low and thus predictive for a good readthrough drug candidate. However, NB33 exhibits essentially no readthrough activity. It is assumed that NB33 inhibits the translation mechanism in a different inhibition mode, as shown in the crystal of complex between the cytoplasmic A site RNA and NB33 [*ChemBio-Chem*, 2007, 8(14), p. 1617].

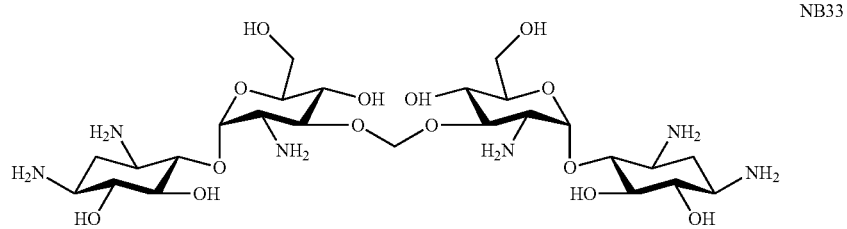

NB33

Without being bound by any particular theory, one possible conclusion from the above discussion is that for an aminoglycoside to exhibit desired traits of a premature stop codon mutation readthrough drug candidate, 1) it should inhibit both prokaryotic and eukaryotic ribosomes by same mechanism of to binding to the aminoacyl-tRNA binding site and stabilizing the decoding conformation, or inhibit protein translation process by interfering with the fidelity of proof-reading process; and 2) the $IC_{50}^{Euk}/IC_{50}^{Pro}$ ratio favoring eukaryotes should also be accompanied with a significant decrease in the specificity of the compound to the prokaryotic ribosome; in other words elevated $IC_{50}^{Pro}$ values. A representative example for this requirement is G418; it $IC_{50}^{Euk}/IC_{50}^{Pro}$ ratio is 225, which is significantly lower to that of gentamicin but still it is highly toxic as indicated by a relatively very low $IC_{50}^{Pro}$ value.

Thus, according to some embodiments of the present invention, the compounds presented herein are characterized by a ratio of $IC_{50}$ translation inhibition in eukaryotes to $IC_{50}$ translation inhibition in prokaryotes lower than 15, lower than 10, lower than 5 or lower than 1, including any intermediate value between 15 and 1.

As demonstrated hereinbelow, while preparing and testing exemplary compounds according to some embodiments of the present invention, it has been observed that the increased inhibition of prokaryotic cytoplasmic protein synthesis is also associated with increased readthrough activity. Data presented in Table 3 shows that the systematic addition of points of the pharmacophore presented in Scheme 1 gradually increases the specificity of compounds to the cytoplasmic ribosome and decrease their specificity to the prokaryotic ribosome.

It would be reasonable to expect aminoglycosides to be selective towards prokaryotes, since aminoglycosides have developed by natural selection in *Streptomyces* genus and other species such as species *Saccharopolyspora erythraea*, to be active against other prokaryotes. Nonetheless, compounds according to some embodiments of the present invention, exhibit reversed selectivity to eukaryotic versus prokaryotic translation systems (ribosome).

Thus, according to some embodiments of the present invention, the compounds presented herein are characterized by a ratio of $IC_{50}$ translation inhibition in eukaryotes to $IC_{50}$ translation inhibition in prokaryotes lower than 15, lower than 1.

As discussed hereinabove, a promising aminoglycoside compound, according to some embodiments of the present invention, is one that does not have a notable or any antimicrobial activity. Such non-activity is also predictive for low or no cytotoxicity of the compound to mammalians. The results, which show that the exemplary compounds which have been prepared and tested for antimicrobial activity or lack thereof, are presented in Tables 1 and 2 hereinbelow.

Hence, according to some embodiments of the present invention, the compounds presented herein are characterized by a MIC value in Gram-negative bacteria which is higher than 200 μM, higher than 300 μM, higher than 500 μM, higher than 700 μM, or higher than 1000 μM, as well as a MIC value in Gram-positive bacteria which is higher than 20 μM, higher than 40 μM, higher than 80 μM, or higher than 100 μM.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a hydroxyl anion (O$^-$) and a cation such as, but not limited to, ammonium, sodium, potassium and the like. Another example, without limitation, of a pharmaceutically acceptable salt would be an ammonium cation and an acid addition salt thereof. Examples of acid addition salts include, but are not limited to, hydrochloric acid addition salt, sulfuric acid addition salt (sulfate salt), acetic acid addition salt, ascorbic acid addition salt, benzenesulfonic acid addition salt, camphorsulfonic acid addition salt, citric acid addition salt, maleic acid addition salt, methanesulfonic acid addition salt, naphthalenesulfonic acid addition salt, oxalic acid addition salt, phosphoric acid addition salt, succinic acid addition salt, sulfuric acid addition salt, tartaric acid addition salt, and toluenesulfonic acid addition salt.

According to some embodiments of the present invention, the acid addition salt is a sulfate salt.

Further according to the present invention, there are provided processes of preparing the compounds described herein.

The synthetic pathways described herein include a reaction between an acceptor and a donor, whereby the term "acceptor" is used herein to describe the skeletal structure derived from paromamine which has at least one and preferably selectively selected available (unprotected) hydroxyl group at positions such as C5, C6 and C3', which is reactive during a glycosylation reaction, and can accept a glycosyl, and the term "donor" is used herein to describe the glycosyl. According to some embodiments of the present invention, the position on the acceptor is the C5 position.

The term "glycosyl", as used herein, refers to a chemical group which is obtained by removing the hydroxyl group from the hemiacetal function of a monosaccharide and, by extension, of a lower oligosaccharide.

The term "monosaccharide", as used herein and is well known in the art, refers to a simple form of a sugar that consists of a single saccharide molecule which cannot be further decomposed by hydrolysis. Most common examples of monosaccharides include glucose (dextrose), fructose, galactose, and ribose. Monosaccharides can be classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms. Monosaccharides are the building blocks of oligosaccharides like sucrose (common sugar) and other polysaccharides (such as cellulose and starch).

The term "oligosaccharide" as used herein refers to a compound that comprises two or more monosaccharide units, as these are defined herein. According to some embodiments of the present invention, an oligosaccharide comprises 2-6 monosaccharides. Alternatively, an oligosaccharide comprises 2-4 monosaccharides, or further alternatively, an oligosaccharide is a disaccharide moiety, having two monosaccharide units.

The donors and acceptors are designed so as to form the desired compounds according to some embodiments of the present invention. The following describes some embodiments of this aspect of the present invention, presenting exemplary processes of preparing exemplary subsets of the compounds described herein. Detailed processes of preparing exemplary compounds according to some embodiments of the present invention, are presented in the Examples section that follows below.

The syntheses of the compounds according to some embodiments of the present invention, generally include (i) preparing an acceptor compound by selective protection of one or more hydroxyls and amines at selected positions present on the paromamine scaffold, leaving one or two positions unprotected and therefore free to accept a donor (glycosyl) compound as defined herein; (ii) preparing a donor compound by selective protection of one or more hydroxyls and amines at selected positions present on the glycosyl, leaving one position unprotected and therefore free to couple with an acceptor compound as defined herein; (iii) subjecting the donor and the acceptor to a coupling reaction; and (iii) removing of all protecting groups to thereby obtain the desired compound.

The phrase "protecting group", as used herein, refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include azide (azido), N-phthalimido, N-acetyl, N-trifluoroacetyl, N-t-butoxycarbonyl (BOC), N-benzyloxycarbonyl (CBz) and N-9-fluorenylmethylenoxycarbonyl (Fmoc). Similarly, a "hydroxyl-protecting group" refers to a substituent of a hydroxyl group that blocks or protects the hydroxyl functionality. Suitable protecting groups include isopropylidene ketal and cyclohexanone dimethyl ketal (forming a 1,3-dioxane with two adjacent hydroxyl groups), 4-methoxy-1-methylbenzene (forming a 1,3-dioxane with two adjacent hydroxyl groups), O-acetyl, O-chloroacetyl, O-benzoyl and O-silyl. For a general description of protecting groups and their use, see T. W. Greene, Protective Groups in Organic Synthesis, John Wiley & Sons, New York, 1991.

According to some embodiments, the amino-protecting groups include an azido (N$_3$-) and/or an N-phthalimido group, and the hydroxyl-protecting groups include O-acetyl (AcO-), O-benzoyl (BzO-) and/or O-chloroacetyl. It is noted herein that when applicable, a "protecting group" refers to a moiety that can protect one reactive function on a compound or more than one function at the same time, such as in the case of two adjacent functionalities, e.g., two hydroxyl groups that can be protected at once by a isopropylidene ketal.

Hence, there is provided a process of preparing the compounds having the general Formula I as presented herein. The process is effected by preparing a suitably protected acceptor compound and a suitably protected donor compound, coupling these two compounds to one another, and subsequently removing all the protecting groups from the resulting compound.

The donor compound is a protected monosaccharide which can be represented by the general Formula II, having a leaving group at position 1" thereof, denoted L, and an alkyl, cycloalkyl or aryl at position 5", denoted $R_1$:

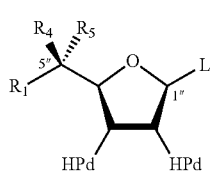

Formula II wherein:

$R_1$ is selected from the group consisting of alkyl, cycloalkyl and aryl;

$R_4$ is hydrogen or a donor amino-protecting group;

$R_5$ is a donor amino-protecting group if $R_4$ is hydrogen or hydrogen if $R_4$ is a donor amino-protecting group; and each of HPd is a donor hydroxyl-protecting group.

It is noted herein that the absolute stereo-configuration of the chiral center at position 5" is determined by the identity of $R_4$ and $R_5$, giving both options of R- and S-configuration as two individual and separable donors (being diastereomers) or as a racemic mixture thereof. A detailed process for obtaining each of the R- and S-donor compounds and a method for assigning the absolute stereo-configuration thereof is presented in the Examples section below.

As used herein, the phrase "leaving group" describes a labile atom, group or chemical moiety that readily undergoes detachment from an organic molecule during a chemical reaction, while the detachment is facilitated by the relative stability of the leaving atom, group or moiety thereupon. Typically, any group that is the conjugate base of a strong acid can act as a leaving group. Representative examples of suitable leaving groups according to the present embodiments therefore include, without limitation, trichloroacetimidate, acetate, tosylate, triflate, sulfonate, azide, halide, hydroxy, thiohydroxy, alkoxy, cyanate, thiocyanate, nitro and cyano.

According to some embodiments of the present invention, the leaving group is trichloroacetimidate, which gave the most satisfactory results in the coupling reaction with the acceptor, although other leaving groups are contemplated.

According to some embodiments of the present invention, each of the donor hydroxyl-protecting groups is O-benzoyl and the donor amino-protecting group in either $R_4$ or $R_5$ is azido, although other protecting groups are contemplated.

The structure of the donor compound sets the absolute structure of Ring III in the resulting compound according to some embodiments of the present invention, namely the stereo-configuration of the 5" position and the type of alkyl at that position. Exemplary donor compounds, suitable for affording compounds according to some embodiments of the present invention, include Compound (S)-17 and Compound (R)-18, the preparation thereof is illustrated in Scheme 2 hereinbelow.

The acceptor, according to some embodiments, has the general Formula III:

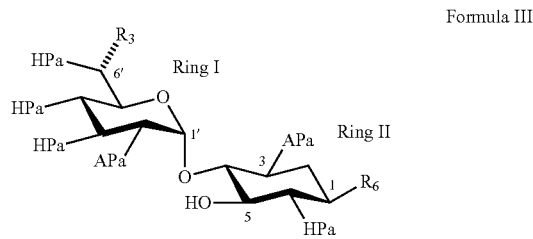

Formula III wherein:

the dashed line indicates an R configuration or an S configuration;

$R_3$ is selected from the group consisting of hydrogen, alkyl, cycloalkyl and aryl;

$R_6$ is an acceptor amino-protecting group or (S)-4-azido-2-O-acetyl-1-butyryl (a protected form of AHB);

HPa is an acceptor hydroxyl-protecting group; and

APa is an acceptor amino-protecting group.

According to some embodiments of the present invention, the acceptor hydroxyl-protecting group is O-acetyl, and the donor amino-protecting group is azido, although other protecting groups are contemplated.

It is noted herein that the exemplary embodiment provided hereinabove refers to a protected for of AHB, however it is not meant to be limiting to use of the AHB moiety as other useful moieties, such as AHP as presented hereinabove, may be used instead. In those cases the process will be modified by using an acceptor compound wherein the reactive groups of the moiety used in place of AHB are protected accordingly.

The structure of the acceptor compound sets the absolute structure of Ring I and Ring II in the resulting compound according to some embodiments of the present invention, namely the stereo-configuration of the 6' position and the type of alkyl at that position when present, and the substituent on the amino group at position N1. Exemplary acceptor compounds, suitable for affording compounds according to some embodiments of the present invention, include Compounds 19, 20, 219 and 220, the preparation of which is illustrated in Scheme 3 and Scheme 4 hereinbelow.

The process is therefore effected by:

(a) providing both the desired donor compound and desired acceptor compound;

(a) coupling the aforementioned acceptor compound to the aforementioned donor compound (also referred to as a glycosylation reaction); and (b) subsequently removing each of the protecting groups to thereby obtain the desired compound.

For example, the exemplary compound NB118 can be afforded by deprotecting Compound (S)-21, which is obtained by glycosilating (coupling) acceptor Compound 19 with donor Compound (S)-17. Correspondingly, the exemplary compound NB119 is obtained by deprotecting Compound (R)-22 which is the product of coupling acceptor Compound 19 with donor Compound (R)-18.

Similarly, the exemplary compound NB122 is afforded by deprotecting Compound (S)-23, the coupling product between acceptor Compound 20 and donor Compound (S)-17. Correspondingly, the exemplary compound NB123 is obtained by deprotecting Compound (R)-24 which is the product of coupling acceptor Compound 20 with donor Compound (R)-18.

The exemplary compound NB124 is afforded by deprotecting Compound (S)-221, the coupling product between acceptor Compound 219 and donor Compound (S)-17. Correspondingly, the exemplary compound NB125 is obtained by deprotecting Compound (R)-222 which is the product of coupling acceptor Compound 219 with donor Compound (R)-18.

The exemplary compound NB127 is afforded by deprotecting Compound (S)-223, the coupling product between acceptor Compound 220 and donor Compound (S)-17. Correspondingly, the exemplary compound NB128 is obtained by deprotecting Compound (R)-224 which is the product of coupling acceptor Compound 220 with donor Compound (R)-18.

As demonstrated in the Examples section that follows the compounds presented herein were designed so as to, and were indeed shown to, possess a truncation mutation suppression activity, namely the ability to induce readthrough of a premature stop codon mutation. Such an activity renders these compounds suitable for use as therapeutically active agents for the treatment of genetic disorders, and particularly such disorders which are characterized by a truncation mutation.

Thus, according to another aspect of the present invention there is provided a method of treating a genetic disorder. The method, according to this aspect of the present invention, is effected by administering to a subject in need thereof a therapeutically effective amount of one or more of the compounds presented herein having a general Formula I.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

The phrase "genetic disorder", as used herein, refers to a chronic disorder which is caused by one or more defective genes that are often inherited from the parents, and which can occur unexpectedly when two healthy carriers of a defective recessive gene reproduce, or when the defective gene is dominant. Genetic disorders can occur in different inheritance patterns which include the autosomal dominant pattern wherein only one mutated copy of the gene is needed for an offspring to be affected, and the autosomal recessive pattern wherein two copies of the gene must be mutated for an offspring to be affected.

According to some embodiments the genetic disorder involves a gene having a truncation mutation which leads to improper translation thereof. The improper translation causes a reduction or abolishment of synthesis of an essential protein.

Exemplary such genetic disorders include, but are not limited to, cystic fibrosis (CF), Duchenne muscular dystrophy (DMD), ataxia-telangiectasia, Hurler syndrome, hemophilia A, hemophilia B, Usher syndrome and Tay-Sachs.

Accordingly, there is provided a use of a compound having the general Formula I as presented herein in the manufacture of a medicament for treating a genetic disorder.

In any of the methods and uses described herein, the compounds described herein can be utilized either per se or form a part of a pharmaceutical composition, which further comprises a pharmaceutically acceptable carrier.

Thus, further according to the present invention, there is provided a pharmaceutical composition which comprises, as an active ingredient, any of the novel compounds described herein and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

According to some embodiments, the administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols. In addition, stabilizers may be added.

All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglicoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds presented herein to allow for the preparation of highly concentrated solutions.

Alternatively, the compounds presented herein may be in powder form for constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 50-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc. Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an indicated condition or diagnosis, as is detailed hereinabove.

Thus, in some embodiments, the pharmaceutical composition is packaged in a packaging material and identified in print, in or on the packaging material, for use in the treatment of a genetic disorder, as defined herein.

In any of the composition, methods and uses described herein, the compounds can be utilized in combination with other agents useful in the treatment of the genetic disorder.

Being primarily directed at treating genetic disorders, which are chronic by definition, the compounds presented herein or pharmaceutical compositions containing the same are expected to be administered throughout the lifetime of the subject being treated. Therefore, the mode of administration of pharmaceutical compositions containing the compounds should be such that will be easy and comfortable for administration, preferably by self-administration, and such that will take the smallest toll on the patient's wellbeing and course of life.

The repetitive and periodic administration of the compounds presented herein or the pharmaceutical compositions containing the same can be effected, for example, on a daily basis, i.e. once a day, more preferably the administration is effected on a weekly basis, i.e. once a week, more preferably the administration is effected on a monthly basis, i.e. once a month, and most preferably the administration is effected once every several months (e.g., every 1.5 months, 2 months, 3 months, 4 months, 5 months, or even 6 months).

As discussed hereinabove, some of the limitations for using presently known aminoglycosides as truncation mutation readthrough drugs are associated with the fact that they are primarily antibacterial (used as antibiotic agents). Chronic use of any antibacterial agents is highly unwarranted and even life threatening as it alters intestinal microbial flora which may cause or worsen other medical conditions such as flaring of inflammatory bowel disease, and may cause the emergence of resistance in some pathological strains of microorganisms.

In some embodiments, the compounds presented herein have substantially no antibacterial activity. By "no antibacterial activity" it is meant that the minimal inhibition concentration (MIC) thereof for a particular strain is much higher than the concentration of a compound that is considered an antibiotic with respect to this strain. Further, the MIC of these compounds is notably higher than the concentration required for exerting truncation mutation suppression activity.

Being substantially non-bactericidal, the compounds presented herein do not exert the aforementioned adverse effects and hence can be administered via absorption paths that may contain benign and/or beneficial microorganisms that are not targeted and thus their preservation may even be required. This important characteristic of the compounds presented herein renders these compounds particularly effective drugs against chronic conditions since they can be administered repetitively and during life time, without causing any antibacterial-related adverse, accumulating effects, and can further be administered orally or rectally, i.e. via the GI tract, which is a very helpful and important characteristic for a drug directed at treating chronic disorders.

As discussed hereinabove, according to some embodiments, the compounds presented herein are selective towards the eukaryotic cellular translation system versus that of prokaryotic cells, namely the compounds exhibit higher activity in eukaryotic cells, such as those of mammalian (humans) as compared to their activity in prokaryotic cells, such as those of bacteria. Without being bound by any particular theory, it is assumed that the compounds presented herein, which are known to act by binding to the A-site of the 16S ribosomal RNA while the ribosome is involved in translating a gene, have a higher affinity to the eukaryotic ribosomal A-site, or otherwise are selective towards the eukaryotic A-site, versus the prokaryotic ribosomal A-site, as well as the mitochondrial ribosomal A-site which resembles its prokaryotic counterpart.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is expected that during the life of a patent maturing from this application many relevant aminoglycosides having a 5"-alkyl group will be developed and the scope of this term is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Chemical Synthesis

Synthetic Procedures:

Compounds NB118, NB119, NB122, NB123, NB124, NB125, NB127 and NB128 were synthesized according to a general procedure that involves construction of Ring III as two individual compounds possessing (S)-5-methyl and (R)-5-methyl with already established stereochemistry (Compound (S)-17 and Compound (R)-18), and using them as donors for the glycosylation reactions. These donors were readily accessible from the known thioglycoside Compound 7 as illustrated in Scheme 2 below (wherein "a" represents 1,1-dimethoxypropane, CSA, acetone, room temperature; "b" represents Dess-Martin periodinane (DMP), DCM, room temperature; "c" represents MeMgBr, THF, −30° C.; "d" represents TsCl, Py, 4-DMAP, room temperature; "e" represents NaN3, HMPA, DMF, 70° C.; "f" represents acetic acid/water (8:2), reflux; "g" represents BzCl, Py, 4-DMAP, room temperature; "h" represents NBS, acetone/water (8:2), −30° C.; and "I" represents CCl3CN, DBU, DCM, 0° C.).

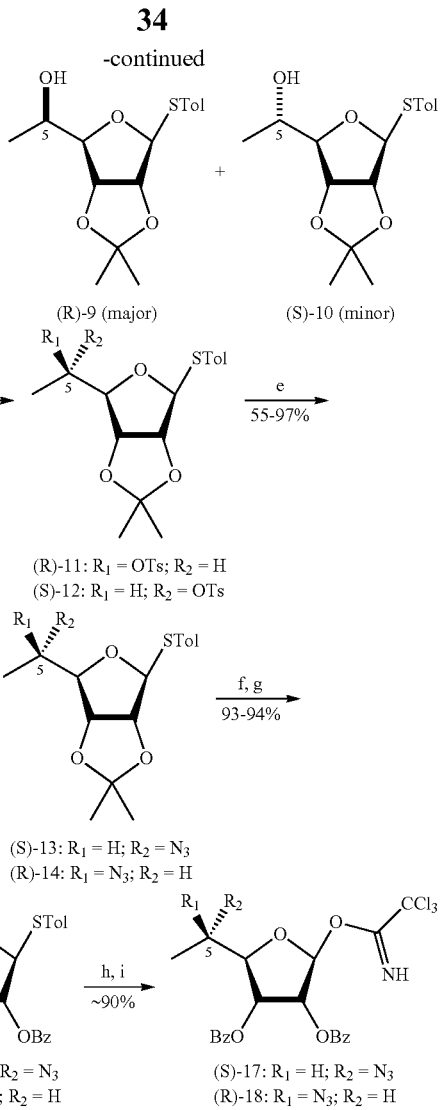

Selective protection of C2- and C3-hydroxyls by isopropylidine (2,2-dimethoxy propane/acetone, CSA) was followed by oxidation of the remaining primary alcohol using Dess-Martin periodinane (DMP, dichloromethane) to afford the aldehyde Compound 8 in 70% isolated yield for two steps. Treatment of Compound 8 with MeMgBr gave the corresponding secondary alcohol as a mixture of C5-diasteromers (4:1 ratio) in 88% isolated yield. This mixture was separated by flash column chromatography and the major diastereomer was separately subjected for the assignment of absolute stereochemistry at the C5-position (vide infra). This study established that the major and minor diastereomers exhibit (R)- and (S)-configuration, respectively (Compounds (R)-9 and (S)-10).

The following steps in Scheme 2 were separately performed on each diastereomer. Tosylation (TsCl, pyridine, 4-DMAP) of the secondary alcohol was followed by $S_N2$ displacement of the corresponding tosylates (Compounds (R)-11 and (S)-12) with $NaN_3$ (DMF, HMPA) to furnish the azides Compounds (S)-13 and (R)-14 with inverted configurations. Hydrolysis of the isopropylidene ketal with aqueous acetic acid, followed by benzoylation of the resulted secondary alcohols, provided the benzoates Compounds (S)-15 and (R)-16. Earlier studies on the assembly of the pseudo-trisaccharides NB30 and NB54 have demonstrated that the desired C5 acceptors are less reactive in glycosylation reactions, and trichloroacetimidate donors gave satisfactory results.

It is noted that the glycosylation reaction using thioglycoside donors such as (S)-15 and (R)-16 (see, Scheme 2 above) as donors, may be afforded in the presence of various glycosylation reagents including N-iodosucinimide (NIS) and trifloromethane sulfonic acid (HOTf); or NIS and silver triflate (AgOTf).

Therefore, the thioglycosides Compounds (S)-15 and (R)-16 were converted to the corresponding trichloroacetimidates Compounds (S)-17 and (R)-18 in two successive steps; hydrolysis with NBS in aqueous acetone and treatment of the resulted hemiacetals with CCl₃CN in the presence of DBU. The donors Compounds (S)-17 and (R)-18 were used in glycosylation reactions without further purification.

The synthesis of the exemplary pseudo-trisaccharides compounds, NB118, NB119, NB122 and NB123, was accomplished from the corresponding selectively protected pseudo-disaccharide acceptors Compounds 19 and 20, as previously reported (WO 2007/113841), and the donors Compounds (S)-17 and (R)-18, by using essentially the same chemical transformations, as illustrated in Scheme 3 below (wherein "a" represents BF₃.Et₂O, DCM, 4 Å MS, −20° C.; "b" represents MeNH₂-EtOH, room temperature; and "c" represents PMe₃, NaOH, THF, room temperature).

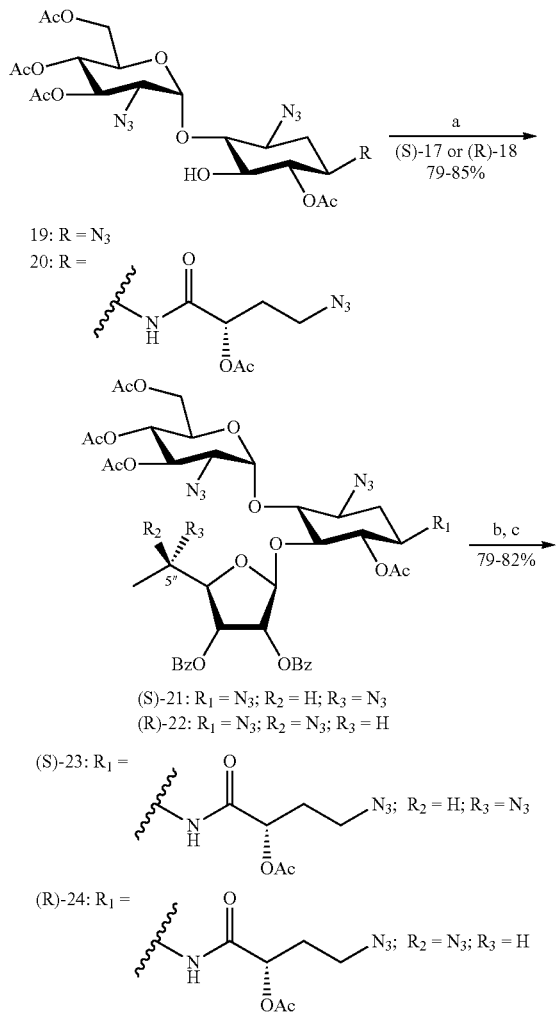

Lewis acid (BF₃.Et₂O/DCM) promoted glycosylation furnished the protected pseudo-trisaccharides Compounds 21-24 in 79-85% isolated yields, exclusively as beta-anomers at the newly generated glycosidic linkage. Two sequential deprotection steps: treatment with methylamine to remove all the ester protection, and the Staudinger reaction (Me₃P, THF/NaOH) to convert azides to corresponding amines, then afforded the target compounds NB118, NB119, NB122 and NB123 in 79-82% isolated yields for two steps.

The structures of all exemplary compounds NB118, NB119, NB122, NB123, NB124, NB125, NB127 and NB128 were confirmed by a combination of various 1D and 2D NMR techniques, including 2D $^1$H-$^{13}$C HMQC and HMBC, 2D COSY, and 1D selective TOCSY experiments, along with mass spectral analysis (see ESM).

FIG. 1A-C present the synthesis plan of C5-diasteromeric esters (R,X)-27 and (S,X)-28, reagents and conditions, wherein "a" represents DCC, 4-DMAP, CSA, DCM, at room temperature (FIG. 1A); $^1$H NMR spectra of (R,X)-27 and (S,X)-28, wherein the chemical shift differences ( ) between particular protons of (R,X)-27 and (S,X)-28 are highlighted (FIG. 1B); and assignment of absolute configuration at the 5-carbon (denoted by X) of the major alcohol Compound 9 by Sector rule (FIG. 1C).

For the assignment of the stereochemistry at the side-chain C5-alcohols in Compounds 9 and 10 (see, Scheme 2), the major product Compound 9 was separately coupled (using DCC, 4-DMAP, CSA) with (R)-2-methoxy-2(1-naphthyl) propanoic acid (R)-MαNP and (S)-MαNP of known absolute stereochemistry, to afford the corresponding esters (R,X)-MαNP-27 and (S,X)-MαNP-28 (see, FIG. 1A), according to previously reported procedure. The absolute configuration at the C5-position (denoted by X) was then determined by using $^1$H NMR anisotropy method (FIG. 1B-C): the chemical shift difference [Δδ=δ(R, X)−δ(S, X)] for H-3 (−0.15) and H-4 (−0.30) was negative, while that for H-6 (+0.28) was positive. An arrangement of the structures (R,X)-MαNP-27 and (S,X)-MαNP-28 according to the Sector rule (see, FIG. 1C: OMαNP and H-5 are positioned on the front and back, respectively, while the Δδ positive part is on the right side of the MαNP plane and the Δδ negative part is on the left side) then confirmed the R configuration (X═R) of the C5 in Compound 9.

Following similar synthetic procedures and synthetic rational, the synthesis of the pseudo-trisaccharides NB124, NB125, NB127 and NB128 was accomplished (See, Scheme 4 below) from the corresponding selectively protected pseudo-disaccharide acceptors Compounds 219 and 220, as previously reported (WO 2007/113841), and the donors Compounds (S)-17 and (R)-18, by using essentially the same chemical transformations as illustrated in Scheme 3 (wherein "a" represents BF₃.Et₂O, DCM, 4 Å MS, −20° C.; "b" represents MeNH₂-EtOH, room temperature; and "c" represents PMe₃, NaOH, THF, room temperature).

Scheme 4

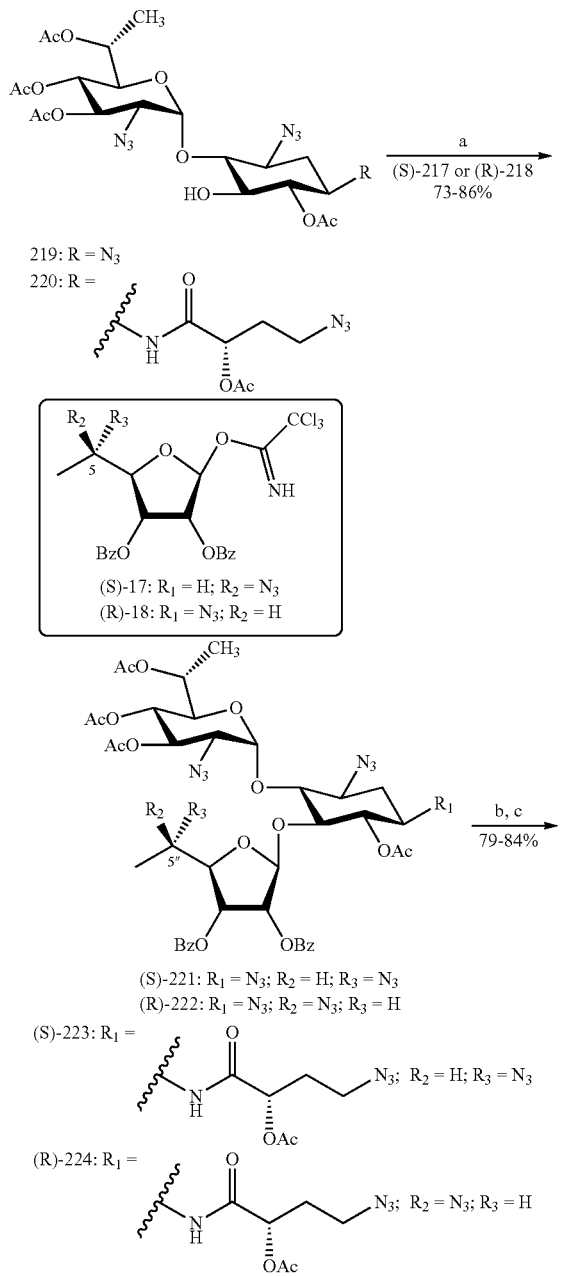

219: R = N₃
220: R = [structure with NH-C(=O)-CH(OAc)-CH₂CH₂-N₃]

(S)-17: R₁ = H; R₂ = N₃
(R)-18: R₁ = N₃; R₂ = H (S)-221: R₁ = N₃; R₂ = H; R₃ = N₃
(R)-222: R₁ = N₃; R₂ = N₃; R₃ = H (S)-223: R₁ = [NH-C(=O)-CH(OAc)-CH₂CH₂-N₃]; R₂ = H; R₃ = N₃

(R)-224: R₁ = [NH-C(=O)-CH(OAc)-CH₂CH₂-N₃]; R₂ = N₃; R₃ = H

NB124
NB125
NB127
NB128

Materials and Methods:

All reactions were carried out under an argon atmosphere with anhydrous solvents, unless otherwise noted.

All chemicals unless otherwise stated, were obtained from commercial sources such as Sigma-Aldrich, Fluka and the likes.

Reactions were monitored by TLC on Silica Gel 60 F$_{254}$ (0.25 mm, Merck), and spots were visualized by charring with a yellow solution containing (NH$_4$)Mo$_7$O$_{24}$·4H$_2$O (120 grams) and (NH$_4$)$_2$Ce(NO$_3$)$_6$ (5 grams) in 10% H$_2$SO$_4$ (800 ml).

Column chromatography was performed on a Silica Gel 60 (70-230 mesh).

1D and 2D NMR spectra were routinely recorded on a Bruker Avance™ 500 spectrometer.

Mass spectra analysis were obtained either on a Bruker Daltonix Apex 3 mass spectrometer under electron spray ionization (ESI), or by a TSQ-70B mass spectrometer (Finnigan Mat).

In all biological tests, all tested aminoglycosides were in their sulfate salt forms. The concentrations reported refer to that of the free amine form of each aminoglycoside.

Preparation of 4-Methylphenyl 2,3-O-1-methylethylidene-1-thio-β-D-ribopentodialdo-1,4-furanoside (Compound 8)

A mixture of 4-methylphenyl 1-thio-β-D-ribofuranoside (Compound 7, 25 grams, 0.097 mol) and 1,1-dimethoxypropane (22.3 ml, 0.39 mol) in acetone (500 ml) was stirred at room temperature for about five minutes and then catalytic amount of CSA (1.0 grams) and MgSO$_4$ (5.0 grams) were added. The reaction progress was monitored by TLC, which indicated completion after 5 hours. The reaction mixture was diluted with ethyl acetate and washed with saturated NaHCO$_3$ and brine. The combined organic layer was dried over MgSO$_4$, evaporated and subjected to column chromatography (EtOAc/Hexane) to afford the desired 2,3-isopropylidene derivative in 82% yield (23.5 grams).

$^1$H NMR (500 MHz, CDCl$_3$): $\delta_H$ 3.73-3.85 (m, 2H, H-5), 4.37 (m, 1H, H-4), 4.74 (dd, 1H, J$_1$=2.5, J$_2$=6.0 Hz, H-2), 4.80 (dd, 1H, J$_1$=1.7, J$_2$=6.0 Hz, H-3), 5.52 (d, 1H, J=2.5 Hz, H-1). Additional peaks in the spectrum were identified as follows: $\delta_H$ 1.37 (s, 3H, isopropylidene-CH$_3$), 1.53 (s, 3H, isopropylidene-CH$_3$), 2.35 (s, 3H, aryl-CH$_3$), 7.16 (d, 2H, J=8.0 Hz), 7.42 (d, 2H, J=8.0 Hz).

$^{13}$C NMR (125 MHz, CDCl$_3$): $\delta_C$ 21.0 (CH$_3$), 25.2 (CH$_3$), 26.8 (CH$_3$), 63.2 (C-5), 81.8 (C-3), 85.7 (C-2), 87.7 (C-4), 93.0 (C-1), 113.3 (quaternary-C), 129.2 (Ar), 129.9 (Ar), 132.3 (Ar), 138.0 (Ar).

MALDI TOFMS calculated for C$_5$H$_{20}$O$_4$SNa ([M+Na]$^+$) m/e 319.1; measured m/e 319.09.

The product the above step (22 grams, 0.074 mol) was stirred in dichloromethane (500 ml) at room temperature to which Dess-Martin periodinane (DMP, 34.6 grams, 0.082 mol) and MgSO$_4$ (5.0 grams) were added. The reaction progress was monitored by TLC, which indicated completion after 8 hours. The reaction mixture was diluted with ether and washed with saturated NaHCO$_3$, Na$_2$S$_2$O$_3$, and brine. The combined organic layer was dried over MgSO$_4$, evaporated and subjected to column chromatography (EtOAc/Hexane) to yield Compound 8 (18.0 grams, 85% yield).

$^1$H NMR (500 MHz, CDCl$_3$): $\delta_H$ 4.49 (s, 1H, H-4), 4.69 (d, 1H, J=6.5 Hz, H-2), 5.21 (d, 1H, J=6.0 Hz, H-3), 5.86 (s, 1H, H-1), 9.80 (s, 1H, H-5, CHO). Additional peaks in the spectrum were identified as follows: $\delta_H$ 1.37 (s, 3H, isopropylidene-CH$_3$), 1.52 (s, 3H, isopropylidene-CH$_3$), 2.36 (s, 3H, Ar—CH$_3$), 7.19 (d, 2H, J=8.0 Hz, Ar), 7.41 (d, 2H, J=8.0 Hz, Ar).

$^{13}$C NMR (125 MHz, CDCl$_3$): $\delta_C$ 21.0 (CH$_3$), 25.1 (CH$_3$), 26.2 (CH$_3$), 87.1 (C-3), 84.5 (C-2), 89.9 (C-4), 92.6 (C-1), 113.3 (quaternary-C), 128.9 (Ar), 130.0 (Ar), 131.0 (Ar), 137.8 (Ar), 200.3 (CHO).

MALDI TOFMS calculated for C$_{15}$H$_{19}$O$_4$S ([M+H]$^+$) m/e 295.1; measured m/e 295.1.

Preparation of 4-Methylphenyl 6-deoxy-2,3-O-1-methylethylidene-1-thio-β-D-allofuranoside (Compound (R)-9) and 4-methylphenyl 6-deoxy-2,3-O-1-methylethylidene-1-thio-α-L-talofuranoside (Compound (S)-10)

The aldehyde Compound 8 (17 grams, 0.057 mol) was stirred in THF (200 ml) at −30° C. for 30 minutes to which the solution of MeMgBr (1.4 M in THF/Toluene, 235 ml, 0.171 mol) was added drop wise with syringe. The reaction mixture was stirred for 2 hours at the same temperature and progress was monitored by TLC.

After completion, the reaction mixture was quenched with saturated NH$_4$Cl and extracted with ethyl acetate. The combined organic layer was dried over MgSO$_4$ and evaporated. The crude product was purified by column chromatography (EtOAc/Hexane) to afford 4:1 ratio of two C5-diastereomers in 88% yield: the major product Compound (5R)-9 (13 grams, R$_f$=0.38 in EtOAc/Hexane 1:4) and the minor product Compound (5S)-10 (3 grams, R$_f$=0.48 in EtOAc/Hexane 1:4). The absolute configuration at the C5-position was determined by using $^1$H NMR anisotropy method as described below.

Data for Compound (5R)-9:
[α]$_D^{20}$=−191.4 (c=1.02, CHCl$_3$). $^1$H NMR (500 MHz, CDCl$_3$): δ$_H$ 1.25 (d, 3H, J=6.3 Hz, CH$_3$), 4.06 (m, 2H, H-4 and H-5), 4.68 (dd, 1H, J$_1$=2.8, J$_2$=6.3 Hz, H-2), 4.87 (t, 1H, J=5.0 Hz, H-3), 5.46 (d, 1H, J=2.8 Hz, H-1). Additional peaks in the spectrum were identified as follows: δ$_H$ 1.37 (s, 3H, isopropylidene-CH$_3$), 1.53 (s, 3H, isopropylidene-CH$_3$), 2.34 (s, 3H, Ar—CH$_3$), 7.15 (d, 2H, J=8.0 Hz, Ar), 7.42 (d, 2H, J=8.0 Hz, Ar).
$^{13}$CNMR (125 MHz, CDCl$_3$): δ$_C$ 18.5 (C-6), 21.0 (CH$_3$), 25.2 (CH$_3$), 26.9 (CH$_3$), 67.3 (C-5), 80.2 (C-3), 85.4 (C-2), 91.4 (C-4), 92.5 (C-1), 113.4 (quaternary-C), 129.2 (Ar), 129.8 (Ar), 132.3 (Ar), 137.9 (Ar).
MALDI TOFMS calculated for C$_{16}$H$_{22}$O$_4$SNa ([M+Na]$^+$) m/e 333.1; measured m/e 333.1.

Data for Compound (5S)-10:
[α]$_D^{20}$=−199.7 (c=1.04, CHCl$_3$). $^1$H NMR (500 MHz, CDCl$_3$): δ$_H$ 1.27 (d, 3H, J=6.3 Hz, CH$_3$), 3.90 (m, 1H, H-5), 4.08 (dd, 1H, J$_1$=1.3, J$_2$=5.6 Hz, H-4), 4.71 (dd, 1H, J$_1$=1.3, J$_2$=6.0 Hz, H-3), 4.76 (dd, 1H, J=2.1, J$_2$=6.0 Hz, H-2), 5.57 (d, 1H, J=2.0 Hz, H-1). Additional peaks in the spectrum were identified as follows: δ$_H$ 1.36 (s, 3H, isopropylidene-CH$_3$), 1.54 (s, 3H, isopropylidene-CH$_3$), 2.35 (s, 3H, Ar—CH$_3$), 7.17 (d, 2H, J=8.0 Hz, Ar), 7.43 (d, 2H, J=8.0 Hz, Ar).
$^{13}$C NMR (125 MHz, CDCl$_3$): δ$_C$ 19.2 (C-6), 21.0 (CH$_3$), 25.2 (CH$_3$), 26.8 (CH$_3$), 67.9 (C-5), 82.4 (C-3), 85.7 (C-2), 91.6 (C-4), 93.0 (C-1), 113.3 (quaternary-C), 129.4 (Ar), 129.9 (Ar), 131.9 (Ar), 137.9 (Ar).
MALDI TOFMS calculated for C$_{16}$H$_{22}$O$_4$SNa ([M+Na]$^+$) m/e 333.1; measured m/e 333.1.

Preparation of Esters Compound (R,X)-27 and Compound (S,X)-28 for the Assignment of Absolute Configuration at C5

A mixture of (R)-2-methoxy-2(1-naphthyl)propanoic acid [(R)-MαNP] or (S)-MαNP (0.07 grams, 0.0003 mol), 4-dimethylaminopyridine (DMAP, 0.05 grams, 0.0004 mol), 10-camphorsulfonic acid (CSA, 0.025 grams), and 1,3-dicyclohexylcarbodiimide (DCC, 0.240 grams, 0.0016 mol) was stirred in CH$_2$Cl$_2$ (30 ml) at 0° C. The major alcohol 9 from the above (0.1 grams, 0.0003 mol), was dissolved in CH$_2$Cl$_2$ (5 ml), slowly added to the above stirred mixture, and the reaction was left at room temperature for overnight. The mixture was diluted with EtOAc and washed with 1% HCl solution, saturated NaHCO$_3$ and brine. The combined organic layer was dried over MgSO$_4$, evaporated and subjected to a column chromatography (EtOAc/Hexane) to yield the desired esters Compound (R,X)-27 (0.135 grams, 80%) or Compound (S,X)-28 (0.138 grams, 80%).

Data for Compound (R,X)-27:
$^1$H NMR (500 MHz, CDCl$_3$): δ$_H$ 1.23 (d, 3H, J=6.3 Hz, CH$_3$), 3.54 (d, 1H, J=6.1 Hz, H-3), 3.72 (d, 1H, J=9.0 Hz, H-4), 4.18 (dd, 1H, J$_1$=2.3, J$_2$=6.1 Hz, H-2), 5.08 (m, 1H, H-5), 5.32 (d, 1H, J=2.4 Hz, H-1). Additional peaks in the spectrum were identified as follows: δ$_H$ 1.00 (s, 3H, isopropylidene-CH$_3$), 1.32 (s, 3H, isopropylidene-CH$_3$), 2.04 (s, 3H, CH$_3$), 2.32 (s, 3H, Ar—CH$_3$), 3.14 (s, 3H, OCH$_3$), 7.11 (d, 2H, J=8.0 Hz, Ar), 7.28-7.31 (m, 2H, Ar), 7.48-7.56 (m, 3H, Ar), 7.65 (d, 1H, J=8.0 Hz, Ar), 7.85 (dd, 2H, J$_1$=4.7, J$_2$=8.0 Hz, Ar), 8.47 (d, 1H, J=8.0 Hz, Ar).
$^{13}$C NMR (125 MHz, CDCl$_3$): δ$_C$ 17.1 (C-6), 21.0 (CH$_3$), 21.5 (CH$_3$), 24.8 (CH$_3$), 26.6 (CH$_3$), 50.9 (OCH$_3$), 70.5 (C-5), 81.2 (C-3), 81.3 (quaternary-C), 84.8 (C-2), 88.0 (C-4), 92.5 (C-1), 112.9 (quaternary-C), 124.7 (Ar), 125.0 (Ar), 125.7 (Ar), 125.8 (Ar), 126.6 (Ar), 128.8 (Ar), 129.5 (Ar), 129.7 (Ar), 130.3 (Ar), 131.2 (Ar), 131.3 (Ar), 134.0 (Ar), 134.6 (Ar), 137.2 (Ar), 173.1 (C=O).
MALDI TOFMS calculated for C$_{30}$H$_{34}$O$_6$SNa ([M+Na]$^+$) m/e 545.2; measured m/e 545.2.

Data for Compound (S,X)-28:
$^1$H NMR (500 MHz, CDCl$_3$): δ$_C$ 0.95 (d, 3H, J=6.3 Hz, CH$_3$), 3.84 (dd, 1H, J$_1$=1.5, J$_2$=6.2 Hz, H-3), 3.87 (dd, 1H, J$_1$=1.5 and J$_2$=6.2 Hz, H-4), 4.08 (dd, 1H, J$_1$=3.4, J$_2$=6.1 Hz, H-2), 5.06 (m, 1H, H-5), 5.27 (d, 1H, J=3.4 Hz, H-1). Additional peaks in the spectrum were identified as follows: δ$_H$ 1.14 (s, 3H, isopropylidene-CH$_3$), 1.41 (s, 3H, isopropylidene-CH$_3$), 2.09 (s, 3H, CH$_3$), 2.33 (s, 3H, Ar—CH$_3$), 3.14 (s, 3H, OCH$_3$), 7.12 (d, 2H, J=8.0 Hz, Ar), 7.35 (d, 2H, J=8.0 Hz, Ar), 7.49-7.67 (m, 3H, Ar), 7.69 (d, 1H, J=8.0 Hz, Ar), 7.88 (d, 2H, J=8.0 Hz, Ar), 8.41 (d, 1H, J=8.0 Hz, Ar).
$^{13}$C NMR (125 MHz, CDCl$_3$): δ$_C$ 16.0 (C-6), 21.0 (CH$_3$), 21.5 (CH$_3$), 24.9 (CH$_3$), 26.8 (CH$_3$), 50.8 (OCH$_3$), 71.4 (C-5), 81.0 (C-3), 81.5 (quaternary-C), 84.7 (C-2), 87.5 (C-4), 92.6 (C-1), 113.3 (quaternary-C), 124.7 (Ar), 125.2 (Ar), 125.7 (Ar), 126.0 (Ar), 126.4 (Ar), 128.6 (Ar), 129.4 (Ar), 129.7 (Ar), 130.3 (Ar), 131.3 (Ar), 131.5 (Ar), 133.8 (Ar), 134.8 (Ar), 137.4 (Ar), 173.4 (C=O).
MALDI TOFMS calculated for C$_{30}$H$_{34}$O$_6$SNa ([M+Na]$^+$) m/e 545.2; measured m/e 545.2.

Preparation of 4-Methylphenyl 6-deoxy-5-O-tosyl-2,3-O-1-methylethylidene-1-thio-β-D-allofuranoside (Compound (R)-11)

To a stirred solution of Compound (R)-9 (13 grams, 0.041 mol) in pyridine (200 ml) at 0° C., were added tosyl chloride (15.6 grams, 0.082 mol) and 4-DMAP (1 gram). The reaction temperature was raised to room temperature and progress was monitored by TLC. After completion (36 hours), the reaction mixture was diluted with ethyl acetate and sequentially washed with 1% aqueous HCl solution, saturated NaHCO$_3$, and brine. The combined organic layer was dried over MgSO$_4$, evaporated and subjected to column chromatography (EtOAc/Hexane) to obtain Compound (R)-11 (16.0 grams) in 82% yield.

$^1$H NMR (500 MHz, CDCl$_3$): δ$_H$ 1.28 (d, 3H, J=6.2 Hz, CH$_3$), 3.99 (d, 1H, J=8.6 Hz, H-4), 4.60 (dd, 1H, J$_1$=2.0, J$_2$=6.2 Hz, H-2), 4.67 (d, 1H, J=6.2 Hz, H-3), 4.92 (m, 1H, H-5), 5.48 (d, 1H, J=1.8 Hz, H-1). Additional peaks in the spectrum were identified as follows: δ$_H$ 1.30 (s, 3H, isopropylidene-CH$_3$), 1.48 (s, 3H, isopropylidene-CH$_3$), 2.34 (s, 3H, Ar—CH$_3$), 2.45 (s, 3H, Ar—CH$_3$) 7.13 (d, 2H, J=8.0 Hz, Ar), 7.30-7.38 (m, 4H, Ar), 7.87 (d, 2H, J=8.0 Hz, Ar).

$^{13}$C NMR (125 MHz, CDCl$_3$): δ$_C$ 18.0 (C-6), 21.0 (CH$_3$), 21.6 (CH$_3$), 25.0 (CH$_3$), 26.6 (CH$_3$), 77.1 (C-5), 81.2 (C-3), 85.0 (C-2), 87.9 (C-4), 92.3 (C-1), 113.6 (quaternary-C), 127.9 (Ar), 129.8 (2C, Ar), 129.9 (Ar), 131.0 (Ar), 133.8 (Ar), 137.4 (Ar), 144.8 (Ar).

MALDI TOFMS calculated for C$_{23}$H$_{29}$O$_6$S$_2$ ([M+H]$^+$) m/e 465.1; measured m/e 465.1.

Preparation of 4-Methylphenyl 6-deoxy-5-O-tosyl-2,3-O-1-methylethylidene-1-thio-α-L-alofuranoside (Compound (S)-12)

To a stirred solution of Compound (S)-10 (10 grams, 0.032 mol) in pyridine (200 ml) at 0° C., were added tosyl chloride (15.6 grams, 0.082 mol) and 4-DMAP (1 gram). The reaction temperature was raised to room temperature and progress was monitored by TLC. After completion (36 hours), the reaction mixture was diluted with ethyl acetate and sequentially washed with 1% aqueous HCl solution, saturated NaHCO$_3$, and brine. The combined organic layer was dried over MgSO$_4$, evaporated and subjected to column chromatography (EtOAc/Hexane) to obtain Compound (S)-12 (14.0 grams) in 88% yield.

$^1$HNMR (500 MHz, CDCl$_3$): δ$_H$ 1.37 (d, 3H, J=6.4 Hz, CH$_3$), 4.09 (dd, 1H, J$_1$=2.8, J$_2$=4.3 Hz, H-4), 4.48 (dd, 1H, J=2.8, J$_2$=6.2 Hz, H-3), 4.55 (dd, 1H, J=4.0, J$_2$=6.2 Hz, H-2), 4.82 (m, 1H, H-5), 5.25 (d, 1H, J=4.0 Hz, H-1). Additional peaks in the spectrum were identified as follows: δ$_H$ 1.30 (s, 3H, isopropylidene-CH$_3$), 1.50 (s, 3H, isopropylidene-CH$_3$), 2.35 (s, 3H, Ar—CH$_3$), 2.43 (s, 3H, Ar—CH$_3$) 7.12 (d, 2H, J=8.0 Hz, Ar), 7.32 (d, 2H, J=8.0 Hz, Ar), 7.38 (d, 2H, J=8.0 Hz, Ar), 7.87 (d, 2H, J=8.0 Hz, Ar).

$^{13}$CNMR (125 MHz, CDCl$_3$): δc 17.0 (C-6), 21.0 (Ar—CH$_3$), 21.6 (Ar—CH$_3$), 25.3 (isopropylidene —CH$_3$), 27.2 (isopropylidene —CH$_3$), 78.3 (C-5), 81.2 (C-3), 84.6 (C-2), 86.7 (C-4), 92.2 (C-1), 114.1 (quaternary-C), 127.7 (Ar), 129.6 (Ar), 129.7 (Ar), 129.8 (Ar), 132.3 (Ar), 134.1 (Ar), 137.6 (Ar), 144.7 (Ar).

MALDI TOFMS calculated for C$_{23}$H$_{28}$O$_6$S$_2$Na ([M+Na]$^+$) m/e: 487.1; measured m/e: 487.1

Preparation of 4-Methylphenyl 5-azido-5,6-dideoxy-2,3-O-1-methylethylidene-1-thio-α-L-talofuranoside (Compound (S)-13)

To a stirred solution of Compound (R)-11 (15 grams, 0.032 mol) in DMF (250 ml) were added NaN$_3$ (10 grams, 0.15 mol) and HMPA (15 ml) at room temperature. The reaction temperature was raised to 70° C. and progress was monitored by TLC. After completion (10 hours), the reaction mixture was diluted with ethyl acetate and sequentially washed with 1% aqueous HCl solution, saturated NaHCO$_3$, and brine. The combined organic layer was dried over MgSO$_4$, evaporated and subjected to column chromatography (EtOAc/Hexane) to obtain Compound (S)-13 (6 grams) in 55% yield.

$^1$HNMR (500 MHz, CDCl$_3$): δ$_H$ 1.35 (d, 3H, J=6.2 Hz, CH$_3$), 3.73 (m, 1H, H-5), 3.99 (dd, 1H, J$_1$=3.0, J$_2$=6.7 Hz, H-4), 4.56 (dd, 1H, J$_1$=3.0, J$_2$=6.5 Hz, H-3), 4.70 (dd, 1H, J$_1$=2.0, J$_2$=6.2 Hz, H-2), 5.39 (d, 1H, J=3.2 Hz, H-1). Additional peaks in the spectrum were identified as follows: δ$_H$ 1.36 (s, 3H, isopropylidene-CH$_3$), 1.53 (s, 3H, isopropylidene-CH$_3$), 2.36 (s, 3H, Ar—CH$_3$), 7.15 (d, 2H, J=8.0 Hz, Ar), 7.46 (d, 2H, J=8.0 Hz, Ar).

$^{13}$CNMR (125 MHz, CDCl$_3$): δ$_C$ 15.5 (C-6), 21.1 (Ar—CH$_3$), 25.4 (isopropylidene-CH$_3$), 27.1 (isopropylidene-CH$_3$), 58.2 (C-5), 81.9 (C-3), 85.1 (C-2), 88.9 (C-4), 91.9 (C-1), 114.2 (quaternary-C), 129.5 (Ar), 129.7 (Ar), 132.4 (Ar), 138.8 (Ar).

MALDI TOFMS calculated for C$_{16}$H$_{20}$N$_3$O$_3$S ([M−H]$^-$) m/e: 334.1; measured m/e: 334.1.

Preparation of 4-Methylphenyl 5-azido-5,6-dideoxy-2,3-O-1-methylethylidene-1-thio-β-D-allofuranoside (Compound (R)-14)

To a stirred solution of Compound (S)-12 (13 grams, 0.028 mol) in DMF (250 ml) were added NaN$_3$ (10 grams, 0.15 mol) and HMPA (13 ml) at room temperature. The reaction temperature was raised to 70° C. and progress was monitored by TLC. After completion (10 hours), the reaction mixture was diluted with ethyl acetate and sequentially washed with 1% aqueous HCl solution, saturated NaHCO$_3$, and brine. The combined organic layer was dried over MgSO$_4$, evaporated and subjected to column chromatography (EtOAc/Hexane) to obtain Compound (R)-14 (9 grams) in 97% yield.

$^1$HNMR (500 MHz, CDCl$_3$): δ$_H$ 1.32 (d, 3H, J=6.2 Hz, CH$_3$), 3.81 (m, 1H, H-5), 3.89 (dd, 1H, J$_1$=2.1, J$_2$=8.3 Hz, H-4), 4.72 (dd, 1H, J$_1$=2.5, J$_2$=6.3 Hz, H-2), 4.77 (dd, 1H, J$_1$=2.1, J$_2$=6.3 Hz, H-3), 5.49 (d, 1H, J=2.5 Hz, H-1). Additional peaks in the spectrum were identified as follows: δ$_H$ 1.37 (s, 3H, isopropylidene-CH$_3$), 1.53 (s, 3H, isopropylidene-CH$_3$), 2.35 (s, 3H, Ar—CH$_3$), 7.15 (d, 2H, J=8.0 Hz, Ar), 7.74 (d, 2H, J=8.0 Hz, Ar).

$^{13}$CNMR (125 MHz, CDCl$_3$): δ$_C$ 16.2 (C-6), 21.0 (Ar—CH$_3$), 25.2 (isopropylidene-CH$_3$), 26.1 (isopropylidene-CH$_3$), 58.1 (C-5), 81.9 (C-3), 85.1 (C-2), 89.1 (C-4), 92.2 (C-1), 113.8 (quaternary-C), 129.7 (Ar), 129.8 (Ar), 131.6 (Ar), 137.6 (Ar).

MALDI TOFMS calculated for C$_{16}$H$_{20}$N$_3$O$_3$S ([M−H]$^-$) m/e: 334.1; measured m/e: 334.1.

Preparation of 4-Methylphenyl 5-azido-5,6-dideoxy-2,3-O-dibenzoyl-1-thio-α-L-talofuranoside (Compound (S)-15)

Compound (S)-13 (6 grams, 0.018 mol) was stirred in a mixture of acetic acid-water (100 ml, 8:2) at 70° C. for overnight. The reaction progress was monitored by TLC, after completion, the reaction mixture was diluted with ethyl acetate and washed with saturated NaHCO$_3$ and brine. The combined organic layer was dried over MgSO$_4$, evaporated and subjected to column chromatography (EtOAc/Hexane) to obtain desired isopropylidene deprotected product (5 grams) in 96% yield.

$^1$HNMR (500 MHz, CDCl$_3$): δ$_H$ 1.36 (d, 3H, J=6.2 Hz, CH$_3$), 3.61 (m, 1H, H-5), 3.82 (t, 1H, J=4.8 Hz, H-4), 4.13 (m, 2H, H-3 and H-2), 5.18 (d, 1H, J=3.7 Hz, H-1). Additional peaks in the spectrum were identified as follows: δ$_H$ 2.35 (s, 3H, Ar—CH$_3$), 7.15 (d, 2H, J=8.0 Hz, Ar), 7.45 (d, 2H, J=8.0 Hz, Ar).

$^{13}$CNMR (125 MHz, CDCl$_3$): δ$_C$ 15.2 (C-6), 21.0 (Ar—CH$_3$), 58.2 (C-5), 72.0 (C-3), 74.9 (C-2), 86.5 (C-4), 90.5 (C-1), 128.8 (Ar), 129.7 (Ar), 133.0 (Ar), 138.1 (Ar).

MALDI TOFMS calculated for C$_{13}$H$_{16}$N$_3$O$_3$S ([M−H]$^-$) m/e: 294.1; measured m/e: 294.08.

The product of the above step was stirred in pyridine (200 ml) at 0° C. to which BzCl (7.14 grams, 0.051) and 4-DMAP (1 gram) was added slowly. The reaction temperature was raised to room temperature and stirred for overnight. The reaction progress was monitored by TLC, after completion, reaction mixture was diluted with ethyl acetate and washed with 1% HCl solution, saturated NaHCO$_3$ and brine. The combined organic layer was dried over MgSO$_4$, evaporated and subjected to column chromatography (EtOAc/Hexane) to obtain Compound (S)-15 (8.0 grams) in 94% yield.

$^1$HNMR (500 MHz, CDCl$_3$): δ$_H$ 1.38 (d, 3H, J=6.2 Hz, CH$_3$), 3.81 (m, 1H, H-5), 4.22 (m, 1H, H-4), 5.55 (m, 1H, H-1), 5.56-5.58 (m, 2H, H-2 and H-3). Additional peaks in the spectrum were identified as follows: δ$_H$ 2.37 (s, 3H, Ar—CH$_3$), 7.21 (d, 2H, J=8.0 Hz, Ar), 7.34-7.42 (m, 4H, Ar), 7.53-7.59 (m, 4H, Ar), 7.90 (dd, 2H, J$_1$=1.2, J$_2$=8.0 Hz, Ar), 7.99 (dd, 2H, J$_1$=1.2, J$_2$=8.0 Hz, Ar).

$^{13}$CNMR (125 MHz, CDCl$_3$): δ$_C$ 15.2 (C-6), 21.1 (Ar—CH$_3$), 57.9 (C-5), 72.6 (C-3), 74.4 (C-2), 85.1 (C-4), 88.4 (C-1), 127.8 (Ar), 128.3 (2C, Ar), 128.9 (Ar), 129.0 (Ar), 129.6 (Ar), 129.7 (Ar), 129.8 (Ar), 133.4 (2C, Ar), 133.9 (Ar), 138.6 (Ar), 164.9 (C=O), 165.2 (C=O).

MALDI TOFMS calculated for C$_{27}$H$_{25}$N$_3$O$_5$SNa ([M+Na]$^+$) m/e: 526.2; measured m/e: 526.1.

Preparation of 4-Methylphenyl 5-azido-5,6-dideoxy-2,3-O-dibenzoyl-1-thio-β-D-allofuranoside (Compound (R)-16)

Compound (R)-14 (8 grams, 0.023 mol) was stirred in a mixture of acetic acid-water (100 ml, 8:2) at 70° C. for over night. The reaction progress was monitored by TLC, after completion, the reaction mixture was diluted with ethyl acetate and washed with saturated NaHCO$_3$ and brine. The combined organic layer was dried over MgSO$_4$, evaporated and subjected to column chromatography (EtOAc/Hexane) to obtain the desired isopropylidene deprotected product (6.5 grams) in 92% yield.

$^1$HNMR (500 MHz, CDCl$_3$): δ$_H$ 1.36 (d, 3H, J=6.2 Hz, CH$_3$), 3.65 (m, 1H, H-5), 3.78 (dd, 1H, J$_1$=2.5, J$_2$=7.5 Hz, H-4), 4.09 (t, 1H, J=5.0 Hz, H-2), 4.15 (t, 1H, J=4.5 Hz, H-3), 5.18 (d, 1H, J=5.0 Hz, H-1). Additional peaks in the spectrum were identified as follows: δ$_H$ 2.36 (s, 3H, Ar—CH$_3$), 7.15 (d, 2H, J=8.0 Hz, Ar), 7.44 (d, 2H, J=8.0 Hz, Ar).

$^{13}$CNMR (125 MHz, CDCl$_3$): δ$_C$ 16.0 (C-6), 21.0 (Ar—CH$_3$), 59.0 (C-5), 71.9 (C-3), 74.9 (C-2), 86.4 (C-4), 90.3 (C-1), 128.9 (Ar), 129.7 (Ar), 132.8 (Ar), 138.1 (Ar).

MALDI TOFMS calculated for C$_{13}$H$_{16}$N$_3$O$_3$S ([M−H]$^−$) m/e: 294.1; measured m/e: 294.08.

The product from the above step was stirred in pyridine (200 ml) at 0° C. to which BzCl (7.14 grams, 0.051) and 4-DMAP (1 gram) was added slowly. The reaction temperature was raised to room temperature and stirred for overnight. The reaction progress was monitored by TLC, after completion, reaction mixture was diluted with ethyl acetate and washed with 1% HCl solution, saturated NaHCO$_3$ and brine. The combined organic layer was dried over MgSO$_4$, evaporated and subjected to column chromatography (EtOAc/Hexane) to obtain Compound (R)-16 (9.5 grams) in 93% yield.

$^1$HNMR (500 MHz, CDCl$_3$): δ$_H$ 1.42 (d, 3H, J=6.7 Hz, CH$_3$), 3.74 (m, 1H, H-5), 4.24 (t, 1H, J=4.7 Hz, H-4), 5.53 (d, 1H, J=5.6 Hz, H-1), 5.50 (t, 1H, J=5.5 Hz, H-2), 5.65 (t, 1H, J=5.5 Hz, H-3). Additional peaks in the spectrum were identified as follows: δ$_H$ 2.38 (s, 3H, Ar—CH$_3$), 7.20 (d, 2H, J=8.0 Hz, Ar), 7.38 (t, 4H, J=7.6 Hz, Ar), 7.51 (d, 2H, J=8.0 Hz, Ar), 7.55 (t, 2H, J=8.0 Hz, Ar), 7.93-7.96 (m, 4H, Ar).

$^{13}$CNMR (125 MHz, CDCl$_3$): δ$_C$ 15.5 (C-6), 21.1 (Ar—CH$_3$), 58.5 (C-5), 71.8 (C-3), 74.2 (C-2), 84.9 (C-4), 88.2 (C-1), 127.8 (Ar), 128.3 (2C, Ar), 128.9 (2C, Ar), 129.6 (Ar), 129.7 (Ar), 129.8 (Ar), 133.3 (2C, Ar), 133.8 (Ar), 138.6 (Ar), 164.9 (C=O), 165.0 (C=O).

MALDI TOFMS calculated for C$_{27}$H$_{25}$N$_3$O$_5$SNa ([M+Na]$^+$) m/e: 526.2; measured m/e: 526.2.

Preparation of L-Talofuranose, 5-azido-5,6-dideoxy-2,3-dibenzoate 1-(2,2,2-trichloroethanimidate) (Compound (S)-17)

Compound (S)-15 (8 grams, 0.016 mol) was stirred in a mixture of acetone-water (100 ml, 9:1) mixture at −30° C. for 10 minutes to which N-bromosuccinimide (9.16 grams, 0.051 mol) was added slowly. The reaction mixture was stirred at same temperature and the progress was monitored by TLC. After completion (3 hours), reaction mixture was diluted with ethyl acetate and washed saturated NaHCO$_3$, saturated Na$_2$S$_2$O$_3$ and brine. The combined organic layer was dried over MgSO$_4$, evaporated to obtain 6.3 grams of corresponding hemiacetal. The hemiacetal was stirred in a mixture of dichloromethane (40 ml) and trichloroacetonitrile (5 ml) at 0° C. for 10 minutes to which catalytic amount of DBU (0.3 ml) was added. The reaction mixture was stirred in same temperature and the progress was monitored by TLC. After completion (3 hours), the reaction mixture was diluted with DCM and washed with saturated NH$_4$Cl. The combined organic layer was dried over MgSO$_4$ and concentrated to obtain Compound (S)-17 (9 grams). The crude product was directly used for the glycosylation reaction without purification.

Preparation of D-Allofuranose, 5-azido-5,6-dideoxy-2,3-dibenzoate 1-(2,2,2-trichloroethanimidate) (Compound (R)-18)

Compound (R)-16 (9 grams, 0.018 mol) was stirred in a mixture of acetone-water (100 ml, 9:1) mixture at −30° C. for 10 minutes to which N-bromosuccinimide (9.0 grams, 0.050 mol) was added slowly. The reaction mixture was stirred at same temperature and the progress was monitored by TLC. After completion (3 hours), reaction mixture was diluted with ethyl acetate and washed saturated NaHCO$_3$, saturated Na$_2$S$_2$O$_3$ and brine. The combined organic layer was dried over MgSO$_4$, evaporated to obtain 6.5 grams of corresponding hemiacetal. The hemiacetal was stirred in a mixture of dichloromethane (50 ml) and trichloroacetonitrile (6 ml) at 0° C. for 10 minutes to which catalytic amount of DBU (0.3 ml) was added. The reaction mixture was stirred in same temperature and the progress was monitored by TLC. After completion (3 hours), the reaction mixture was diluted with DCM and washed with saturated NH$_4$Cl. The combined organic layer was dried over MgSO$_4$ and concentrated to obtain Compound (R)-18 (9 grams). The crude product was directly used for the glycosylation reaction without purification.

Preparation of 5-O-(5-Azido-5,6-dideoxy-2,3-O-dibenzoyl-α-L-talofuranosyl)-3',4',6',6-tetra-O-acetyl-2',1,3-triazido paromamine (Compound (S)-21)

Anhydrous CH$_2$Cl$_2$ (15 ml) was added to a powdered, flame-dried 4 Å molecular sieves (2.0 grams), followed by the addition acceptor Compound 19 (0.75 grams, 0.0013 mol) and donor Compound (S)-17 (2.1 grams, 0.0039 mol). The reaction mixture was stirred for 10 min at room temperature and was then cooled to −20° C. A catalytic amount of BF$_3$-Et$_2$O (0.1 ml) was added and the mixture was stirred at −15° C. and the reaction progress was monitored by TLC, which indicated the completion after 60 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain Compound (S)-21 (1.0 grams) in 80% yield.

$^1$HNMR (500 MHz, CDCl$_3$): "Ring I" δ$_H$ 3.65 (dd, 1H, J$_1$=4.2, J$_2$=9.7 Hz, H-2'), 4.20 (d, 1H, J=11.1 Hz, H-6'), 4.26 (dd, 1H, J$_1$=3.1, J$_2$=12.6 Hz, H-6'), 4.54 (m, 1H, H-5'), 5.08 (dd, 1H, J$_1$=9.3, J$_2$=10.7 Hz, H-4'), 5.41 (t, 1H, J=9.9 Hz, H-3'), 5.85 (d, 1H, J=3.7 Hz, H-1'); "Ring II" δ$_H$ 1.64 (ddd, 1H, J$_1$=J$_2$=J$_3$=12.5 Hz, H-2$_{ax}$), 2.42 (td, 1H, J$_1$=4.5, J$_2$=12.5 Hz, H-2$_{eq}$), 3.49-3.56 (m, 2H, H-1 and H-3), 3.74 (t, 1H, J=9.5 Hz, H-4), 3.87 (t, 1H, J=8.7 Hz, H-5), 5.02 (d, 1H, J=10.1 Hz, H-6); "Ring III" δ$_H$ 1.27 (d, 3H, J=6.9 Hz, CH$_3$), 3.72 (m, 1H, H-5"), 4.35 (t, 1H, J=6.6 Hz, H-4"), 5.43 (dd, 1H, J$_1$=5.1, J$_2$=7.4 Hz, H-3"), 5.62 (d, 1H, J=3.8 Hz, H-2"), 5.66 (s, 1H, H-1"). Additional peaks in the spectrum were identified as follows: δ$_H$ 2.04 (s, 3H, OAc), 2.10 (s, 3H, OAc), 2.11 (s, 3H, OAc), 2.23 (s, 3H, OAc), 7.35-7.43 (m, 4H, Ar), 7.53-7.60 (m, 2H, Ar), 7.89-7.95 (m, 4H, Ar).

$^{13}$CNMR (125 MHz, CDCl$_3$): δ$_C$ 15.3 (C-6"), 20.5 (OAc), 20.6 (2C, OAc), 20.9 (OAc), 31.6 (C-1), 58.3, 58.5, 59.3, 61.7, 61.8, 68.0, 68.2, 70.9, 71.8, 73.6, 74.6, 78.1, 79.5, 84.4, 96.6 (C-1'), 107.6 (C-1"), 128.4 (Ar), 128.5 (2C, Ar), 128.7 (Ar), 129.6 (2C, Ar), 133.5 (Ar), 133.6 (Ar), 164.8 (C=O), 165.3 (C=O), 169.7 (C=O), 169.9 (C=O), 170.1 (C=O), 170.6 (C=O).

MALDI TOFMS calculated for C$_{40}$H$_{43}$N$_{12}$O$_{16}$ ([M−H]$^−$) m/e: 947.3; measured m/e: 947.28.

Preparation of 5-O-(5-Azido-5,6-dideoxy-2,3-O-dibenzoyl-β-D-allofuranosyl)-3',4',6',6-tetra-O-acetyl-2',1,3-triazido paromamine (Compound (R)-22)

Anhydrous CH$_2$Cl$_2$ (15 ml) was added to a powdered, flame-dried 4 Å molecular sieves (2.0 grams), followed by the addition acceptor Compound 19 (0.75 grams, 0.0013 mol) and donor Compound (R)-18 (2.1 grams, 0.0039 mol). The reaction mixture was stirred for 10 minutes at room temperature and was then cooled to −20° C. A catalytic amount of BF$_3$-Et$_2$O (0.1 ml) was added and the mixture was stirred at −15° C. and the reaction progress was monitored by TLC, which indicated the completion after 60 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain Compound (R)-22 (1.02 grams) in 82% yield.

$^1$HNMR (500 MHz, CDCl$_3$): "Ring I" δ$_H$ 3.55 (dd, 1H, J$_1$=4.5 and J$_2$=10.7 Hz, H-2'), 4.17 (d, 1H, J=13.1 Hz, H-6'), 4.30 (dd, 1H, J$_1$=4.2 and J$_2$=12.4 Hz, H-6'), 4.56 (m, 1H, H-5'), 5.08 (t, 1H, J=9.7 Hz, H-4'), 5.43 (t, 1H, J=9.9 Hz, H-3'), 5.83 (d, 1H, J=3.9 Hz, H-1'); "Ring II" δ$_H$ 1.64 (ddd, 1H, J$_1$=J$_2$=J$_3$=12.5 Hz, H-2$_{ax}$), 2.42 (td, 1H, J$_1$=4.5 and J$_2$=12.5 Hz, H-2$_{eq}$), 3.49-3.56 (m, 2H, H-1 and H-3), 3.74 (t, 1H, J=10.0 Hz, H-4), 3.92 (t, 1H, J=9.1 Hz, H-5), 5.03 (d, 1H, J=9.9 Hz, H-6); "Ring III" δ$_H$ 1.41 (d, 3H, J=6.9 Hz, CH$_3$), 3.76 (m, 1H, H-5"), 4.39 (t, 1H, J=4.9 Hz, H-4"), 5.50 (dd, 1H, J$_1$=5.1 and J$_2$=7.0 Hz, H-3"), 5.60 (d, 1H, J=4.9 Hz, H-2"), 5.68 (s, 1H, H-1"). Additional peaks in the spectrum were identified as follows: δ$_H$ 2.06 (s, 3H, OAc), 2.09 (s, 3H, OAc), 2.11 (s, 3H, OAc), 2.34 (s, 3H, OAc), 7.37-7.41 (m, 4H, Ar), 7.57 (m, 2H, Ar), 7.92 (d, 4H, J=8.0 Hz Ar).

$^{13}$CNMR (125 MHz, CDCl$_3$): δ$_H$ 15.1 (C-6"), 20.5 (OAc), 20.6 (OAc), 20.7 (OAc), 20.8 (OAc), 31.7 (C-1), 58.2 (2C), 58.6, 61.7 (2C), 68.0, 68.1, 70.7, 71.4, 73.7, 74.6, 77.8, 79.2, 83.9, 96.6 (C-1'), 107.1 (C-1"), 128.4 (2C, Ar), 128.7 (Ar), 128.8 (Ar), 129.6 (2C, Ar), 133.4 (Ar), 133.5 (Ar), 164.9 (C=O), 165.4 (C=O), 169.7 (2C, C=O), 169.9 (C=O), 170.6 (C=O).

MALDI TOFMS calculated for C$_{40}$H$_{44}$N$_{12}$O$_{16}$Na ([M+Na]$^+$) m/e: 971.3; measured m/e: 971.4.

Preparation of 5-O-(5-Azido-5,6-dideoxy-2,3-O-dibenzoyl-α-L-talofuranosyl)-3',4',6',6-tetra-O-acetyl-2',3-diazido-1-N-[(S)-4-azido-2-O-acetyl-butanoyl]paromamine (Compound (S)-23)

Anhydrous CH$_2$Cl$_2$ (15 ml) was added to a powdered, flame-dried 4 Å molecular sieves (2.0 grams), followed by the addition acceptor Compound 20 (1.0 grams, 0.0014 mol) and donor Compound (S)-17 (2.2 grams, 0.0042 mol). The reaction mixture was stirred for 10 minutes at room temperature and was then cooled to −20° C. A catalytic amount of BF$_3$-Et$_2$O (0.1 ml) was added and the mixture was stirred at −15° C. and the reaction progress was monitored by TLC, which indicated the completion after 60 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain Compound (S)-23 (1.19 grams) in 79% yield.

$^1$HNMR (500 MHz, CDCl$_3$): "Ring I" δ$_H$ 3.63 (dd, 1H, J$_1$=4.2, J$_2$=10.4 Hz, H-2'), 4.18 (d, 1H, J=10.8 Hz, H-6'), 4.29 (dd, 1H, J$_1$=2.9, J$_2$=12.4 Hz, H-6'), 4.54 (m, 1H, H-5'), 5.09 (t, 1H, J=10.2 Hz, H-4'), 5.42 (t, 1H, J=10.2 Hz, H-3'), 5.84 (d, 1H, J=3.9 Hz, H-1'); "Ring II" δ$_H$ 1.50 (ddd, 1H, J$_1$=J$_2$=J$_3$=12.5 Hz, H-2$_{ax}$), 2.53 (td, 1H, J$_1$=4.5, J$_2$=12.5 Hz, H-2$_{eq}$), 3.60 (m, 1H, H-3), 3.74 (t, 1H, J=9.5 Hz, H-4), 3.96 (t, 1H, J=10.0 Hz, H-5), 4.06 (m, 1H, H-1), 4.93 (d, 1H, J=9.9 Hz, H-6); "Ring III" δ$_H$ 1.33 (d, 3H, J=6.9 Hz, CH$_3$), 3.70 (m, 1H, H-5"), 4.33 (t, 1H, J=6.0 Hz, H-4"), 5.55 (dd, 1H, J$_1$=4.9, J$_2$=7.7 Hz, H-3"), 5.57 (m, 2H, H-2" and H-1"). Additional peaks in the spectrum were identified as follows: δ$_H$ 2.04-2.10 (m, 2H, H-8 and H-8), 2.06 (s, 3H, OAc), 2.09 (s, 6H, OAc), 2.26 (s, 3H, OAc), 2.35 (s, 3H, OAc), 3.37 (dd, 2H, J$_1$=6.0, J$_2$=7.5 Hz, H-9 and H-9), 5.20 (dd, 1H, J$_1$=1.5, J$_2$=8.5 Hz, H-7), 6.69 (d, 1H, J=7.5 Hz, NH), 7.35 (t, 2H, J=8.0 Hz, Ar), 7.43 (t, 2H, J=8.0 Hz, Ar), 7.53 (t, 1H, J=8.0 Hz, Ar), 7.55 (t, 1H, J=8.0 Hz, Ar), 7.87 (dd, 2H, J$_1$=1.1, J$_2$=8.2 Hz, Ar), 7.95 (dd, 2H, J$_1$=1.2, J$_2$=8.2 Hz, Ar).

$^{13}$CNMR (125 MHz, CDCl$_3$): δ$_C$ 15.4 (C-6"), 20.6 (4C, OAc), 20.9 (OAc), 31.9 (C-1), 47.0, 48.5, 58.4, 58.7, 61.7, 61.8, 68.0, 68.2, 70.8, 70.9, 71.4, 73.1, 74.7, 78.3, 79.7, 83.7, 96.7 (C-1'), 107.5 (C-1"), 128.4 (Ar), 128.5 (2C, Ar), 128.7 (Ar), 129.6 (Ar), 129.7 (Ar), 133.5 (Ar), 133.6 (Ar), 165.0 (C=O), 165.2 (C=O), 168.8 (C=O), 169.7 (2C, C=O), 169.8 (C=O), 170.6 (C=O), 172.5 (C=O).

MALDI TOFMS calculated for C$_{46}$H$_{54}$N$_{13}$O$_{19}$ ([M+H]$^+$) m/e: 1092.3; measured m/e: 1092.3.

Preparation of 5-O-(5-Azido-5,6-dideoxy-2,3-O-dibenzoyl-β-D-allofuranosyl)-3',4',6',6-tetra-O-acetyl-2',3-diazido-1-N-[(S)-4-azido-2-O-acetyl-butanoyl]paromamine (Compound (R)-24)

Anhydrous CH$_2$Cl$_2$ (15 ml) was added to a powdered, flame-dried 4 Å molecular sieves (2.0 grams), followed by the addition acceptor Compound 20 (1.0 grams, 0.0014 mol) and donor Compound (R)-18 (2.2 grams, 0.0042 mol). The reaction mixture was stirred for 10 minutes at room temperature and was then cooled to −20° C. A catalytic amount of BF$_3$-Et$_2$O (0.1 ml) was added and the mixture was stirred at −15° C. and the reaction progress was monitored by TLC, which indicated the completion after 60 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain Compound (R)-24 (1.27 grams) in 89% yield.

$^1$HNMR (500 MHz, CDCl$_3$): "Ring I" $\delta_H$ 3.53 (dd, 1H, J$_1$=4.7, J$_2$=10.7 Hz, H-2'), 4.18 (d, 1H, J=10.1 Hz, H-6'), 4.30 (dd, 1H, J$_1$=3.9, J$_2$=12.3 Hz, H-6'), 4.56 (m, 1H, H-5'), 5.09 (t, 1H, J=10.2 Hz, H-4'), 5.44 (t, 1H, J=9.7 Hz, H-3'), 5.84 (d, 1H, J=3.9 Hz, H-1'); "Ring II" $\delta_H$ 1.48 (ddd, 1H, J$_1$=J$_2$=J$_3$=12.5 Hz, H-2$_{ax}$), 2.52 (td, 1H, J$_1$=4.5, J$_2$=12.5 Hz, H-2$_{eq}$), 3.60 (m, 1H, H-3), 3.74 (t, 1H, J=9.5 Hz, H-4), 4.00-4.08 (m, 2H, H-5 and H-1), 4.93 (t, 1H, J=9.9 Hz, H-6); "Ring III" $\delta_H$ 1.41 (d, 3H, J=6.9 Hz, CH$_3$), 3.83 (m, 1H, H-5"), 4.37 (dd, 1H, J$_1$=4.1, J$_2$=5.7 Hz, H-4"), 5.60 (t, 1H, J=6.5 Hz, H-3"), 5.64 (d, 1H, J=6.5 Hz, H-2"), 5.70 (s, 1H, H-1"). Additional peaks in the spectrum were identified as follows: 6H 2.04-2.10 (m, 2H, H-8 and H-8), 2.06 (s, 3H, OAc), 2.10 (s, 3H, OAc), 2.11 (s, 3H, OAc), 2.22 (s, 3H, OAc), 2.27 (s, 3H, OAc), 3.37 (dd, 2H, J$_1$=6.0, J$_2$=7.5 Hz, H-9 and H-9), 5.19 (dd, 1H, J$_1$=1.5, J$_2$=8.5 Hz, H-7), 6.69 (d, 1H, J=7.5 Hz, NH), 7.35-7.43 (m, 4H, Ar), 7.53-7.59 (m, 2H, Ar), 7.87-7.92 (m, 4H, Ar).

$^{13}$CNMR (125 MHz, CDCl$_3$): $\delta_C$ 15.3 (C-6"), 20.5 (OAc), 20.5 (OAc), 20.6 (OAc), 20.7 (OAc), 20.8 (OAc), 30.4, 32.1, 47.0, 48.4, 58.2, 58.5, 61.6, 61.7, 68.0, 68.1, 70.7, 70.8, 70.9, 73.4, 74.7, 78.0, 79.5, 83.3, 96.8 (C-1'), 106.9 (C-1"), 128.4 (2C, Ar), 128.7 (2C, Ar), 129.5 (Ar), 129.6 (Ar), 133.5 (2C, Ar), 164.9 (C=O), 165.2 (C=O), 168.9 (C=O), 169.6 (C=O), 169.7 (C=O), 169.8 (C=O), 170.6 (C=O), 172.3 (C=O).

MALDI TOFMS calculated for C$_{46}$H$_{54}$N$_{13}$O$_{19}$ ([M+H]$^+$) m/e: 1092.3; measured m/e: 1092.3.

Preparation of 5-O-(5-Amino-5,6-dideoxy-α-L-talo-furanosyl)-paromamine (NB118)

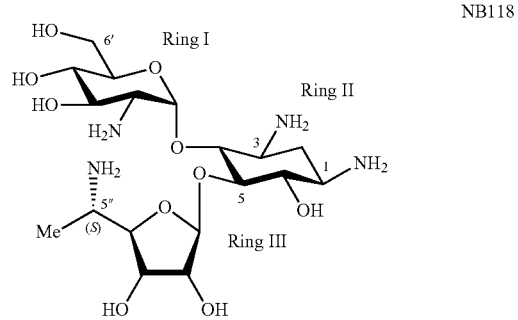

The glycosylation product Compound (S)-21 (1.0 grams, 0.001 mol) was treated with a solution of MeNH$_2$ (33% solution in EtOH, 50 ml and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which PMe$_3$ (1 M solution in THF, 5.0 ml, 5.0 mmol) was added. The reaction progress was monitored by TLC [CH$_2$Cl$_2$/MeOH/H$_2$O/MeNH$_2$ (33% solution in EtOH) 10:15:6:15], which indicated completion after 1 hour. The product was purified by column chromatography on a short column of silica gel. The column was washed with the following solvents: THF (800 ml), CH$_2$Cl$_2$ (800 ml), EtOH (200 ml), and MeOH (400 ml). The product was then eluted with a mixture of 20% MeNH$_2$ (33% solution in EtOH) in 80% MeOH. Fractions containing the product were combined and evaporated to dryness. The residue was re-dissolved in a small volume of water and evaporated again (2-3 repeats) to afford the free amine form of NB118.

The analytically pure product was obtained by passing the above product through a short column of Amberlite CG50 (NH$_4^+$ form). The column was first washed with a mixture of MeOH/H$_2$O (3:2), then the product was eluted with a mixture of MeOH/H$_2$O/NH$_4$OH (80:10:10) to afford NB118 (0.405 grams, 82% yield).

For the storage and biological tests, compound was converted to its sulfate salt form: the free base was dissolved in water, the pH was adjusted around 7.0 with H$_2$SO$_4$ (0.1 N) and lyophilized. [α]$_D^{20}$=+38.4 (c=0.2, MeOH).

$^1$HNMR (500 MHz, CD$_3$OD): "Ring I" $\delta_H$ 2.64 (dd, 1H, J$_1$=3.7, J$_2$=10.4 Hz, H-2'), 3.27 (t, 1H, J=9.7 Hz, H-4') 3.52 (t, 1H, J=10.8 Hz, H-3'), 3.67 (dd, 1H, J$_1$=6.0, J$_2$=11.8 Hz, H-6'), 3.79 (m, 1H, H-5'), 3.87 (dd, 1H, J$_1$=2.0, J$_2$=11.9 Hz, H-6') 5.20 (d, 1H, J=3.4 Hz, H-1'); "Ring II" $\delta_H$ 1.20 (ddd, 1H, J$_1$=J$_2$=J$_3$=12.5 Hz, H-2$_{ax}$), 1.97 (td, 1H, J$_1$=4.5, J$_2$=12.5 Hz, H-2$_{eq}$), 2.64 (m, 1H, H-1), 2.78 (m, 1H, H-3), 3.21 (t, 1H, J=9.3 Hz, H-6), 3.38 (t, 1H, J=9.5 Hz, H-4), 3.50 (t, 1H, J=9.2, H-5); "Ring III" $\delta_H$ 1.18 (d, 3H, J=6.2 Hz, CH$_3$), 2.96 (m, 1H, H-5"), 3.57 (t, 1H, J=6.9 Hz, H-4"), 4.02 (t, 1H, J=5.5 Hz, H-3"), 4.06 (dd, 1H, J$_1$=2.9, J$_2$=5.4 Hz, H-2"), 5.25 (d, 1H, J=2.7 Hz, H-1").

$^{13}$CNMR (125 MHz, CD$_3$OD): $\delta_C$ 19.3 (C-6"), 37.5 (C-1), 50.6, 52.3, 52.6, 57.8, 62.7 (C-6'), 72.1, 72.2, 75.3, 75.4, 76.2, 78.6, 84.6, 87.4, 88.6, 102.0 (C-1'), 109.5 (C-1").

MALDI TOFMS calculated for C$_{18}$H$_{37}$N$_4$O$_{10}$ ([M+H]$^+$) m/e: 469.2; measured m/e: 469.2.

Preparation of 5-O-(5-Amino-5,6-dideoxy-β-D-allo-furanosyl)-paromamine (NB119

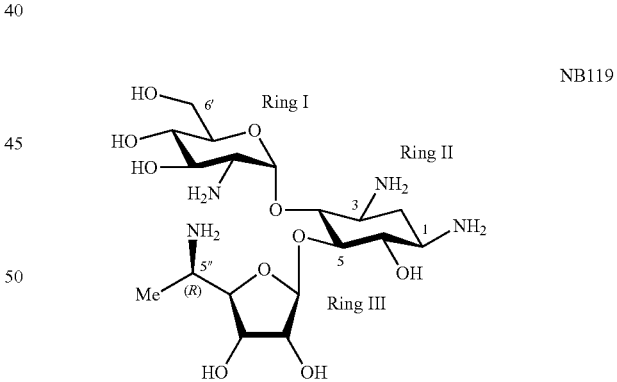

The glycosylation product Compound (R)-22 (1.0 grams, 0.001 mol) was treated with a solution of MeNH$_2$ (33% solution in EtOH, 50 ml) and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which PMe$_3$ (1 M solution in THF, 5.0 ml, 5.0 mmol) was added. The reaction progress was monitored by TLC [CH$_2$Cl$_2$/MeOH/H$_2$O/MeNH$_2$ (33% solution in EtOH) 10:15:6:15], which indicated completion after 1 hour. The product was purified by column chromatography on a short column of silica gel. The column was washed with the following solvents: THF (800 ml), $CH_2Cl_2$ (800 ml), EtOH (200 ml), and MeOH (400 ml). The product was then eluted with a mixture of 20% $MeNH_2$ (33% solution in EtOH) in 80% MeOH. Fractions containing the product were combined and evaporated to dryness. The residue was re-dissolved in a small volume of water and evaporated again (2-3 repeats) to afford the free amine form of NB119, also referred to as NB119.

The analytically pure product was obtained by passing the above product through a short column of Amberlite CG50 ($NH_4^+$ form). The column was first washed with a mixture of $MeOH/H_2O$ (3:2), then the product was eluted with a mixture of $MeOH/H_2O/NH_4OH$ (80:10:10) to afford NB119 (0.398 grams, 80% yield).

For the storage and biological tests, compound was converted to its sulfate salt form: the free base was dissolved in water, the pH was adjusted around 7.0 with $H_2SO_4$ (0.1 N) and lyophilized. $[\alpha]_D^{20}=+37.0$ (c=0.2, MeOH).

$^1$HNMR (500 MHz, $CD_3OD$): "Ring I" $\delta_H$ 2.64 (dd, 1H, $J_1$=3.4, $J_2$=10.2 Hz, H-2'), 3.27 (t, 1H, J=9.1 Hz, H-4'), 3.52 (t, 1H, J=8.9 Hz, H-3'), 3.68 (t, 1H, J=6.1 Hz, H-6'), 3.79 (m, 1H, H-5'), 3.87 (dd, 1H, $J_1$=2.5, $J_2$=12.2 Hz, H-6'), 5.20 (d, 1H, J=3.6 Hz, H-1'); "Ring II" $\delta_H$ 1.21 (ddd, 1H, $J_1$=$J_2$=$J_3$=12.5 Hz, H-$2_{ax}$), 1.97 (td, 1H, $J_1$=4.5, $J_2$=12.5 Hz, H-$2_{eq}$), 2.64 (m, 1H, H-1), 2.78 (m, 1H, H-3), 3.18 (t, 1H, J=9.1 Hz, H-6), 3.37 (t, 1H, J=9.5 Hz, H-4), 3.46 (t, 1H, J=9.2 Hz, H-5); "Ring III" $\delta_H$ 1.16 (d, 3H, J=6.2 Hz, $CH_3$), 3.09 (m, 1H, H-5"), 3.70 (t, 1H, J=5.3 Hz, H-4"), 4.04 (dd, 1H, $J_1$=3.3, $J_2$=5.3 Hz, H-2"), 4.15 (t, 1H, J=5.5 Hz, H-3"), 5.21 (d, 1H, J=2.7 Hz, H-1").

$^{13}$CNMR (125 MHz, $CD_3OD$): $\delta_C$ 18.8 (C-6"), 37.6 (C-1), 49.4, 52.1, 52.6, 57.8, 62.8 (C-6'), 70.8, 72.1, 75.2, 75.4, 76.1, 78.4, 84.7, 87.8, 88.2, 102.0 (C-1'), 109.5 (C-1").

MALDI TOFMS calculated for $C_{18}H_{37}N_4O_{10}$ ($[M+H]^+$) m/e: 469.2; measured m/e: 469.2

Preparation of 5-O-(5-Amino-5,6-dideoxy-α-L-talo-furanosyl)-1-N-[(S)-4-amino-2-hydroxy-butanoyl] paromamine (NB122)

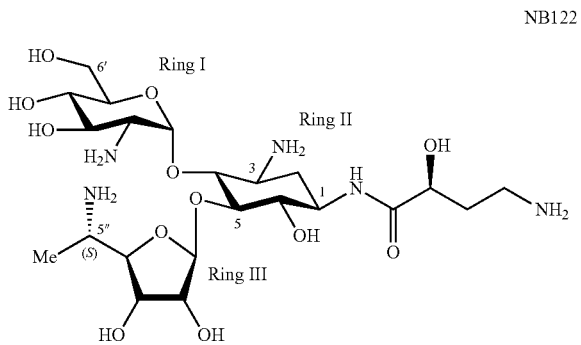

NB122

The glycosylation product Compound (S)-23 (1.1 grams, 0.001 mol) was treated with a solution of $MeNH_2$ (33% solution in EtOH, 50 ml) and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which $PMe_3$ (1 M solution in THF, 5.0 ml, 5.0 mmol) was added. The reaction progress was monitored by TLC [$CH_2Cl_2$/MeOH/$H_2O$/ $MeNH_2$ (33% solution in EtOH) 10:15:6:15], which indicated completion after 1 hour. The product was purified by column chromatography on a short column of silica gel. The column was washed with the following solvents: THF (800 ml), $CH_2Cl_2$ (800 ml), EtOH (200 ml), and MeOH (400 ml). The product was then eluted with a mixture of 20% $MeNH_2$ (33% solution in EtOH) in 80% MeOH. Fractions containing the product were combined and evaporated to dryness. The residue was re-dissolved in a small volume of water and evaporated again (2-3 repeats) to afford the free amine form of NB122.

The analytically pure product was obtained by passing the above product through a short column of Amberlite CG50 ($NH_4^+$ form). The column was first washed with a mixture of $MeOH/H_2O$ (3:2), then the product was eluted with a mixture of $MeOH/H_2O/NH_4OH$ (80:10:10) to afford NB122 (0.450 grams, 79% yield).

For the storage and biological tests, compound was converted to its sulfate salt form: the free base was dissolved in water, the pH was adjusted around 7.0 with $H_2SO_4$ (0.1 N) and lyophilized. $[\alpha]_D20=+35.4$ (c=0.2, $H_2O$).

$^1$HNMR (500 MHz, $CD_3OD$) "Ring I" $\delta_H$ 2.65 (dd, 1H, $J_1$=3.7 and $J_2$=10.3 Hz, H-2'), 3.26 (t, 1H, J=8.9 Hz, H-4'), 3.54 (t, 1H, J=9.2 Hz, H-3'), 3.68 (dd, 1H, $J_1$=5.9 and $J_2$=11.8 Hz, H-6'), 3.80 (m, 1H, H-5'), 3.87 (dd, 1H, $J_1$=1.7 and $J_2$=11.7 Hz, H-6'), 5.21 (d, 1H, J=3.3 Hz, H-1'); "Ring II" $\delta_H$ 1.34 (ddd, 1H, $J_1$=$J_2$=$J_3$=12.5 Hz, H-$2_{ax}$), 1.99 (td, 1H, $J_1$=4.5 and $J_2$=12.5 Hz, H-$2_{eq}$), 2.84 (m, 1H, H-3), 3.40 (t, 1H, J=9.0 Hz, H-4), 3.50-3.59 (m, 2H, H-5 and H-6), 3.81 (m, 1H, H-1); "Ring III" $\delta_H$ 1.17 (d, 3H, J=6.7 Hz, $CH_3$), 2.95 (m, 1H, H-5"), 3.57 (t, 1H, J=6.5 Hz, H-4"), 4.01 (t, 1H, J=5.7 Hz, H-3"), 4.08 (dd, 1H, $J_1$=2.7 and $J_2$=5.4 Hz, H-2"), 5.26 (d, 1H, J=2.5 Hz, H-1"). Additional peaks in the spectrum were identified as follows: $\delta_H$ 1.82 (m, 1H, H-8), 1.94 (m, 1H, H-8), 2.83 (t, 2H, J=6.4 Hz, H-9 and H-9), 4.14 (dd, 1H, $J_1$=4.1 and $J_2$=7.6 Hz, H-7).

$^{13}$CNMR (125 MHz, $CD_3OD$): $\delta_C$ 19.2 (C-6"), 35.9, 37.8, 38.9, 50.8, 50.9, 52.4, 57.8, 62.8, 71.7, 72.1, 72.3, 75.3, 75.4, 75.6, 76.3, 84.7, 86.9, 88.6, 101.9 (C-1'), 109.9 (C-1"), 177.1 (C=O).

MALDI TOFMS calculated for $C_{22}H_{44}N_5O_{12}$ ($[M+H]^+$) m/e: 570.3; measured m/e: 570.27.

Preparation of 5-O-(5-Amino-5,6-dideoxy-β-D-allo-furanosyl)-1-N-[(S)-4-amino-2-hydroxy-butanoyl] paromamine (NB123)

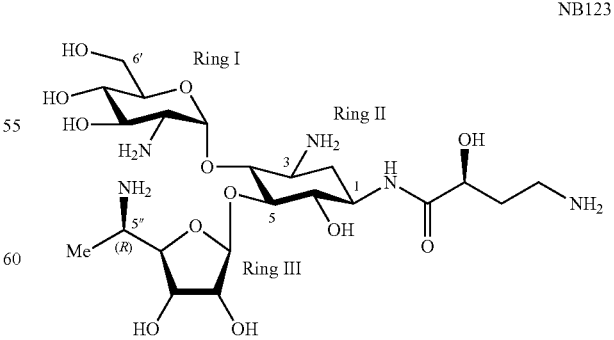

NB123

The glycosylation product Compound (R)-24 (1.2 grams, 0.0011 mol) was treated with a solution of $MeNH_2$ (33% solution in EtOH, 50 ml) and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which PMe$_3$ (1 M solution in THF, 5.0 ml, 5.0 mmol) was added. The reaction progress was monitored by TLC [CH$_2$Cl$_2$/MeOH/H$_2$O/MeNH$_2$ (33% solution in EtOH) 10:15:6:15], which indicated completion after 1 hour. The product was purified by column chromatography on a short column of silica gel. The column was washed with the following solvents: THF (800 ml), CH$_2$Cl$_2$ (800 ml), EtOH (200 ml), and MeOH (400 ml). The product was then eluted with a mixture of 20% MeNH$_2$ (33% solution in EtOH) in 80% MeOH. Fractions containing the product were combined and evaporated to dryness. The residue was re-dissolved in a small volume of water and evaporated again (2-3 repeats) to afford the free amine form of NB123.

The analytically pure product was obtained by passing the above product through a short column of Amberlite CG50 (NH$_4^+$ form). The column was first washed with a mixture of MeOH/H$_2$O (3:2), then the product was eluted with a mixture of MeOH/H$_2$O/NH$_4$OH (80:10:10) to afford NB123 (0.510 grams, 82% yield).

For the storage and biological tests, compound was converted to its sulfate salt form: the free base was dissolved in water, the pH was adjusted around 7.0 with H$_2$SO$_4$ (0.1 N) and lyophilized. $[\alpha]_D^{20}$=+32.2 (c=0.2, H$_2$O).

$^1$HNMR (500 MHz, CD$_3$OD) "Ring I" $\delta_H$ 2.65 (dd, 1H, J$_1$=3.4, J$_2$=10.0 Hz, H-2'), 3.27 (t, 1H, J=9.0 Hz, H-4'), 3.54 (t, 1H, J=9.1 Hz, H-3'), 3.66 (dd, 1H, J$_1$=6.0, J$_2$=12.0 Hz, H-6'), 3.81 (m, 1H, H-5'), 3.88 (dd, 1H, J$_1$=2.0, J$_2$=12.0 Hz, H-6'), 5.21 (d, 1H, J=3.5 Hz, H-1'); "Ring II" $\delta_H$ 1.33 (ddd, 1H, J$_1$=J$_2$=J$_3$=12.5 Hz, H-2$_{ax}$), 1.99 (td, 1H, J$_1$=4.5, J$_2$=12.5 Hz, H-2$_{eq}$), 2.85 (m, 1H, H-3), 3.39 (t, 1H, J=9.0 Hz, H-4), 3.49-3.57 (m, 2H, H-5 and H-6), 3.82 (m, 1H, H-1); "Ring III" $\delta_H$ 1.16 (d, 3H, J=6.7 Hz, CH$_3$), 3.09 (m, 1H, H-5"), 3.70 (t, 1H, J=5.4 Hz, H-4"), 4.08 (dd, 1H, J$_1$=2.6, J$_2$=5.1 Hz, H-2"), 4.14 (t, 1H, J=5.7 Hz, H-3"), 5.22 (d, 1H, J=2.7 Hz, H-1"). Additional peaks in the spectrum were identified as follows: $\delta_H$ 1.82 (m, 1H, H-8), 1.94 (m, 1H, H-8), 2.84 (t, 2H, J=7.2 Hz, H-9 and H-9), 4.15 (dd, 1H, J$_1$=4.0, J$_2$=7.5 Hz, H-7).

$^{13}$CNMR (125 MHz, CD$_3$OD): $\delta_H$ 18.8 (C-6"), 35.9, 37.6, 38.9, 49.6, 40.8, 52.3, 57.8, 62.8, 71.0, 71.6, 72.1, 75.2, 75.3, 75.4, 76.2, 85.0, 87.1, 87.9, 101.9 (C-1'), 110.0 (C-1"), 177.0 (C=O).

MALDI TOFMS calculated for C$_{22}$H$_{44}$N$_5$O$_{12}$ ([M+H]$^+$) m/e: 570.3; measured m/e: 570.27.

Preparation of 6'-(R)-Methyl-5-O-(5-azido-5,6-dideoxy-2,3-O-dibenzoyl-α-L-talofuranosyl)-3',4',6', 6-tetra-O-acetyl-2',1,3-triazido paromamine (Compound (S)-221)

Anhydrous CH$_2$Cl$_2$ (15 ml) was added to a powdered, flame-dried 4 Å molecular sieves (2.0 grams), followed by the addition acceptor Compound 219 (0.9 grams, 0.0015 mol) and donor Compound (S)-17 (2.0 grams, 0.0037 mol). The reaction mixture was stirred for 10 minutes at room temperature and was then cooled to −20° C. A catalytic amount of BF$_3$-Et$_2$O (0.1 ml) was added and the mixture was stirred at −15° C. and the reaction progress was monitored by TLC, which indicated the completion after 120 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain Compound (S)-221 (1.1 grams) in 75% yield.

$^1$HNMR (500 MHz, CDCl$_3$): "Ring I" $\delta_H$ 1.27 (d, 3H, J=6.0 Hz, CH$_3$), 3.58 (dd, 1H, J$_1$=5.5, J$_2$=10.5 Hz, H-2'), 4.45 (d, 1H, J=10.7 Hz, H-5'), 4.96-5.02 (m, 2H, H-4' and H-6'), 5.42 (t, 1H, J=9.6 Hz, H-3'), 5.95 (d, 1H, J=3.7 Hz, H-1'); "Ring II" $\delta_H$ 1.51 (ddd, 1H, J$_1$=J$_2$=J$_3$=12.5 Hz, H-2$_{ax}$), 2.41 (td, 1H, J$_1$=4.5, J$_2$=12.5 Hz, H-2$_{eq}$), 3.55 (m, 2H, H-1 and H-3), 3.76 (t, 1H, J=9.4 Hz, H-4), 3.88 (t, 1H, J=9.0 Hz, H-5), 5.03 (t, 1H, J=9.1 Hz, H-6); "Ring III" $\delta_H$ 1.27 (d, 3H, J=5.6 Hz, CH$_3$), 3.76 (m, 1H, H-5"), 4.35 (dd, 1H, J$_1$=6.9, J$_2$=10.9 Hz, H-4"), 5.45 (t, 1H, J=5.5 Hz, H-3"), 5.62 (m, 2H, H-2" and H-1"). Additional peaks in the spectrum were identified as follows: $\delta_H$ 2.08 (s, 3H, OAc), 2.09 (s, 6H, OAc), 2.38 (s, 3H, OAc), 7.37 (t, 2H, J=7.8 Hz, Ar), 7.41 (t, 2H, J=7.8 Hz, Ar), 7.53-7.60 (m, 2H, Ar), 7.89 (d, 2H, J=8.0 Hz, Ar), 7.93 (d, 2H, J=8.2 Hz, Ar).

$^{13}$CNMR (125 MHz, CDCl$_3$): $\delta_C$ 13.3 (C-7'), 15.4 (C-6"), 20.6 (2C, OAc), 20.9 (OAc), 21.1 (OAc), 32.1 (C-2), 58.4, 58.8, 59.5, 61.7, 68.5, 69.0, 70.1, 70.8, 71.8, 73.6, 74.6, 77.3, 79.6, 84.4, 96.0 (C-1'), 107.6 (C-1"), 128.4 (Ar), 128.5 (Ar), 128.6 (Ar), 128.7 (Ar), 129.6 (Ar), 129.7 (Ar), 133.5 (Ar), 133.6 (Ar), 164.9 (C=O), 165.3 (C=O), 169.7 (C=O), 169.9 (C=O), 170.1 (C=O), 170.2 (C=O).

MALDI TOFMS calculated for C$_{41}$H$_{46}$N$_{12}$O$_{16}$ Na ([M+Na]$^+$) m/e: 985.3; measured m/e: 985.4.

Preparation of 6'-(R)-Methyl-5-O-(5-azido-5,6-dideoxy-2,3-O-dibenzoyl-β-D-allofuranosyl)-3',4',6', 6-tetra-O-acetyl-2',1,3-triazido paromamine (Compound (R)-222)

Anhydrous CH$_2$Cl$_2$ (15 ml) was added to a powdered, flame-dried 4 Å molecular sieves (2.0 grams), followed by the addition acceptor Compound 219 (1.0 grams, 0.0017 mol) and donor Compound (R)-18 (2.2 grams, 0.004 mol). The reaction mixture was stirred for 10 minutes at room temperature and was then cooled to −20° C. A catalytic amount of BF$_3$-Et$_2$O (0.1 ml) was added and the mixture was stirred at −15° C. and the reaction progress was monitored by TLC, which indicated the completion after 120 minutes. The reaction mixture was diluted with ethyl acetate and washed with saturated NaHCO$_3$ and brine. The combined organic layer was dried over MgSO$_4$, evaporated and subjected to column chromatography (EtOAc/Hexane) to obtain Compound (R)-222 (1.2 grams) in 75% yield.

$^1$HNMR (500 MHz, CDCl$_3$): "Ring I" $\delta_H$ 1.28 (d, 3H, J=6.7 Hz, CH$_3$), 3.46 (dd, 1H, J$_1$=4.5, J$_2$=10.4 Hz, H-2'), 4.47 (d, 1H, J=10.7 Hz, H-5'), 4.96-5.02 (m, 2H, H-4' and H-6'), 5.44 (t, 1H, J=9.6 Hz, H-3'), 5.93 (d, 1H, J=3.3 Hz, H-1'); "Ring II" $\delta_H$ 1.50 (ddd, 1H, J$_1$=J$_2$=J$_3$=12.5 Hz, H-2$_{ax}$), 2.41 (td, 1H, J$_1$=4.5 and J$_2$=12.5 Hz, H-2$_{eq}$), 3.56 (m, 2H, H-1 and H-3), 3.76 (t, 1H, J=10.0 Hz, H-4), 3.92 (t, 1H, J=9.5 Hz, H-5), 5.04 (t, 1H, J=9.6 Hz, H-6); "Ring III" $\delta_H$ 1.42 (d, 3H, J=6.9 Hz, CH$_3$), 3.78 (m, 1H, H-5"), 4.40 (t, 1H, J=4.6 Hz, H-4"), 5.50 (t, 1H, J=5.0 Hz, H-3"), 5.59 (t, 1H, J=3.7 Hz, H-2"), 5.64 (s, 1H, H-1"). Additional peaks in the spectrum were identified as follows: $\delta_H$ 2.09 (s, 9H, OAc), 2.33 (s, 3H, OAc), 7.37-7.41 (m, 4H, Ar), 7.56 (m, 2H, Ar), 7.92 (d, 4H, J=8.0 Hz Ar).

$^{13}$CNMR (125 MHz, CDCl$_3$): $\delta_H$ 13.3 (C-7'), 15.0 (C-6"), 20.6 (OAc), 20.7 (OAc), 20.8 (OAc), 21.2 (OAc), 32.1 (C-2), 58.1, 58.2, 58.8, 61.5, 68.9, 70.2, 70.6, 71.4, 73.8, 74.6, 77.0, 77.1, 79.4, 83.9, 96.1 (C-1'), 107.0 (C-1"), 128.4 (2C, Ar), 128.7 (2C, Ar), 129.6 (2C, Ar), 133.5 (Ar), 133.6 (Ar), 164.9 (C=O), 165.4 (C=O), 169.8 (C=O), 169.9 (2C, C=O), 170.1 (C=O).

MALDI TOFMS calculated for $C_{41}H_{46}N_{12}O_{16}Na$ ([M+Na]) m/e: 985.3; measured m/e: 985.4.

Preparation of 6'-(R)-Methyl-5-O-(5-azido-5,6-dideoxy-2,3-O-dibenzoyl-α-L-talofuranosyl)-3',4',6',6-tetra-O-acetyl-2',3-diazido-1-N-[(S)-4-azido-2-O-acetyl-butanoyl]paromamine (Compound (S)-223)

Anhydrous $CH_2Cl_2$ (15 ml) was added to a powdered, flame-dried 4 Å molecular sieves (2.0 grams), followed by the addition acceptor Compound 220 (1.0 grams, 0.0014 mol) and donor Compound (S)-17 (2.5 grams, 0.0046 mol). The reaction mixture was stirred for 10 minutes at room temperature and was then cooled to −20° C. A catalytic amount of $BF_3$-$Et_2O$ (0.1 ml) was added and the mixture was stirred at −15° C. and the reaction progress was monitored by TLC, which indicated the completion after 60 minutes. The reaction mixture was diluted with ethyl acetate and washed with saturated $NaHCO_3$ and brine. The combined organic layer was dried over $MgSO_4$, evaporated and subjected to column chromatography (EtOAc/Hexane) to obtain Compound (S)-223 (1.1 grams) in 73% yield.

$^1$HNMR (500 MHz, $CDCl_3$): $^1$HNMR (500 MHz, $CDCl_3$): "Ring I" $\delta_H$ 1.27 (d, 3H, J=5.2 Hz, $CH_3$), 3.54 (dd, 1H, $J_1$=4.3, $J_2$=10.5 Hz, H-2'), 4.45 (dd, 1H, $J_1$=1.8, $J_2$=10.6 Hz, H-5'), 4.96-5.02 (m, 2H, H-4' and H-6'), 5.43 (t, 1H, J=9.4 Hz, H-3'), 5.94 (d, 1H, J=3.7 Hz, H-1'); "Ring II" $\delta_H$ 1.44 (ddd, 1H, $J_1$=$J_2$=$J_3$=12.5 Hz, H-2$_{ax}$), 2.52 (td, 1H, $J_1$=4.5, $J_2$=12.5 Hz, H-2$_{eq}$), 3.60 (m, 1H, H-3), 3.66 (t, 1H, J=4.5 Hz, H-4), 3.99 (t, 1H, J=6.4 Hz, H-5), 4.05 (m, 1H, H-1), 4.94 (t, 1H, J=9.2 Hz, H-6); "Ring III" $\delta_H$ 1.32 (d, 3H, J=6.9 Hz, $CH_3$), 3.72 (m, 1H, H-5"), 4.32 (dd, 1H, $J_1$=5.85, $J_2$=8.0 Hz, H-4"), 5.55 (dd, 1H, $J_1$=4.7, $J_2$=7.4 Hz, H-3"), 5.65 (m, 2H, H-2" and H-1"). Additional peaks in the spectrum were identified as follows: $\delta_H$ 2.04-2.10 (m, 2H, H-8 and H-8), 2.11 (m, 9H, OAc), 2.22 (s, 3H, OAc), 2.30 (s, 3H, OAc), 3.37 (t, 2H, J=6.8 Hz, H-9 and H-9), 5.20 (t, 1H, J=4.85 Hz, H-7), 6.70 (d, 1H, J=7.5 Hz, NH), 7.35 (t, 2H, J=7.6 Hz, Ar), 7.43 (t, 2H, J=7.8 Hz, Ar), 7.53-7.61 (m, 2H, Ar), 7.86 (dd, 2H, $J_1$=1.1, $J_2$=8.2 Hz, Ar), 7.95 (dd, 2H, $J_1$=1.2, $J_2$=8.2 Hz, Ar).

$^{13}$CNMR (125 MHz, $CDCl_3$): $\delta_C$ 13.5 (C-7'), 15.5 (C-6"), 20.6 (3C, OAc), 20.9 (OAc), 21.1 (OAc), 30.4, 32.2 (C-1), 47.0, 48.4, 58.6, 58.7, 61.6, 68.6, 69.0, 70.3, 70.8 (2C), 71.4, 73.1, 74.7, 77.5, 79.8, 83.6, 96.3 (C-1'), 107.4 (C-1"), 128.4 (Ar), 128.5 (Ar), 128.7 (2C, Ar), 129.6 (Ar), 129.7 (Ar), 133.5 (Ar), 133.6 (Ar), 165.0 (C=O), 165.2 (C=O), 168.8 (C=O), 169.7 (2C, C=O), 169.9 (C=O), 170.0 (C=O), 172.4 (C=O).

MALDI TOFMS calculated for $C_{47}H_{55}N_{13}O_{19}Na$ ([M+Na]$^+$) m/e: 1128.4; measured m/e: 1128.2.

Preparation of 6'-(R)-Methyl-5-O-(5-azido-5,6-dideoxy-2,3-O-dibenzoyl-β-D-allofuranosyl)-3',4',6',6-tetra-O-acetyl-2',3-diazido-1-N-[(S)-4-azido-2-O-acetyl-butanoyl]paromamine (Compound (R)-224)

Anhydrous $CH_2Cl_2$ (15 ml) was added to a powdered, flame-dried 4 Å molecular sieves (2.0 grams), followed by the addition acceptor Compound 220 (1.0 grams, 0.0014 mol) and donor Compound (R)-18 (2.5 grams, 0.0046 mol). The reaction mixture was stirred for 10 minutes at room temperature and was then cooled to −20° C. A catalytic amount of $BF_3$-$Et_2O$ (0.1 ml) was added and the mixture was stirred at −15° C. and the reaction progress was monitored by TLC, which indicated the completion after 90 minutes. The reaction mixture was diluted with ethyl acetate and washed with saturated $NaHCO_3$ and brine. The combined organic layer was dried over $MgSO_4$, evaporated and subjected to column chromatography (EtOAc/Hexane) to obtain Compound (R)-224 (1.15 grams) in 76% yield.

$^1$HNMR (500 MHz, $CDCl_3$): $^1$HNMR (500 MHz, $CDCl_3$): $^1$HNMR (500 MHz, $CDCl_3$): "Ring I" $\delta_H$ 1.28 (d, 3H, J=6.6 Hz, $CH_3$), 3.43 (dd, 1H, $J_1$=4.3, $J_2$=10.6 Hz, H-2'), 4.49 (dd, 1H, $J_1$=2.2, $J_2$=10.7 Hz, H-5'), 4.96-5.02 (m, 2H, H-4' and H-6'), 5.45 (t, 1H, J=10.6 Hz, H-3'), 5.92 (d, 1H, J=3.7 Hz, H-1'); "Ring II" $\delta_H$ 1.42 (ddd, 1H, $J_1$=$J_2$=$J_3$=12.5 Hz, H-2$_{ax}$), 2.52 (td, 1H, $J_1$=4.5, $J_2$=12.5 Hz, H-2$_{eq}$), 3.64 (m, 1H, H-3), 3.76 (t, 1H, J=4.5 Hz, H-4), 4.05 (m, 2H, H-1 and H-5), 4.93 (t, 1H, J=10.0 Hz, H-6); "Ring III" $\delta_H$ 1.39 (d, 3H, J=6.4 Hz, $CH_3$), 3.85 (m, 1H, H-5"), 4.36 (dd, 1H, $J_1$=4.3, $J_2$=6.3 Hz, H-4"), 5.63 (m, 2H, H-2" and H-3"), 5.67 (s, 1H, H-1"). Additional peaks in the spectrum were identified as follows: $\delta_H$ 2.04-2.10 (m, 2H, H-8 and H-8), 2.08 (s, 3H, OAc), 2.09 (s, 3H, OAc), 2.10 (s, 3H, OAc), 2.21 (s, 3H, OAc), 2.25 (s, 3H, OAc), 3.37 (t, 2H, J=6.7 Hz, H-9 and H-9), 5.18 (t, 1H, J=5.0 Hz, H-7), 6.66 (d, 1H, J=7.5 Hz, NH), 7.38-7.42 (m, 4H, Ar), 7.53-7.59 (m, 2H, Ar), 7.89-7.92 (m, 4H, Ar).

$^{13}$CNMR (125 MHz, $CDCl_3$): $\delta_C$ 13.5 (C-7'), 15.2 (C-6"), 20.6 (3C, OAc), 20.8 (OAc), 21.1 (OAc), 30.4, 32.4 (C—I), 47.0, 48.4, 58.1, 58.7, 61.4, 68.6, 69.0, 70.3, 70.5, 70.8, 70.9, 73.4, 74.8, 77.2, 79.6, 83.3, 96.3 (C-1'), 106.9 (C-1"), 128.4 (2C, Ar), 128.7 (2C, Ar), 129.5 (Ar), 129.6 (Ar), 133.5 (2C, Ar), 164.9 (C=O), 165.2 (C=O), 168.8 (C=O), 169.7 (2C, C=O), 169.9 (C=O), 170.0 (C=O), 172.3 (C=O).

MALDI TOFMS calculated for $C_{47}H_{55}N_{13}O_{19}Na$ ([M+Na]$^+$) m/e: 1128.4; measured m/e: 1128.4.

Preparation of 6'-(R)-Methyl-5-O-(5-amino-5,6-dideoxy-α-L-talofuranosyl)-paromamine (NB124)

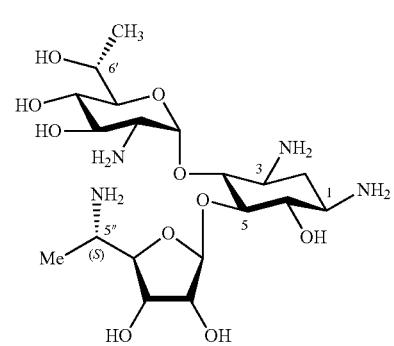

NB124

The glycosylation product Compound (S)-221 (1.0 grams, 0.001 mol) was treated with a solution of $MeNH_2$ (33% solution in EtOH, 50 ml) and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which $PMe_3$ (1 M solution in THF, 5.0 ml, 5.0 mmol) was added. The reaction progress was monitored by TLC [$CH_2Cl_2$/MeOH/$H_2O$/$MeNH_2$ (33% solution in EtOH) 10:15:6:15], which indicated completion after 1 hour. The product was purified by column chromatography on a short column of silica gel. The column was washed with the following solvents: THF (800 ml), CH₂Cl₂ (800 ml), EtOH (200 ml), and MeOH (400 ml). The product was then eluted with a mixture of 20% MeNH₂ (33% solution in EtOH) in 80% MeOH. Fractions containing the product were combined and evaporated to dryness. The residue was re-dissolved in a small volume of water and evaporated again (2-3 repeats) to afford the free amine form of NB124.

Analytically pure product was obtained by passing the above product through a short column of Amberlite CG50 ($NH_4^+$ form). The column was first washed with a mixture of MeOH/H₂O (3:2), then the product was eluted with a mixture of MeOH/H₂O/NH₄OH (80:10:10) to afford NB124 (0.400 grams, 79% yield).

For storage and biological tests, compound was converted to its sulfate salt form: the free base was dissolved in water, the pH was adjusted around 7.0 with H₂SO₄ (0.1 N) and lyophilized.

¹HNMR (500 MHz, CD₃OD): ¹HNMR (500 MHz, CD₃OD): "Ring I" $\delta_H$ 1.21 (d, 3H, J=5.8 Hz, CH₃), 2.61 (dd, 1H, J₁=3.5, J₂=10.0 Hz, H-2'), 3.22 (t, 1H, J=10.0 Hz, H-4'), 3.51 (t, 1H, J=8.9 Hz, H-3'), 3.81 (dd, 1H, J₁=3.0, J₂=10.0 Hz, H-5'), 4.12 (m, 1H, H-6'), 5.20 (d, 1H, J=3.3 Hz, H-1'); "Ring II" $\delta_H$ 1.18 (ddd, 1H, J₁=J₂=J₃=12.5 Hz, H-2$_{ax}$), 1.98 (td, 1H, J₁=4.5, J₂=12.5 Hz, H-2$_{eq}$), 2.63 (m, 1H, H-1), 2.79 (m, 1H, H-3), 3.19 (t, 1H, J=9.7 Hz, H-6), 3.38 (t, 1H, J=9.3 Hz, H-4), 3.48 (t, 1H, J=9.2 Hz, H-5); "Ring III" $\delta_H$ 1.18 (d, 3H, J=6.3 Hz, CH₃), 2.95 (m, 1H, H-5"), 3.57 (t, 1H, J=6.4 Hz, H-4"), 4.03 (t, 1H, J=5.6 Hz, H-3"), 4.07 (m, 1H, H-2"), 5.25 (d, 1H, J=2.5 Hz, H-1").

¹³CNMR (125 MHz, CD₃OD): $\delta_C$ 16.9 (C-7"), 19.3 (C-6"), 37.5 (C-1), 50.6, 52.3, 52.6, 57.8, 67.8, 72.2, 73.6, 75.5, 76.2, 76.7, 78.6, 84.6, 87.3, 88.6, 101.9 (C-1'), 109.6 (C-1").

MALDI TOFMS calculated for $C_{19}H_{39}N_4O_{10}$ ([M+H]⁺) m/e: 483.3; measured m/e: 483.2.

Preparation of 6'-(R)-Methyl-5-O-(5-amino-5,6-dideoxy-β-D-allofuranosyl)-paromamine (NB125)

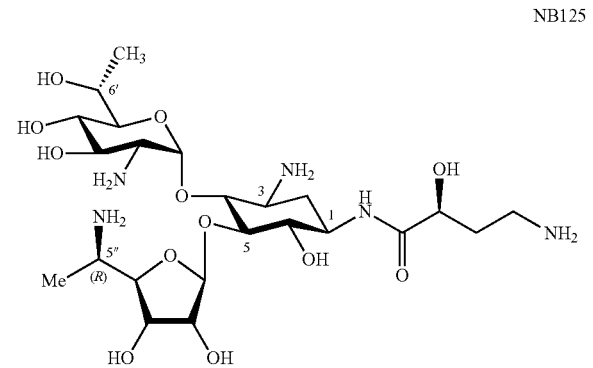

NB125

The glycosylation product Compound (R)-222 (1.0 grams, 0.001 mol) was treated with a solution of MeNH₂ (33% solution in EtOH, 50 ml) and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which PMe₃ (1 M solution in THF, 5.0 ml, 5.0 mmol) was added. The reaction progress was monitored by TLC [CH₂Cl₂/MeOH/H₂O/MeNH₂ (33% solution in EtOH) 10:15:6:15], which indicated completion after 1 hour. The product was purified by column chromatography on a short column of silica gel. The column was washed with the following solvents: THF (800 ml), CH₂Cl₂ (800 ml), EtOH (200 ml), and MeOH (400 ml). The product was then eluted with a mixture of 20% MeNH₂ (33% solution in EtOH) in 80% MeOH. Fractions containing the product were combined and evaporated to dryness. The residue was re-dissolved in a small volume of water and evaporated again (2-3 repeats) to afford the free amine form of NB125.

Analytically pure product was obtained by passing the above product through a short column of Amberlite CG50 ($NH_4^+$ form). The column was first washed with a mixture of MeOH/H₂O (3:2), then the product was eluted with a mixture of MeOH/H₂O/NH₄OH (80:10:10) to afford NB125 (0.398 grams, 79% yield).

For storage and biological tests, compound was converted to its sulfate salt form: the free base was dissolved in water, the pH was adjusted around 7.0 with H₂SO₄ (0.1 N) and lyophilized.

¹HNMR (500 MHz, CD₃OD): "Ring I" $\delta_H$ 1.22 (d, 3H, J=5.8 Hz, CH₃), 2.61 (dd, 1H, J₁=2.5, J₂=9.6 Hz, H-2'), 3.22 (t, 1H, J=9.8 Hz, H-4'), 3.50 (t, 1H, J=9.9 Hz, H-3'), 3.83 (dd, 1H, J₁=3.0, J₂=10.1 Hz, H-5'), 4.12 (m, 1H, H-6'), 5.20 (d, 1H, J=3.3 Hz, H-1'); "Ring II" $\delta_H$ 1.21 (ddd, 1H, J₁=J₂=J₃=12.5 Hz, H-2$_{ax}$), 1.98 (td, 1H, J₁=4.5, J₂=12.5 Hz, H-2$_{eq}$), 2.65 (m, 1H, H-1), 2.78 (m, 1H, H-3), 3.18 (t, 1H, J=9.3 Hz, H-6), 3.38 (t, 1H, J=9.1 Hz, H-4), 3.46 (t, 1H, J=9.2 Hz, H-5); "Ring III" $\delta_H$ 1.17 (d, 3H, J=6.4 Hz, CH₃), 3.10 (m, 1H, H-5"), 3.71 (t, 1H, J=5.0 Hz, H-4"), 4.06 (t, 1H, J=5.6 Hz, H-2"), 4.16 (t, 1H, J=3.0 Hz, H-3"), 5.20 (d, 1H, J=3.0 Hz, H-1").

¹³CNMR (125 MHz, CD₃OD): $\delta_C$ 16.6 (C-7"), 18.7 (C-6"), 37.6 (C-1), 49.5, 52.2, 52.5, 57.8, 67.8, 70.8, 73.6, 75.4, 76.1, 76.7, 78.4, 84.7, 87.5, 88.0, 101.9 (C-1'), 109.6 (C-1").

MALDI TOFMS calculated for $C_{19}H_{39}N_4O_{10}$ ([M+H]⁺) m/e: 483.3; measured m/e: 483.2.

Preparation of 6'-(R)-Methyl-5-O-(5-amino-5,6-dideoxy-α-L-talofuranosyl)-1-N-[(S)-4-amino-2-hydroxy-butanoyl]paromamine (NB127)

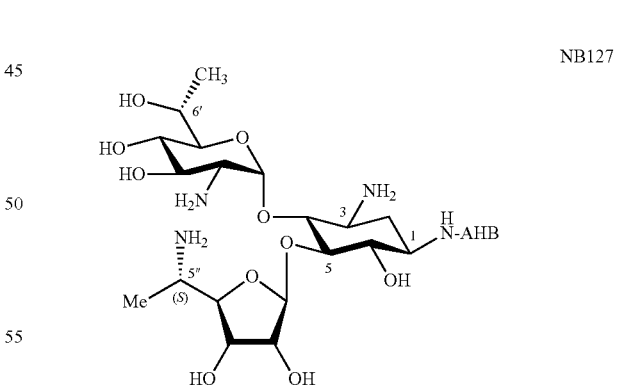

NB127

The glycosylation product Compound (S)-223 (1.05 grams, 0.001 mol) was treated with a solution of MeNH₂ (33% solution in EtOH, 50 ml) and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which PMe₃ (1 M solution in THF, 5.0 ml, 5.0 mmol) was added. The reaction progress was monitored by TLC [CH$_2$Cl$_2$/MeOH/ H$_2$O/MeNH$_2$ (33% solution in EtOH) 10:15:6:15], which indicated completion after 1 hour. The product was purified by column chromatography on a short column of silica gel. The column was washed with the following solvents: THF (800 ml), CH$_2$Cl$_2$ (800 ml), EtOH (200 ml), and MeOH (400 ml). The product was then eluted with a mixture of 20% MeNH$_2$ (33% solution in EtOH) in 80% MeOH. Fractions containing the product were combined and evaporated to dryness. The residue was re-dissolved in a small volume of water and evaporated again (2-3 repeats) to afford the free amine form of NB127.

Analytically pure product was obtained by passing the above product through a short column of Amberlite CG50 (NH$_4^+$ form). The column was first washed with a mixture of MeOH/H$_2$O (3:2), then the product was eluted with a mixture of MeOH/H$_2$O/NH$_4$OH (80:10:10) to afford NB 127 (0.480 grams, 86% yield).

For storage and biological tests, compound was converted to its sulfate salt form: the free base was dissolved in water, the pH was adjusted around 7.0 with H$_2$SO$_4$ (0.1 N) and lyophilized.

$^1$HNMR (500 MHz, CD$_3$OD) "Ring I" $\delta_H$ 1.21 (d, 3H, J=6.0 Hz, CH$_3$), 2.63 (dd, 1H, J$_1$=3.5, J$_2$=10.0 Hz, H-2'), 3.23 (t, 1H, J=8.9 Hz, H-4'), 3.52 (t, 1H, J=9.9 Hz, H-3'), 3.82 (dd, 1H, J$_1$=3.0, J$_2$=10.0 Hz, H-5'), 4.13 (m, 1H, H-6'), 5.22 (d, 1H, J=3.3 Hz, H-1'); "Ring II" $\delta_H$ 1.34 (ddd, 1H, J$_1$=J$_2$=J$_3$=12.5 Hz, H-2$_{ax}$), 1.99 (td, 1H, J$_1$=4.5 and J$_2$=12.5 Hz, H-2$_{eq}$), 2.85 (m, 1H, H-3), 3.40 (t, 1H, J=8.8 Hz, H-4), 3.50-3.59 (m, 2H, H-5 and H-6), 3.83 (m, 1H, H-1); "Ring III" $\delta_H$ 1.17 (d, 3H, J=6.6 Hz, CH$_3$), 2.94 (m, 1H, H-5"), 3.56 (t, 1H, J=7.1 Hz, H-4"), 4.01 (t, 1H, J=5.7 Hz, H-3"), 4.09 (dd, 1H, J$_1$=2.7 and J$_2$=5.4 Hz, H-2"), 5.26 (d, 1H, J=2.5 Hz, H-1"). Additional peaks in the spectrum were identified as follows: $\delta_H$ 1.82 (m, 1H, H-8), 1.95 (m, 1H, H-8), 2.83 (t, 2H, J=5.7 Hz, H-9 and H-9), 4.13 (dd, 1H, J$_1$=4.2 and J$_2$=7.6 Hz, H-7).

$^{13}$CNMR (125 MHz, CD$_3$OD): $\delta_C$ 16.6 (C-7'), 19.2 (C-6"), 35.9, 37.8, 39.0, 50.8, 50.9, 52.3, 57.8, 67.8, 71.7, 72.4, 73.6, 75.5, 75.6, 76.3, 76.8, 84.8, 86.7, 88.6, 101.9 (C-1'), 110.0 (C-1"), 177.1 (C=O).

MALDI TOFMS calculated for C$_{23}$H$_{45}$N$_5$O$_{12}$Na ([M+Na]$^+$) m/e: 606.3; measured m/e: 606.6.

Preparation of 6'-(R)-Methyl-5-O-(5-amino-5,6-dideoxy-β-D-allofuranosyl)-1-N-[(S)-4-amino-2-hydroxy-butanoyl]paromamine (NB128)

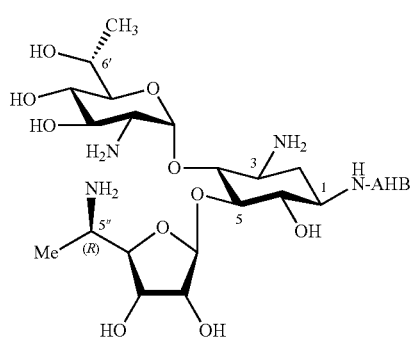

NB128

The glycosylation product Compound (R)-224 (1.12 grams, 0.001 mol) was treated with a solution of MeNH$_2$ (33% solution in EtOH, 50 ml) and the reaction progress was monitored by TLC (EtOAc/MeOH 85:15), which indicated completion after 8 hours. The reaction mixture was evaporated to dryness and the residue was dissolved in a mixture of THF (5 ml) and aqueous NaOH (1 mM, 5.0 ml). The mixture was stirred at room temperature for 10 minutes, after which PMe$_3$ (1 M solution in THF, 5.0 ml, 5.0 mmol) was added. The reaction progress was monitored by TLC [CH$_2$Cl$_2$/MeOH/ H$_2$O/MeNH$_2$ (33% solution in EtOH) 10:15:6:15], which indicated completion after 1 hour. The product was purified by column chromatography on a short column of silica gel. The column was washed with the following solvents: THF (800 ml), CH$_2$Cl$_2$ (800 ml), EtOH (200 ml), and MeOH (400 ml). The product was then eluted with a mixture of 20% MeNH$_2$ (33% solution in EtOH) in 80% MeOH. Fractions containing the product were combined and evaporated to dryness. The residue was re-dissolved in a small volume of water and evaporated again (2-3 repeats) to afford the free amine form NB128.

Analytically pure product was obtained by passing the above product through a short column of Amberlite CG50 (NH$_4^+$ form). The column was first washed with a mixture of MeOH/H$_2$O (3:2), then the product was eluted with a mixture of MeOH/H$_2$O/NH$_4$OH (80:10:10) to afford NB128 (0.500 grams, 84% yield).

For storage and biological tests, compound was converted to its sulfate salt form: the free base was dissolved in water, the pH was adjusted around 7.0 with H$_2$SO$_4$ (0.1 N) and lyophilized.

$^1$HNMR (500 MHz, CD$_3$OD) "Ring I" $\delta_H$ 1.22 (d, 3H, J=6.3 Hz, CH$_3$), 2.63 (dd, 1H, J$_1$=3.8, J$_2$=10.0 Hz, H-2'), 3.22 (t, 1H, J=9.8 Hz, H-4'), 3.52 (dd, 1H, J$_1$=8.6, J$_2$=10.3 Hz, H-3'), 3.83 (dd, 1H, J$_1$=3.1, J$_2$=10.2 Hz, H-5'), 4.13 (m, 1H, H-6'), 5.23 (d, 1H, J=3.7 Hz, H-1'); "Ring II" $\delta_H$ 1.34 (ddd, 1H, J$_1$=J$_2$=J$_3$=12.5 Hz, H-2$_{ax}$), 1.99 (td, 1H, J$_1$=4.5 and J$_2$=12.5 Hz, H-2$_{eq}$), 2.85 (m, 1H, H-3), 3.39 (t, 1H, J=8.8 Hz, H-4), 3.49-3.56 (m, 2H, H-5 and H-6), 3.82 (m, 1H, H-1); "Ring III" $\delta_H$ 1.16 (d, 3H, J=6.7 Hz, CH$_3$), 3.08 (m, 1H, H-5"), 3.69 (t, 1H, J=5.5 Hz, H-4"), 4.07 (dd, 1H, J$_1$=2.1, J$_2$=5.2 Hz, H-2"), 4.14 (t, 1H, J=5.7 Hz, H-3"), 5.21 (d, 1H, J=3.7 Hz, H-1"). Additional peaks in the spectrum were identified as follows: $\delta_H$ 1.82 (m, 1H, H-8), 1.95 (m, 1H, H-8), 2.84 (t, 2H, J=7.2 Hz, H-9 and H-9), 4.13 (dd, 1H, J$_1$=3.9, J$_2$=7.5 Hz, H-7).

$^{13}$CNMR (125 MHz, CD$_3$OD): $\delta_H$ 16.6 (C-7'), 18.8 (C-6"), 36.0, 37.7, 38.9, 49.6, 50.8, 52.3, 57.8, 67.8, 71.0, 71.7, 73.6, 75.5 (2C), 76.2, 76.7, 85.0, 86.9, 87.9, 101.9 (C-1'), 110.0 (C-1"), 177.1 (C=O).

MALDI TOFMS calculated for C$_{23}$H$_{45}$N$_5$O$_{12}$Na ([M+Na]$^+$) m/e: 606.3; measured m/e: 606.6.

Example 2

Stop Codon Readthrough

As presented hereinabove, the efficiency of aminoglycosides-induced readthrough is highly dependent on: (i) the identity of stop codon (UGA>UAG>UAA), (ii) the identity of the first nucleotide immediately downstream from the stop codon (C>U>A≥G) and (iii) the local sequence context around the stop codon. Therefore, in attempts to provide broad understanding on structure-activity relationship of the designed structures, a variety of constructs containing different sequence contexts around premature stop codons were used. These exemplary sequences were derived from the PCDH15, CFTR, IDUA and Dystrophin genes that underlie USH1, CF, HS and DMD, respectively. The prevalent nonsense mutations of these diseases that were chosen were: R3X and R245X for USH1, G542X and W1282X for CF, Q70X for HS and R3381X for DMD, as presented hereinbelow.

Readthrough Assays:

DNA fragments derived from PCDH15, CFTR, Dystrophin and IDUA cDNAs, including the tested nonsense mutation or the corresponding wild type (wt) codon, and four to six upstream and downstream flanking codons were created by annealing following pairs of complementary oligonucleotides:

```
Usher Syndrome:
    (wild type sequence SEQ ID NO: 1 andSEQ ID NO: 2)
p.R3Xmut/wt
5'-GATCCCAGAAGATGTTTCGACAGTTTTATCTCTGGACAGAGCT-3',
and
5'-CTGTCAGAGATAAAACTGTCGAAACATCTTCTG-3';

(mutant sequence SEQ ID NO: 3 and SEQ ID NO: 4)
GATCCCAGAAGATGTTTTGACAGTTTTATCTCTGGACAGAGCT
and
5'-CTGTCAGAGATAAAACTGTCAAAACATCTTCTG-3'.

p.R245Xmut/wt
                    (WT sequence SEQ ID NO: 5 and 6)
5'-GATCCAAAATCTGAATGAGAGGCGAACCACCACCACCCTCGAG
CT-3'
and
5'-CGAGGGTGGTGGTGGTTGTTCGCCTCTCATTCAGATTTTG-3';

(mutant sequence SEQ ID NO: 7 and SEQ ID NO: 8)
5'-GATCCAAAATCTGAATGAGAGGTGAACCACCACCACCCTCGAG
CT
and
5'-CGAGGGTGGTGGTGGTTGTTCACCTCTCATTCAGATTTTG-3'.

Cystic Fibrosis:
p. G542Xmut/wt
 (wild type sequence SEQ ID NO: 9 and SEQ ID NO: 10)
5'-TCGACCAATATAGTTCTTGGAGAAGGTGGAATCGAGCT-3'
and
5'-CGATTCCACCTTCTCGAAGAACTATATTGG-3';

(mutant sequence SEQ ID NO: 11 and SEQ ID NO: 12)
5'-TCGACCAATATAGTTCTTTGAGAAGGTGGAATCGAGCT-3'
5'-CGATTCCACCTTCTCAAAGAACTATATTGG-3'.

p. W1282Xmut/wt
                    (WT sequence SEQ ID NOs: 13 and 14)
5'-TCGACAACTTTGCAACAGTGGAGGAAAGCCTTTGAGCT-3'
and
5-CAAAGGCTTTCCTCCACTGTTGCAAAGTTG-3';

(mutant sequence SEQ ID NO: 15 and SEQ ID NO: 16)
5'-TCGACAACTTTGCAACAGTGAAGGAAAGCCTTTGAGCT-3'
and
5-CAAAGGCTTTCCTTCACTGTTGCAAAGTTG-3'.

Duchene Muscular Dystrophy (DMD):
p.R3381Xmut/wt
(wild type sequence SEQ ID NO: 17 and SEQ ID NO:
 18)
5'-TCGACAAAAAACAAATTTTGCACCAAAAGGTATGAGCT-3'
and
5'-CATACCTTTTGGTGCAAAATTTGTTTTTTG-3';

(mutant sequence SEQ ID NO: 19 and SEQ ID NO: 20)
5'-TCGACAAAAAACAAATTTTGAACCAAAAGGTATGAGCT-3'
and
5'-CATACCTTTTGGTTCAAAATTTGTTTTTTG-3'.

Hurler Syndrome:
p. Q70Xmut/wt
(wild type sequence SEQ ID NO: 21 and SEQ ID NO:
 22)
5'-TCGACCCTCAGCTGGGACCAGCAGCTCAACCTCGAGCT-3'
and
5'-CGAGGTTGAGCTGCTGGTCCCAGCTGAGG-3';

(mutant sequence SEQ ID NO: 23 and SEQ ID NO: 24)
5'-TCGACCCTCAGCTGGGACTAGCAGCTCAACCTCGAGCT-3'
and
5'-CGAGGTTGAGCTGCTAGTCCCAGCTGAGG-3'.
```

The fragments were inserted in frame into the polylinker of the p2Luc plasmid between either BamHI and SacI (p.R3X and p.R245X), or SalI and SacI (all the rest) restriction sites.

For the in vitro readthrough assays, the obtained plasmids, with addition of the tested aminoglycosides were transcribed and translated using the TNT Reticulocyte Lysate Quick Coupled Transcription/Translation System. Luciferase activity was determined after 90 minutes of incubation at 30° C., using the Dual Luciferase Reporter Assay System (Promega™).

For the ex vivo readthrough assays, the constructs harboring the R3X, R245X, Q70X and W1282X mutations were transfected to HEK-293 cells with Lipofectamine 2000 (Invitrogen) and addition of the tested compounds was performed 6 hours post transfection. The cells were harvested following 16 hours of incubation with the tested aminoglycosides. Stop codon readthrough was calculated as previously described (see, Grentzmann, G. et al., RNA, 1998, 4, p. 479.).

Readthrough Results:

Initially, the influence of the chiral C5"-methyl group on readthrough potential was evaluated on the pseudo-trisaccharides NB118 and NB119 by using a dual luciferase reporter assay system as described hereinabove. Briefly, DNA fragments were cloned between BamHI and SacI restriction sites of the p2luc vector and the obtained constructs were transcribed and translated using TNT quick coupled transcription/translation system. The amount of the translated products was evaluated using the dual luciferase reporter assay system and used to calculate the suppression level. The results, which represent averages of at least three independent experiments, are summarized in FIGS. 2A-F.

FIGS. 2A-F present the results of the stop codon readthrough assay showing comparative graphs of in vitro stop codon suppression levels induced by NB30 (marked by empty circles), NB118 (marked by black triangles), NB119 (marked by empty triangles) and the control drug gentamicin (marked by black rectangles) in a series of nonsense mutation context constructs representing various genetic diseases (in parenthesis), wherein results pertaining to the R3X (USH1) construct are shown in FIG. 2A, R245X (USH1) in FIG. 2B, G542X (CF) in FIG. 2C, W1282X (CF) in FIG. 2D, Q70X (HS) in FIG. 2E, and wherein results pertaining to the R3381X (DMD) construct are shown in FIG. 2F.

As can be seen in Figures A-F 2, in all the mutations tested, installation of (S)-5"-methyl group, as in NB118), on NB30 dramatically increases its in vitro readthrough activity, whereas that of the (R)-5"-methyl group, as in NB119), is comparatively small. In addition, in all mutations tested (except G542X, see FIG. 2C), the readthrough activity of NB118 was significantly better than that of the clinical drug gentamicin.

The same potency enhancement, attributed to the addition of the (S)-5"-methyl group, was explored in the case of NB54. To evaluate the impact of the stereochemistry at C5"-position, both C5"-diastereomers were synthesized, namely NB122 and NB123. Comparative in vitro suppression tests of the pseudo-trisaccharides NB54, NB122, NB123, and the control drug gentamicin were performed under the same experimental conditions as described hereinabove for compounds NB30, NB54 and NB118, and the observed data (averages of at least three independent experiments) are presented in FIGS. 3A-F.

FIGS. 3A-F present the results of the stop codon readthrough assay showing comparative graphs of in vitro stop codon suppression levels induced by NB54 (marked by black circles), NB122 (marked by black triangles), NB123 (marked by empty triangles) and gentamicin (marked by black rectangles) in a series of nonsense mutation context constructs representing various genetic diseases (in parenthesis), wherein results pertaining to the R3X (USH1) construct are shown in FIG. 3A, R245X (USH1) in FIG. 3B, G542X (CF) in FIG. 3C, W1282X (CF) in FIG. 3D, Q70X (HS) in FIG. 3E, and wherein results pertaining to the R3381X (DMD) construct are shown in FIG. 3F.

As can be seen in FIGS. 3A-F, the efficacy of readthrough is substantially different between different constructs and compounds tested, with no obvious dependence of readthrough effectiveness on the introduced type of modification on aminoglycoside. Nevertheless, in all mutations tested (except R3X and Q70X, FIG. 3A and FIG. 3E), NB122 induced the highest level of readthrough, followed by NB123, NB54, and gentamicin. The UGA C tetracodon sequence (R3X) showed the best translational readthrough than UGA A and UGA G, with the UAG C tetracodon least efficient, in agreement with earlier observations.

To further evaluate the readthrough potential of NB122 and NB123, their activity was assayed in cultured mammalian cells using four different dual luciferase reporter plasmids harboring the PCDH15-R3X and PCDH15-R245X nonsense mutation of USH1, the IDUA-Q70X nonsense mutation of HS, and the CFTR-W1282X nonsense mutation of CF. These reporter constructs were the same as presented hereinabove for the in vitro study, and have distinct advantage to control for differences in mRNA levels between normal and nonsense-containing sequences over those of single reporter or direct protein analysis.

The constructs were transfected into a human embryonic kidney cell line (HEK-293) and incubated with varying concentrations of NB122, NB123, NB54 and the control drug gentamicin, and the results are presented in FIGS. 4A-D.

FIGS. 4A-D present ex vivo suppression of the PCDH15-R3X (FIG. 4A), PCDH15-R245X (FIG. 4B), IDUA-Q70X (FIG. 4C), and CFTR-W1282X (FIG. 4D) nonsense mutations, effected by NB54 (marked by black circles), NB122 (marked by black triangle), NB123 (marked by empty triangles) and the control drug gentamicin (marked by black rectangles).

As described hereinabove, the constructs of p2luc plasmid harboring the R3X, R245X, Q70X and W1282X mutations were transfected to HEK-293 cells using Lipofectamine2000 and the tested compounds were added 6 hours post transfection. Cells were harvested after 16 hours incubation and luciferase activity was determined using the dual luciferase reporter assay system (Promega™). Stop codon readthrough was calculated as described previously, and the results are averages of at least three independent experiments.

As can be seen in FIGS. 4A-D, in all the mutations tested, the observed efficacy of aminoglycoside-induced readthrough was in the order NB122≥NB123>NB54>gentamicin. This trend for NB122 and NB123 was similar to that observed for the suppression of the same stop mutations in vitro (see, FIGS. 3A-F), even though the gap of potency difference between NB122 and NB123 was smaller than the one observed for the suppression of the same mutations in cell-free extracts.

The significantly higher readthrough potencies observed for both NB122 and NB123, over that of NB54 in R3X and Q70X (see, FIG. 4A and FIG. 4C), was considerably different to those of the same mutations in vitro (FIG. 3A and FIG. 3E). This data may point to a better cell permeability of both NB122 and NB123 over that of NB54, due to the presence of the 5"-methyl group.

Several combinations of the aforementioned pharmacophore points into one molecule including N1-AHB with (R)-6'-methyl group gave the know compound NB84, and N1-AHB with (S)- and (R)-5"-methyl groups gave the exemplary compounds according to some embodiments of the present invention, NB122 and NB123. All these exemplary compounds have been shown to exhibit significantly improved readthrough activity than the parent structures while the cytotoxicity of the resulting novel structures did not change significantly. One of the objectives of the present study was to test additional combinations of the above elements. As such the combination of (R)-6'-methyl group with either (S)-5"-methyl group or (R)-5"-methyl group into one molecule. For that end exemplary compounds NB124 and NB125 have been prepared and tested. The combination of the latter two chiral methyl groups with N1-AHB group gave two exemplary compounds NB127 and NB128.

As in the previous series, the influence of two chiral methyl groups on readthrough potential was evaluated in vitro on the pseudo-trisaccharides NB124 [(R)-6', (S)-5"] and NB125 [(R)-6', (R)-5"] by using a dual luciferase reporter assay system as described hereinabove, and the results are presented in FIGS. 5A-B and FIGS. 6A-F.

FIGS. 5A-D present comparative plots of results of in vitro premature stop codon mutation suppression assays of the CFTR-G542X (FIG. 5A and FIG. 5C), CFTR-W1282X (FIG. 5B and FIG. 5D) effected by exemplary compounds according to some embodiments of the present invention NB124 (marked by black circles), NB125 (marked by empty circles), NB127 (marked by black triangles), NB128 (marked by empty triangles), NB74 (marked by empty rhombs) NB84 (marked by black rhombs), and the control drugs gentamicin (marked by black rectangles) and G418 (marked by empty rectangles).

FIGS. 6A-F present the results of the stop codon readthrough assay showing comparative graphs of in vitro stop codon readthrough levels induced by NB124 (marked by black circles), NB125 (marked by empty circles), NB74 (marked by empty rhombs) and the control drug gentamicin (marked by black rectangles) in a series of nonsense mutation context constructs representing various genetic diseases (in parenthesis), wherein results pertaining to the R3X (USH1) construct are shown in FIG. 6A, R245X (USH1) in FIG. 6B, G542X (CF) in FIG. 6C, W1282X (CF) in FIG. 6D, Q70X (HS) in FIG. 6E, and wherein results pertaining to the R3381X (DMD) construct are shown in FIG. 6F.

As can be seen in FIGS. 5A-B and FIGS. 6A-F, the addition of the (S)-5"-methyl group on the structure of the known compound NB74 to afford NB124 increases its in vitro readthrough activity significantly, whereas that of the (R)-5"-methyl group (in compound NB125) is smaller comparatively. In addition, in all mutations tested the readthrough activity of NB124 was improved significantly compared to that of the clinical drug gentamicin. Thus, the two methyl groups (R)-6'-methyl and (S)-5"-methyl in compound NB124 are operating additively or synergistically to enhance readthrough activity in comparison to NB30, NB74 and NB118. The conversions of either NB30 to NB74 to NB124 (namely the addition of first (R)-6'-methyl group on NB30 to yield NB74 and than further addition of (S)-5"-methyl on NB74 to yield NB124), or NB30 to NB118 to NB124 (namely the addition of first (S)-5"-methyl group on NB30 to yield NB118 and than further addition of (R)-6'-methyl group on NB118 to yield NB124), are affecting additively to increase the observed activity of the resulted structures in a step-wise manner.

Interestingly, similar additive effect was also observed when the above two methyl groups in NB124 and NB125 were combined with the N1-AHB group to yield the compounds NB127 and NB128, respectively, as presented in FIGS. 5C-D and FIGS. 7A-F.

FIGS. 7A-F present the results of the stop codon readthrough assay showing comparative graphs of in vitro stop codon suppression levels induced by NB84 (marked by black rhombs), NB127 (marked by black triangles), NB128 (marked by empty triangles), G418 (marked by empty rectangles) and gentamicin (marked by black rectangles) in a series of nonsense mutation context constructs representing various genetic diseases (in parenthesis), wherein results pertaining to the R3X (USH1) construct are shown in FIG. 7A, R245X (USH1) in FIG. 7B, G542X (CF) in FIG. 7C, W1282X (CF) in FIG. 7D, Q70X (HS) in FIG. 7E, and wherein results pertaining to the R3381X (DMD) construct are shown in FIG. 7F.

As can be seen in FIGS. 5C-D and FIGS. 7A-F, NB127 which contains (S)-5''-methyl group is significantly potent than the NB128 containing (R)-5''-methyl group. In addition, both NB127 and NB128 are significantly stronger readthrough inducers than the corresponding counterparts not possessing an AHB moiety in the N1 position (namely NB124 and NB125) and the compound NB84 that contains only (R)-6'-mathyl and N1-AHB.

It is noted herein that in several mutations contests tested, such as G542X, W1282X and Q70X, NB127 exhibited similar or greater activity than that of G418, and further that in all the in vitro tests performed to date, G418 is considered the strongest readthrough inducer. The observation that NB127 can surpasses G416 activity, while exhibiting far lower cell toxicity than that of G418 (see the Table 2) demonstrates the benefits conferred by compounds according to some embodiments of the present invention.

Figure 8:
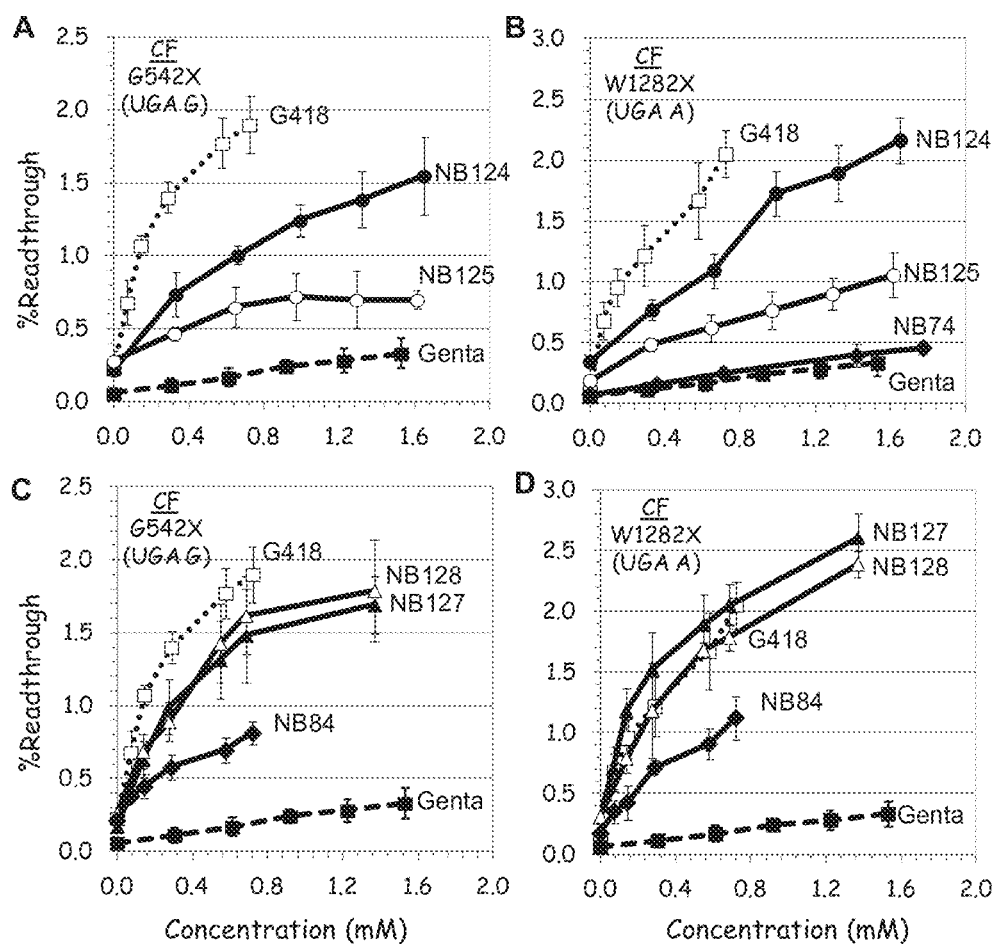
Figure 9:
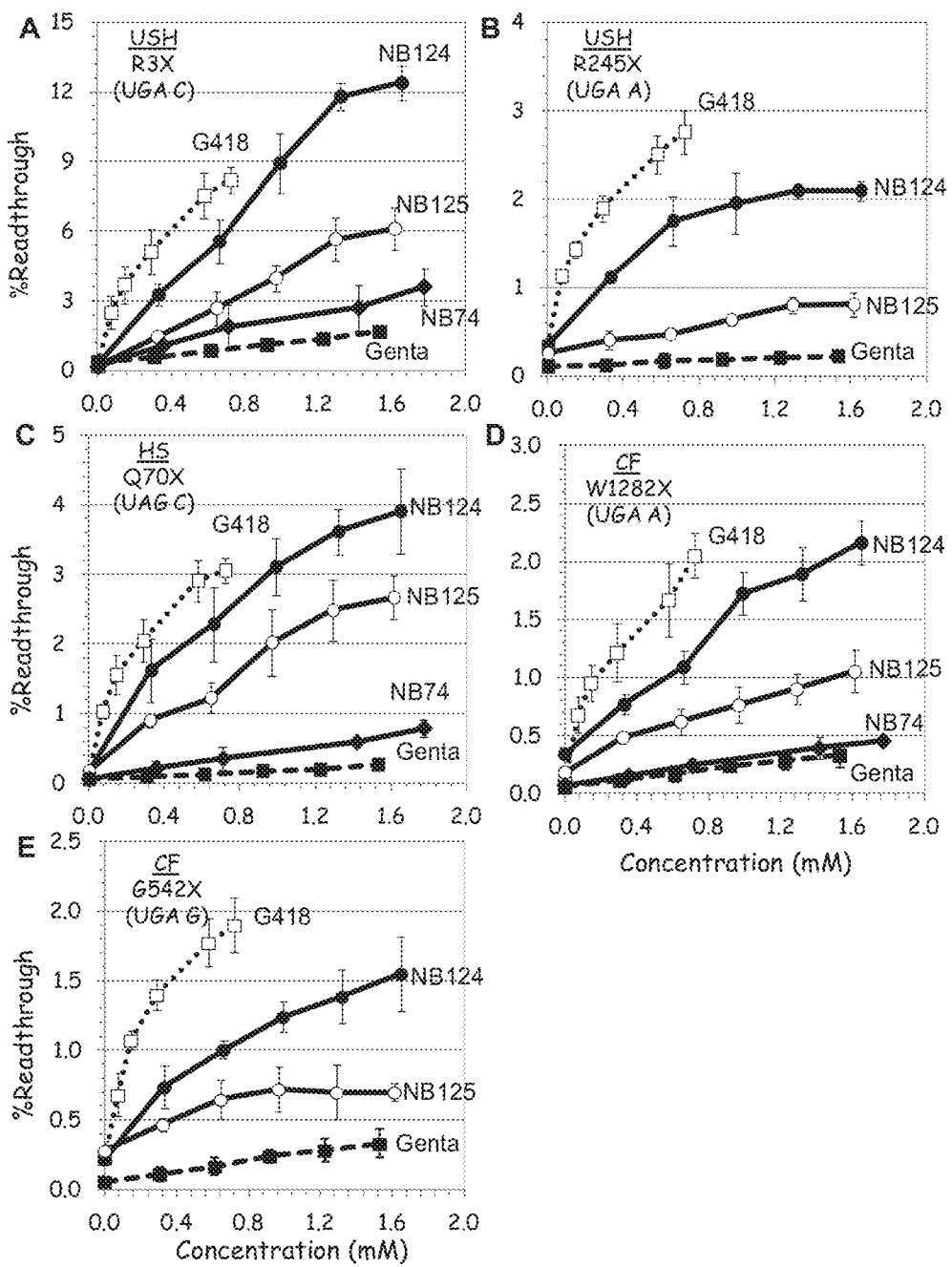
Figure 10:
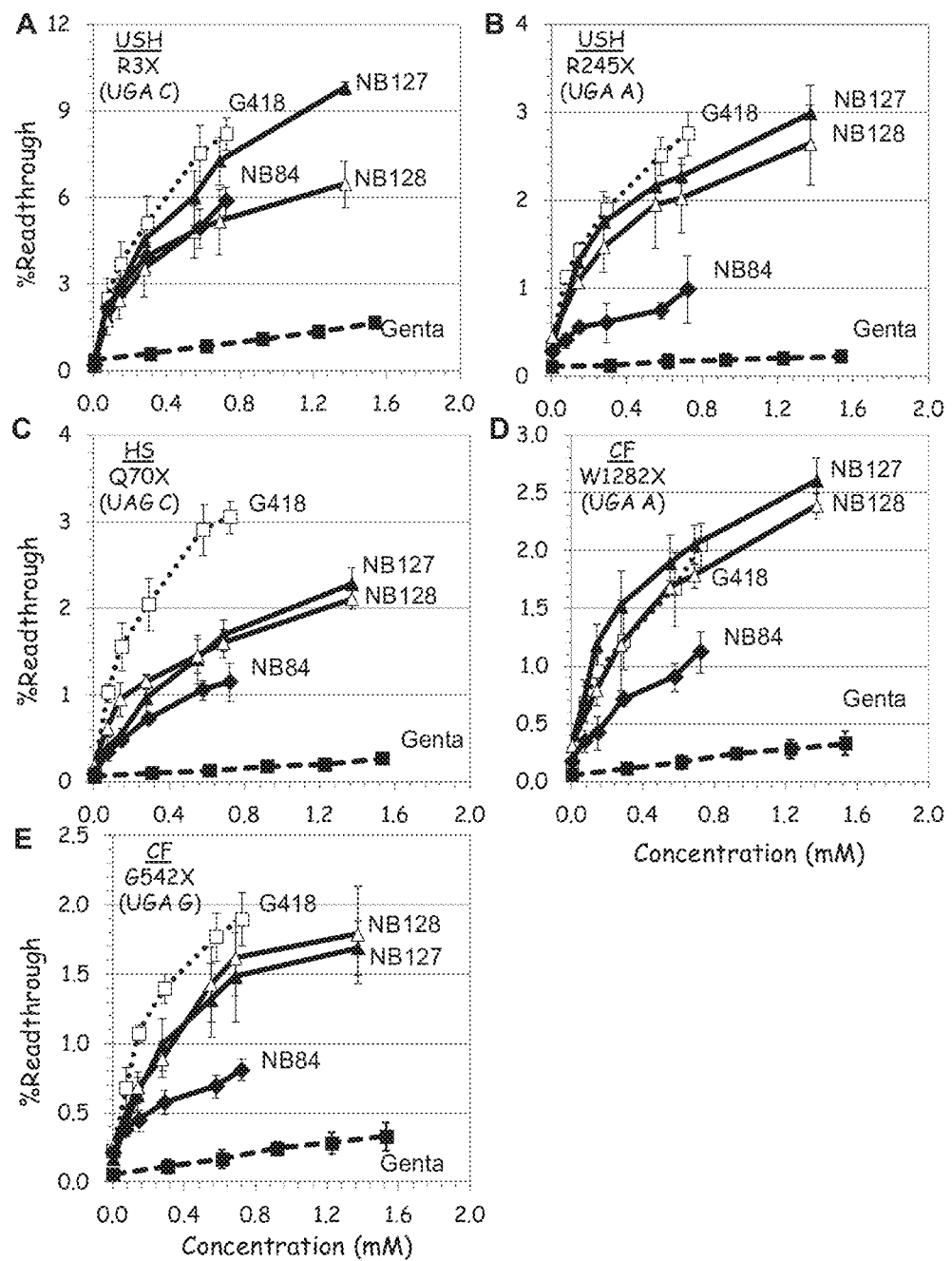

The observed in vitro activity data is further supported by ex vivo comparative activity tests shown in FIGS. 8-10.

FIGS. 8A-D present comparative plots of results of ex vivo premature stop codon mutation suppression assays conducted for the construct CFTR-G542X (FIGS. 8A and 8C), CFTR-W1282X (FIGS. 8B and 8D) effected by NB124 (marked by black circles), NB125 (marked by empty circles), NB127 (marked by black triangles), NB128 (marked by empty triangles), NB74 (marked by empty rhombs) NB84 (marked by black rhombs) and the control drugs gentamicin (marked by black rectangles) and G418 (marked by empty rectangles).

FIGS. 9A-E present the results of the stop codon readthrough assay showing comparative graphs of ex vivo stop codon suppression levels induced by NB124 (marked by black circles), NB125 (marked by empty circles), NB74 (marked by black rhombs) and the control drugs gentamicin (marked by black rectangles) and G418 (marked by empty rectangles) in a series of nonsense mutation context constructs representing various genetic diseases (in parenthesis), wherein results pertaining to the R3X (USH1) construct are shown in FIG. 9A, R245X (USH1) in FIG. 9B, Q70X (HS) in FIG. 9C, W1282X (CF) in FIG. 9D and G542X (CF) in FIG. 9E.

FIGS. 10A-E present the results of the stop codon readthrough assay showing comparative graphs of ex vivo stop codon suppression levels induced by NB127 (marked by black rectangles), NB128 (marked by empty triangles), NB84 (marked by black rhombs) and the control drugs gentamicin (marked by black rectangles) and G418 (marked by empty rectangles) in a series of nonsense mutation context constructs representing various genetic diseases (in parenthesis), wherein results pertaining to the R3X (USH1) construct are shown in FIG. 10A, R245X (USH1) in FIG. 10B, Q70X (HS) in FIG. 10C, W1282X (CF) in FIG. 10D and G542X (CF) in FIG. 10E.

As can be seen in FIGS. 8-10, in all the mutations tested, the observed efficacy of aminoglycoside-induced readthrough was in the order of NB124>NB125>NB74>gentamicin and NB127≥NB128>NB84>gentamicin. These trends are similar to those observed for the suppression of the same stop mutations in vitro (see, FIGS. 5-7), even though the gap of potency difference between the NB127 and NB128 was smaller than the one observed for the suppression of the same mutations in vitro in cell-free extracts.

Example 3

Cell Toxicity Vs. Readthrough

In order to ensure suitable cell viability for each of the tested compounds at the concentrations tested, cell toxicity was evaluated for each compound by measuring the half-maximal-lethal concentration value ($LC_{50}$ values) in HEK-293 and HFF (human foreskin fibroblasts) cells.

The percentages of cell viability were calculated as the ratio between the numbers of living cells in cultures grown in the presence of the tested compounds, versus cultures grown under the identical protocol but without the tested compound. The results represent averages of at least three independent experiments.

FIGS. 11A-D present semi-logarithmic plots of in vitro translation inhibition in prokaryotic (marked by black circles) and eukaryotic (marked by empty circles) systems measured for NB118 (FIG. 11A), NB119 (FIG. 11B) NB122 (FIG. 11C) and NB123 (FIG. 11D).

FIGS. 12A-D present semi-logarithmic plots of the percentages of ex vivo cell viability versus concentration of the tested compound in HEK-293 (FIG. 12A and FIG. 12C) and in human foreskin fibroblasts (HFF) (FIG. 12B and FIG. 12D) cells, for gentamicin (marked by empty rectangles), NB118 (marked by empty circles), NB119 (marked by black circles), NB122 (marked by empty triangles), and NB123 (marked by black triangle).

The half-maximal lethal concentration ($LC_{50}$) values were obtained from fitting concentration-response curves to the data of at least three independent experiments, using GraFit 5 software.

Prokaryotic and eukaryotic translation inhibition was quantified in coupled transcription/translation assays by using active luciferase detection, performed as described hereinabove. The MIC values were determined by using the double-microdilution method, with two different starting concentrations of each tested compound (384 μg/mL and 6,144 μg/mL). All the experiments were performed in duplicates and analogous results were obtained in three different experiments. In all biological tests, all tested aminoglycosides were in their sulfate salt forms. The concentrations reported refer to that of the free amine form of each aminoglycoside.

Table 1 presents comparative cell toxicity, eukaryotic and prokaryotic translation inhibition, and antibacterial activity assays obtain for gentamicin, paromomycin, the previously reported NB30 and NB54, and the exemplary compounds NB118, NB119, NB122 and NB123.

TABLE 1

| Antibacterial activity MIC (μM) | | Translation inhibition | | Cell toxicity LC$_{50}$ (mM) | | |
|---|---|---|---|---|---|---|
| | | Prokaryotic system | Eukaryotic System | | | |
| B. subtilis ATCC6633 | E. coli R477/100 | IC$_{50}$ (nM) | IC$_{50}$ (μM) | HFF | HEK-293 | Aminoglycoside |
| <0.75 | 6 | 28 ± 4 | 62 ± 9 | 3.2 ± 0.3 | 2.5 ± 0.3 | Gentamicin |
| 1.2 | 22 | 51 ± 5 | 57 ± 4 | 3.1 ± 0.4 | 4.1 ± 0.5 | Paromomycin |
| 100 | 790 | 460 ± 50 | 31 ± 4 | 21.8 ± 0.9 | 21.4 ± 3.9 | NB30 |
| 70 | 588 | 160 ± 20 | 24 ± 1 | 7.8 ± 0.4 | 6.1 ± 0.6 | NB54 |
| 83 | 2659 | 1960 ± 206 | 16 ± 1.3 | 21.8 ± 0.5 | 23.5 ± 0.6 | NB118 |
| 78 | 4989 | 2132 ± 478 | 28 ± 1.1 | 20.1 ± 0.6 | 19.8 ± 0.4 | NB119 |
| 33 | 1067 | 2266 ± 196 | 5.2 ± 0.7 | 8.1 ± 1.4 | 10.1 ± 0.8 | NB122 |
| 33 | 1057 | 811 ± 59 | 4.6 ± 0.6 | 19.3 ± 1.5 | 13.9 ± 1.3 | NB123 |

Figure 2:
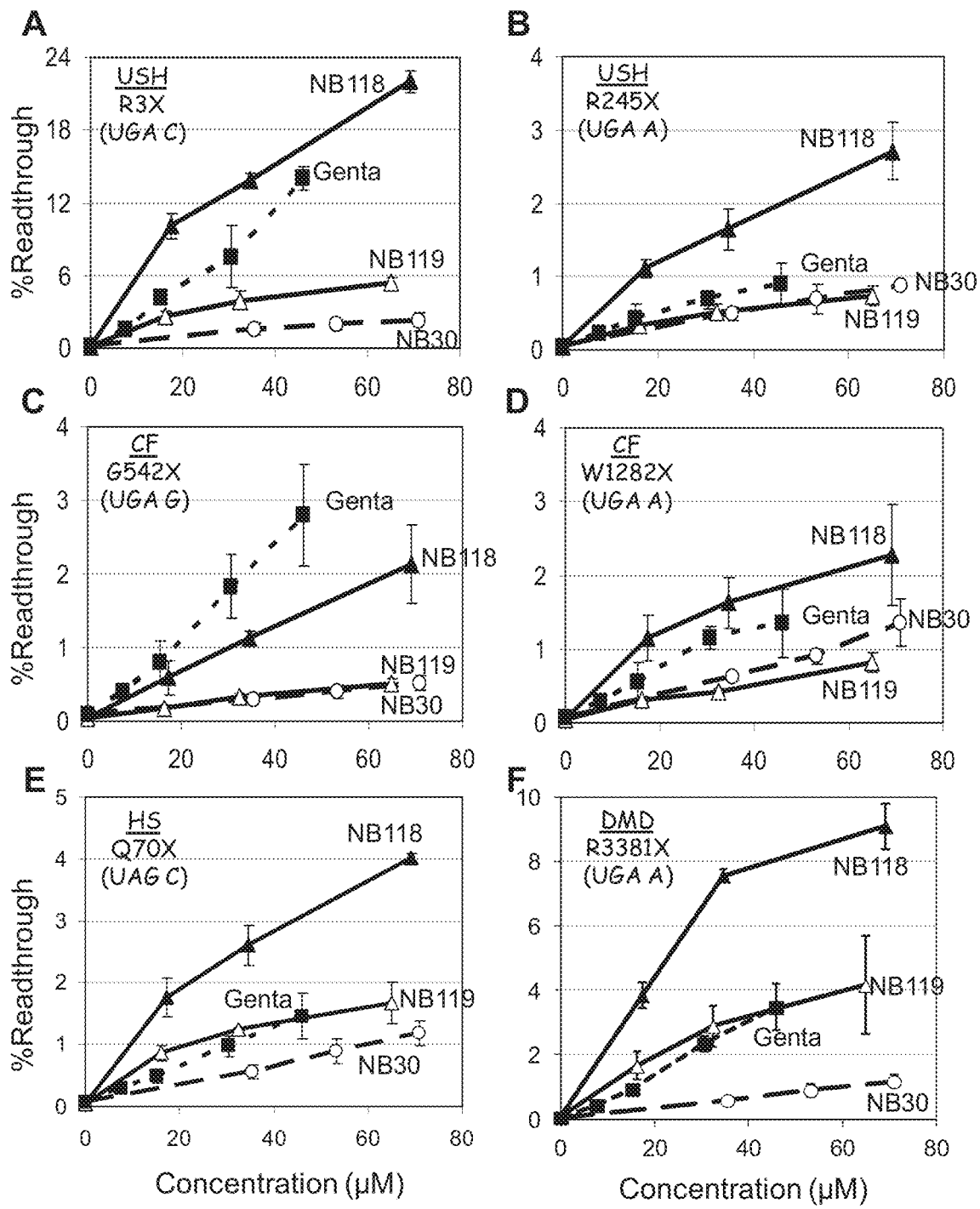
Figure 3:
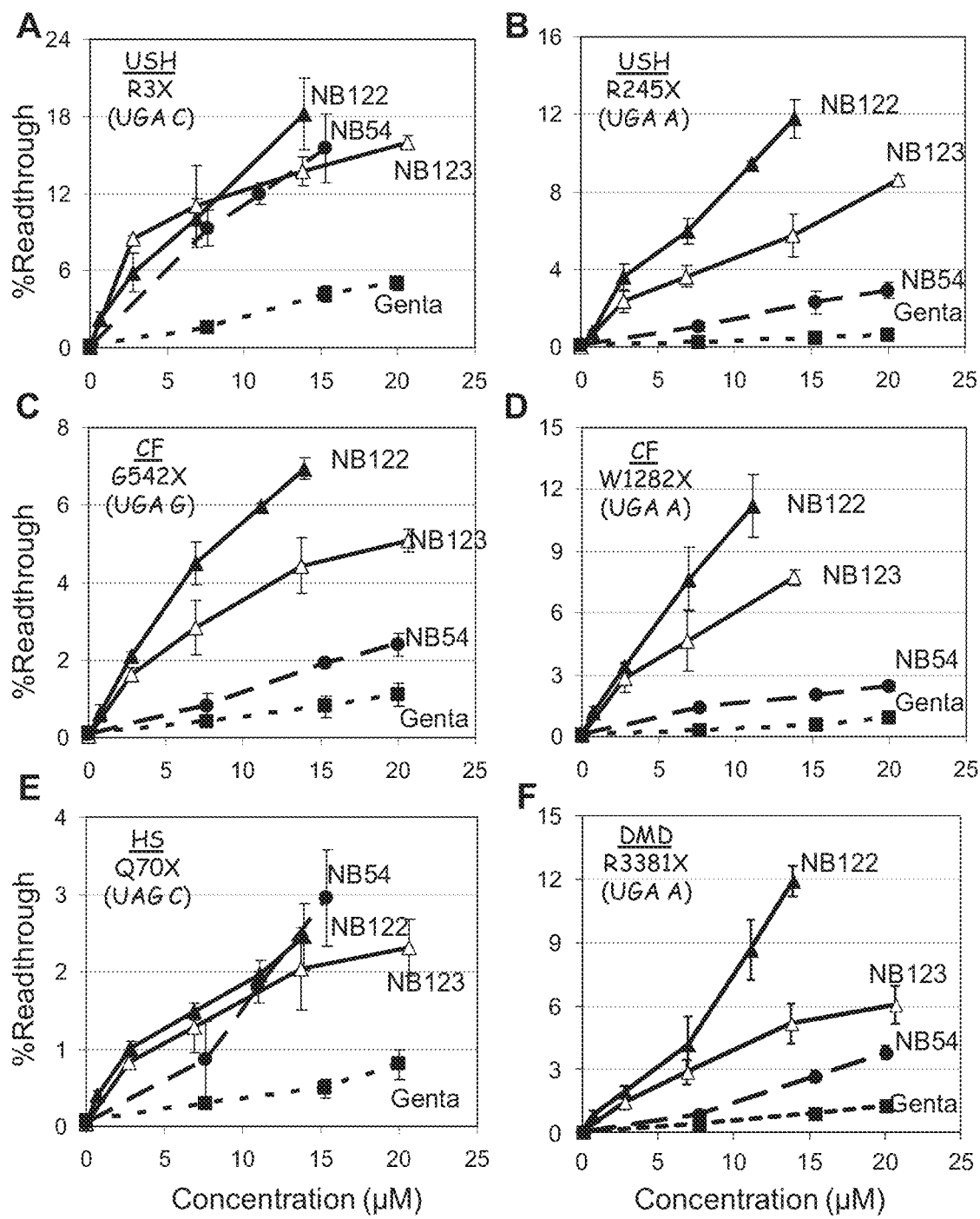
Figure 4:
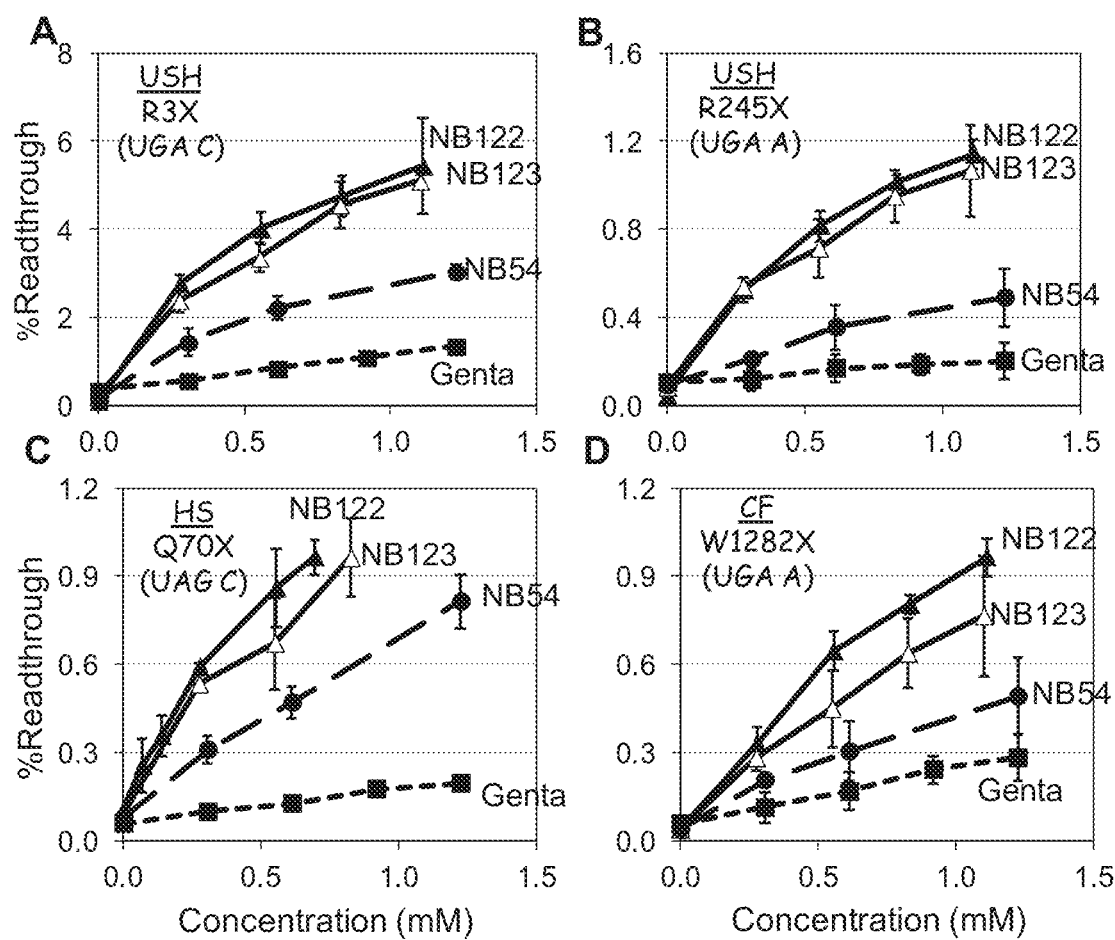
Figure 5:
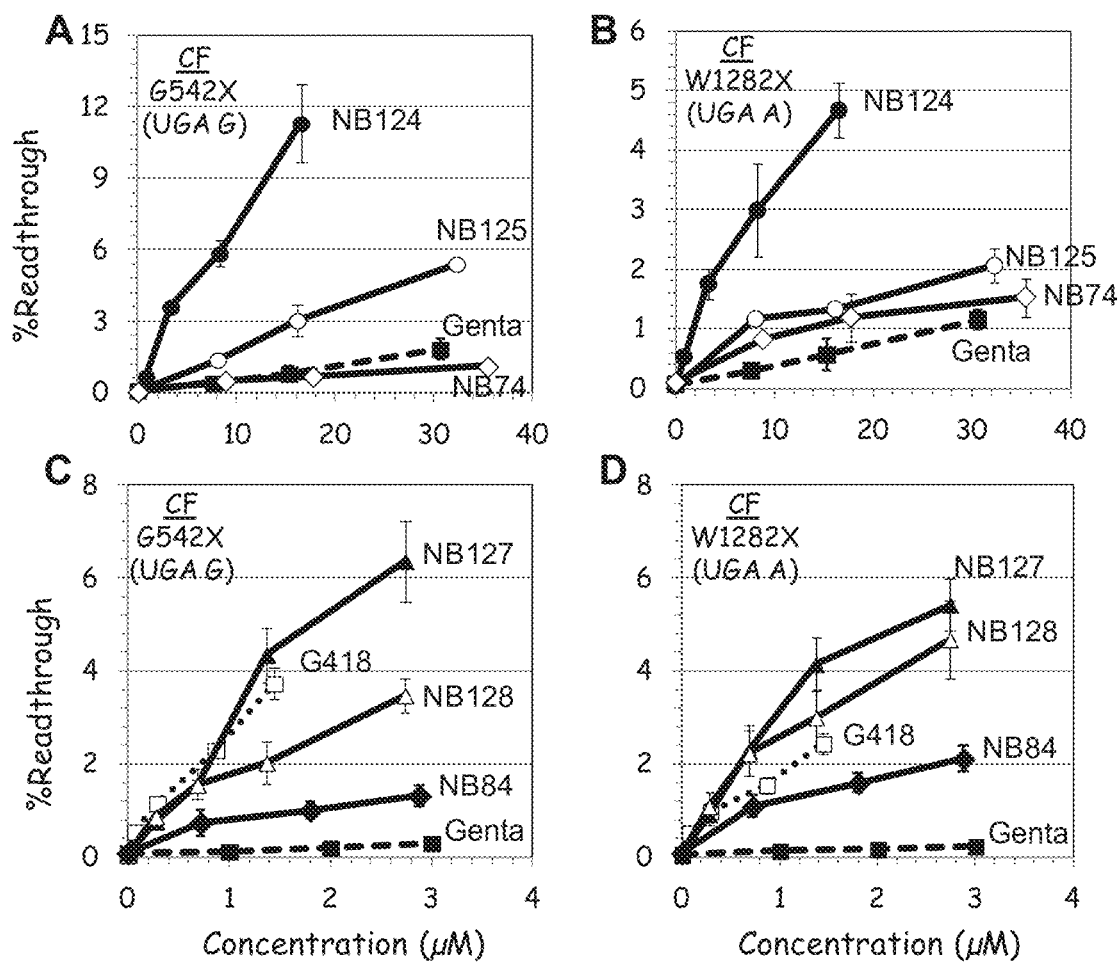

Comparison of the observed cell toxicity data in Table 1 with the readthrough activity data in FIGS. 2-4, demonstrates that the installation of (S)-5"-methyl group either on NB30 to give NB118, or on NB54 to give NB122, does not significantly affect the cytotoxicity (LC$_{50}$ values of 21.4 and 23.5 mM for NB30 and NB118 respectively, and 6.1 and 10.1 mM for NB54 and NB122 respectively, respectively in HEK-293), while it greatly increases the observed stop codon suppression activity (NB30<NB118 and NB54<NB122). The similar cell toxicity observed in the case of NB122 and NB54 in HEK-293 and HFF cells (see, Table 1), together with substantially elevated suppression activity of NB122 over that of NB54 both in vitro and ex vivo in cultured cells, indicate that NB122 may represent a more superior choice than NB54 in suppression therapy.

That the comparative ex-vivo suppression data in FIG. 4 shows only a small preference of NB122 over that of NB123, while the cell toxicity data in Table 1 indicate small (HEK-293 cells) to significantly (HFF cells) better cell toxicity profile of NB123 over that of NB122. Therefore, one may argue that in vivo performance of NB123 diastereomer might be even better than that of NB122. In addition, very recent study on gentamicin demonstrated that the inversion of an absolute configuration at a single carbon atom, from (S)-6'-gentamicin C$_2$ to (R)-6'-gentamicin C$_2$, significantly reduces cell toxicity and apparent nephrotoxicity of the (R)-diastereomer in comparison to that of (S)-diastereomer, as determined in cell culture and animal studies, while the bactericidal efficacy is not affected.

Based on these observations it is clear that additional toxicity tests, including nephrotoxicity and ototoxicity, the major drawbacks of known aminoglycosides, can resolve this issue satisfactorily and validate the observed benefit of either NB122 or NB123, over that of NB54 and over that of gentamicin.

The impact of (S)-5"-methyl group on the elevated readthrough activities of NB118 and NB122 is further supported by the observed eukaryotic translation inhibition data (see, Table 1). The efficacy with which NB122 (half-maximal inhibitory concentration value IC$_{50}$ =5.2 μM) inhibits eukaryotic translation is greater than that of NB118 (IC$_{50}$ =16.0 μM) and NB54 (IC$_{50}$ =24.0 μM), a similar trend to that observed for readthrough activity, namely NB122>NB118>NB54 (see, FIGS. 2-4). In addition, the comparison of IC$_{50}$ values of NB118 and NB122 to those of their parent structures NB30 and NB54 (IC$_{50}$ values of 31 and 24 μM, respectively), reveals that NB118 and NB122 are 1.9-fold and 4.6-fold more specific to the eukaryotic ribosome than their parents NB30 and NB54, indicating that the observed impact of (S)-5"-methyl group on the elevated readthrough activities of NB118 and NB122 is associated with their increased specificity to the eukaryotic ribosome.

Table 2 presents comparative results of cell toxicity, eukaryotic and prokaryotic translation inhibition, and antibacterial activity assays obtain for gentamicin, G418, the previously reported NB74 and NB84, and the exemplary compounds NB124, NB125, NB127 and NB128.

TABLE 2

| Antibacterial activity MIC (μM) | | Translation Inhibition | | Cell toxicity LC$_{50}$ (mM) | | |
|---|---|---|---|---|---|---|
| | | Prokaryotic system | Eukaryotic System | | | |
| B. subtilis ATCC6633 | E. coli R477/100 | IC$_{50}$ (μM) | IC$_{50}$ (μM) | HFF | HEK-293 | Aminoglycoside |
| <0.75 | 6 | 0.028 ± 0.004 | 62 ± 9 | 3.21 ± 0.31 | 2.65 ± 0.54 | Gentamicin |
| <1.25 | 9 | 0.009 ± 0.002 | 2 ± 0.3 | 1.59 ± 0.14 | 1.31 ± 0.06 | G418 |
| 42 | 680 | 1.130 ± 0.120 | 17 ± 0.6 | 21.34 ± 1.72 | 22.17 ± 1.06 | NB74 |
| 70 | 556 | 0.980 ± 0.070 | 2.8 ± 0.3 | 16.33 ± 0.47 | 5.77 ± 0.68 | NB84 |
| 96 | 768 | 1.102 ± 0.185 | 1.49 ± 0.08 | 4.75 ± 0.33 | 5.40 ± 0.45 | NB124 |
| 96 | 1536 | 1.862 ± 0.173 | 7.96 ± 0.27 | 7.59 ± 0.18 | 16.54 ± 3.10 | NB125 |
| 192 | 384 | 1.753 ± 0.274 | 0.73 ± 0.07 | 6.48 ± 0.26 | 5.09 ± 0.27 | NB127 |
| 96 | 384 | 1.752 ± 0.145 | 0.89 ± 0.07 | 2.78 ± 0.11 | 5.35 ± 0.31 | NB128 |

As can be seen in Table 2, comparison of the observed cell toxicity data in Table 2 with the readthrough activity data presented in FIGS. 8-10, demonstrates that compounds according to some embodiments of the present invention, such as NB124, NB125, NB127 and NB128 exhibit approximately the same level of cell toxicity in comparison to previously disclosed compounds, with the exception of NB128 cytotoxicity in human foreskin fibroblast (HFF).

In addition, similar to previously disclosed compounds, the novel NB124, NB125, NB127 and NB128 compounds do not exhibit significant antibacterial activity both in *E. coli* and *B. subtilis* (see, Table 2 above). These data are further supported by their drastically reduced inhibition of prokaryotic protein synthesis (Table 2) in comparison to standard aminoglycoside antibiotics and thus are in accordance to a general trend that aminoglycosides with reduced inhibition of prokaryotic translation are also less cytotoxic probably due to reduced inhibition of mitochondrial protein synthesis.

Example 4

Antibacterial Activity

Results of antimicrobial activity assays obtained for some exemplary compounds according to embodiments of the present invention are presented in Tables 1 and 2 hereinabove.

It has been shown previously that compounds such as NB30, NB54, NB74 and NB84 are about 10-fold weaker inhibitors of prokaryotic translation than gentamicin and paromomycin, and further exhibit almost no bactericidal activity against both Gram-negative and Gram-positive bacteria. The present experiments determine whether compounds according to some embodiments of the present invention, such as NB118, NB119, NB122, NB123, NB124, NB125, NB127 and NB128, retain similar properties.

Hence, exemplary compounds NB118, NB119, NB122, NB123, NB124, NB125, NB127 and NB128 were investigated as antibacterial agents against both Gram-negative (*Escherichia coli*) and Gram-positive (*Bacillus subtilis*) bacteria, together with their prokaryotic anti-translational activities (see, Table 1 and Table 2).

As can be seen in Table 1 and Table 2, the measured $IC_{50}$ values show that the efficacy with which exemplary compounds according to some embodiments of the present invention, inhibit the prokaryotic ribosome is significantly lower than that of paromomycin and gentamicin, in accordance with the observed antibacterial data of this set of compounds; while gentamicin and paromomycin exhibit significant antibacterial activities against both *E. coli* and *B. subtilis*, exemplary compounds according to some embodiments of the present invention lack considerable antibacterial activity.

The observed data with NB118, NB119, NB122, NB123, NB124, NB125, NB127 and NB128 is similar to that observed for NB30, NB54, NB74 and NB84 and further support the previously reported correlation in aminoglycosides between prokaryotic anti-translational activity and MIC values, namely, decreased inhibition of prokaryotic translation is associated with the decrease in antibacterial activity.

Furthermore, the observed continued inability of NB30, NB54, NB74 and NB84, as well as of NB118, NB119, NB122, NB123, NB124, NB125, NB127 and NB128, to show significant antibacterial activity in conjunction with their decreased prokaryotic ribosome specificity, suggest that by reducing the specificity to prokaryotic ribosome, and thereby taking away their antibacterial activity, their action on eukaryotic mitochondrial protein synthesis machinery may be reduced, and thereby significantly reduce their toxic effects on humans. This view is supported by the fact that the mammalian mitochondrial protein synthesis machinery is very similar to the prokaryotic machinery and that the aminoglycoside-induced toxicity may, at least in part, be connected to drug-mediated dysfunction of the mitochondrial ribosome.

The observed significantly increased eukaryotic anti-translational activity (that actually measures only the inhibition of cytoplasmic protein synthesis and not that of mitochondrial protein synthesis) together with the significantly reduced cytotoxicity of compounds NB118, NB119, NB122, NB123, NB124, NB125, NB127 and NB128 (in comparison to those of gentamicin and paromomycin) further support this opinion.

Example 5

Eukaryotic Vs. Prokaryotic Selectivity

As discussed hereinabove, in order to constitute a worthy drug candidate which can be used to treat genetic diseases caused by premature stop codon mutations, an aminoglycoside should be non-toxic and interact with eukaryotic cytoplasmic ribosomes. The virtue of non-toxicity can be verified by lack of antimicrobial activity, meaning that the drug will inhibit prokaryotic translation to a lesser extent and therefore it most likely will not inhibit mitochondrial translation. The presence of this beneficial combination of desired qualities in an aminoglycoside such as the compounds presented herein can be demonstrated by a eukaryotic versus prokaryotic selective activity.

It can also be said that a notable selectivity of an aminoglycoside compound towards inhibiting translation in eukaryote over inhibiting translation in prokaryote can be used to predict its effectiveness and safety as a drug candidate for treating genetic disorders associated with premature stop codon mutations.

Table 3 consolidates and compares the results obtained for a series of exemplary known aminoglycosides and exemplary presently disclosed aminoglycosides in translation inhibition assays conducted with eukaryotic and prokaryotic ribosomal systems. Each compound is also noted by the type of pharmacophores point that the compound exhibits out of the five pharmacophores points presented in Scheme 1 hereinabove. In Table 3, the pharmacophore points are denoted "i" for the hydroxyl group in position 6'; "ii" for the AHB group in position N1; "iii" for the third saccharide moiety "Ring III"; "iv" for a methyl at position 6'; and "v" for the methyl at position 5".

TABLE 3

| \ | Pharmacophore points | | | | | Translation Inhibition | | Prokaryotic versus Eukaryotic selectivity |
|---|---|---|---|---|---|---|---|---|
| i | ii | iii | iv | v | Aminoglycoside | $IC_{50}^{Euk}$ (µM) | $IC_{50}^{Pro}$ (µM) | $IC_{50}^{Euk}/IC_{50}^{Pro}$ |
|  |  | X | X |  | Gentamicin | 62 ± 9 | 0.028 ± 0.004 | 2,214 |
| X |  | X |  |  | Paromomycin | 57 ± 4 | 0.051 ± 0.005 | 1,118 |
| X |  | X | X |  | G418 | 2.0 ± 0.3 | 0.009 ± 0.002 | 225 |
| X |  | X |  |  | NB30 | 31 ± 4 | 0.46 ± 0.05 | 68 |
| X | X | X |  |  | NB54 | 24 ± 1 | 0.16 ± 0.02 | 151 |
| X |  | X | X |  | NB74 | 17 ± 0.6 | 1.130 ± 0.120 | 15 |
| X | X | X | X |  | NB84 | 2.8 ± 0.3 | 0.980 ± 0.070 | 2.9 |
| X |  | X |  | X | NB118 | 15.5 ± 1.3 | 1.960 ± 0.206 | 7.9 |
| X |  | X |  | X | NB119 | 28 ± 1.1 | 2.132 ± 0.478 | 13 |
| X | X | X |  | X | NB122 | 5.2 ± 0.7 | 2.266 ± 0.196 | 2.3 |
| X | X | X |  | X | NB123 | 4.6 ± 0.6 | 0.811 ± 0.059 | 5.7 |
| X |  | X | X | X | NB124 | 1.49 ± 0.08 | 1.102 ± 0.185 | 1.3 |
| X |  | X | X | X | NB125 | 7.96 ± 0.27 | 1.862 ± 0.173 | 4.3 |
| X | X | X | X | X | NB127 | 0.73 ± 0.07 | 1.753 ± 0.274 | 0.4 |
| X | X | X | X | X | NB128 | 0.89 ± 0.07 | 1.752 ± 0.145 | 0.5 |

In all biological experiments conducted, all tested aminoglycosides were in their sulfate salt forms. The concentrations reported in Table 3 refer to that of the free amine form of each aminoglycoside. Prokaryotic and eukaryotic translation inhibition was quantified in coupled transcription/translation assays as previously described. The half-maximal concentration ($IC_{50}$) values were obtained from fitting concentration response curves to the data of at least three independent experiments, using GraFit 5 software. All the experiments were performed in duplicates and analogous results were obtained in three different experiments.

As can be seen in Table 3, a notable decrease in the $IC_{50}^{Euk}/IC_{50}^{Pro}$ ratio (inhibition of translation in eukaryotes to inhibition of translation in prokaryotes) is observed, going down from an average value of about 115 (average of the ratio of NB30, NB54, NB74 and NB84), to an average value of about 7 (average of the ratio of NB118, NB119, NB122 and NB123) for adding the presently disclosed pharmacophore point "v", to an average value of about 1.6 (average of the ratio of NB124, NB125, NB127 and NB128) for adding the presently disclosed pharmacophore point "v" and the previously disclosed pharmacophore point "iv".

It can clearly be seen in Table 3, that the exemplary aminoglycoside compounds, according to some embodiments of the present invention, which exhibit all five pharmacophores points, regardless of the stereo-configuration at the 5" position, also exhibit the highest eukaryotic versus prokaryotic selectivity, namely these compounds are ranking high in the list of possible drug candidates for treating genetic disorders in humans.

Indeed, while preparing and testing exemplary compounds NB124, NB125, NB127 and NB128, it has been found that the increased inhibition of prokaryotic cytoplasmic protein synthesis is associated with increased readthrough activity. The data in Table 3 shows that the systematic development of a comprehensive pharmacophore could gradually increase the specificity of the newly developed compounds to the cytoplasmic ribosome and decrease their specificity to the prokaryotic ribosome, until NB127 and NB128 wherein all five pharmacophore points are implemented, exhibit reversed selectivity to eukaryotic versus prokaryotic translation systems (ribosome).

Two observations are noted herein:

1) while the standard aminoglycoside antibiotics like gentamicin and paromomycin are 2,214-fold and 1,118-fold more selective to prokaryotic versus eukaryotic ribosome, this selectivity in G418 drops to only 225-fold especially because its comparatively increased inhibition of eukaryotic translation. This strong inhibition ($IC_{50}^{Euk}$=2 µM) of eukaryotic translation was considered as a main reason of the drastically high cytotoxicity of G418 as well as main reason for its very strong readthrough activity. The results presented in Table 3 suggest that while the elevated inhibition of eukaryotic translation is indeed supports to its strong readthrough activity, the inhibition of eukaryotic translation is not the only toxic event of G418 but that the other effect(s) of G418 on eukaryotic cells are correlated to its toxicity.

According to the data presented in Table 3, several compounds according to some embodiments of the present invention, exhibit similar or greater inhibition potency of eukaryotic translation, including NB124, NB127 and NB128, while being significantly less cytotoxic than G418.

2) plotting the $IC_{50}^{Euk}$ values against the in vitro readthrough activity of all the standard and synthetic aminoglycosides tested, close correlation between these two parameters has been observed, namely, increased inhibition is associated with increased readthrough activity, as illustrated in FIG. 13A-B).

FIGS. 13A-B present scatter plots for identifying possible correlation between readthrough activity and protein translation inhibition in vitro in eukaryotic systems as observed for a series of known compounds and exemplary compounds according to some embodiments of the present invention, wherein increasing inhibition of protein synthesis (lower $IC_{50}$ values) is associated with the increase of readthrough activity, whereas FIG. 13A is a semilogarithmic plot of eukaryotic inhibition of translation versus in vitro readthrough activity at 1.4 µM concentration of the tested aminoglycosides (shown on the X-axis) using six different nonsense mutations (W1282X, Q70X, R3X, R245X, G542X and R3381X) and FIG. 1B is a linear plot of the same data presented in FIG. 13A.

Figure 13:
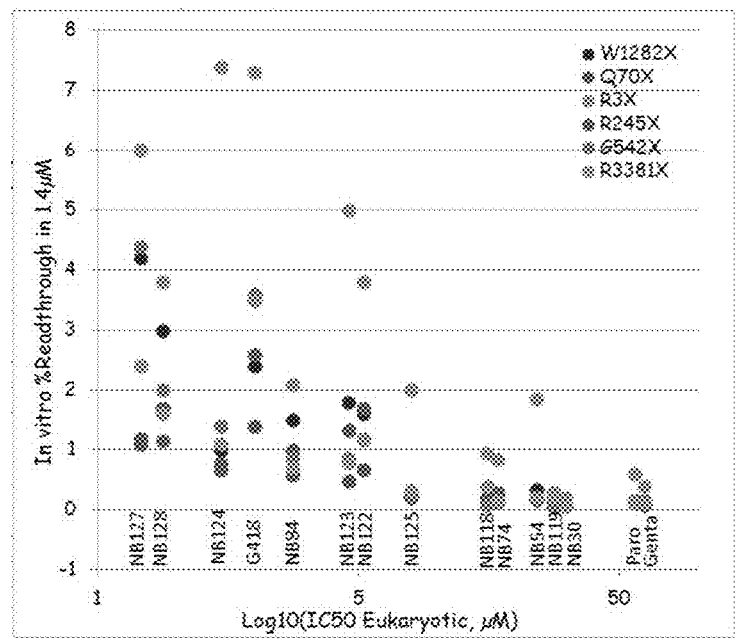
Figure 13:
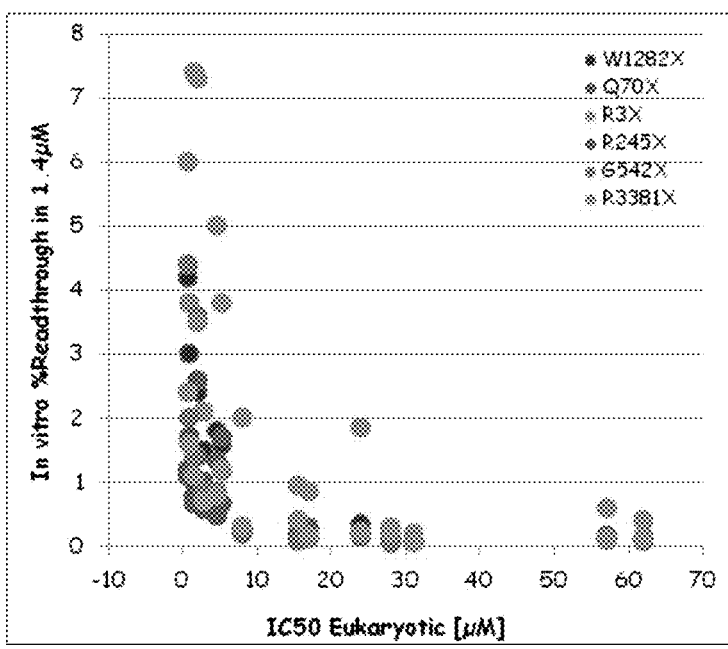

It is noted that since the readthrough activity is dose dependent and is also affected by various factors including the identity of stop codon, fourth base in the downstream sequence from the stop and the sequence contest around the stop codon, the data presented in FIG. 13 was collected while using one concentration (1.4 μM) in which all the compounds were tested and series of different constructs that represent 6 different constructs of 4 different disease models. Thus, increasing specificity and selectivity to the prokaryotic ribosome leads to subsequent increase in desired biological activity of the compound and with reduced toxicity.

Another observation made by the present inventors involves a previously reported compound, NB33, which is essentially a dimer of paromamine in which two paromamine moieties are connected at 3'-oxygens via methylene bridge. NB33 is highly specific to eukaryotic ribosome and inhibits protein synthesis by $IC_{50}^{Euk}$ value of 1.1 mM, almost twice as much as G418 ($IC_{50}^{Euk}$ of 2.0 mM). However, NB33 has almost no readthrough activity, indicating that its mechanism of inhibition is different to that of known aminoglycosides and the compounds according to some embodiments of the present invention, that exhibit readthrough activity. Thus, it was concluded that merely increasing the inhibition potency of aminoglycoside is not necessarily accompanied with increased readthrough activity. Such a correlation should be considered for those aminoglycoside compounds that inhibit translation process with a same mechanism, namely the fidelity of proof-reading process. Indeed a recent study on the interaction of NB33 with human A-site rRNA oligonucleotide model demonstrated that NB33 binds and stabilizes the A-site in a non-decoding conformation and as such blocks the ribosome translocation step.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having the general formula I:

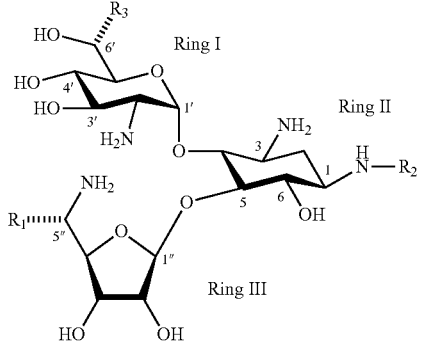

Formula I or a pharmaceutically acceptable salt thereof, wherein:

R1 is selected from the group consisting of alkyl, cycloalkyl and aryl;

R2 is hydrogen or (S)-4-amino-2-hydroxybutyryl (AHB);

R3 is selected from the group consisting of hydrogen, alkyl, cycloalkyl and aryl; and a stereo-configuration of each of position 6' and position 5" is independently an R configuration or an S configuration.

2. The compound of claim 1, wherein R1 is alkyl.

3. The compound of claim 2, wherein said alkyl is methyl.

4. The compound of claim 1, wherein R2 and R3 are each hydrogen.

5. The compound of claim 1, wherein R2 is AHB and R3 is hydrogen.

6. The compound of claim 1, wherein R2 is hydrogen and R3 is alkyl.

7. The compound of claim 6, wherein said alkyl is methyl.

8. The compound of claim 1, wherein R2 is AHB and R3 is alkyl.

9. The compound of claim 8, wherein said alkyl is methyl.

10. The compound of claim 1, being selected from the group consisting of:

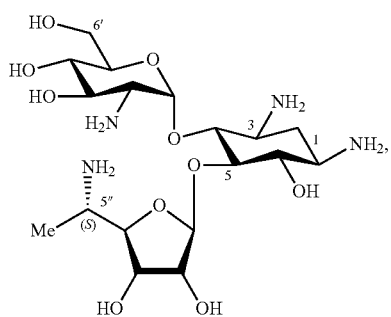

NB118

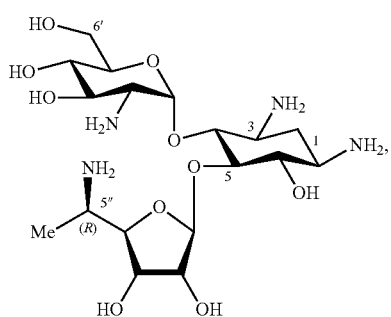

NB119

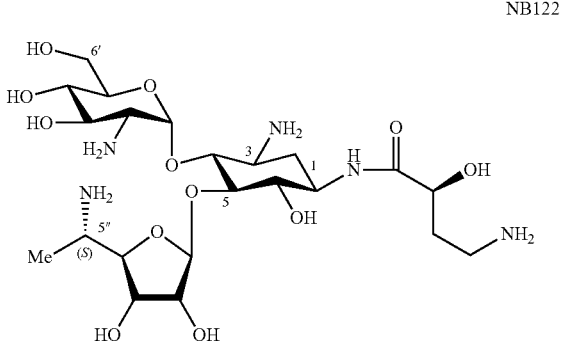

NB122

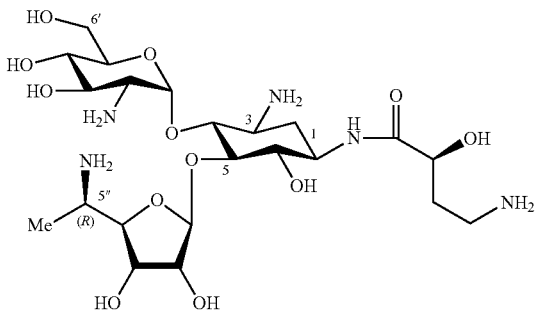

NB123

-continued

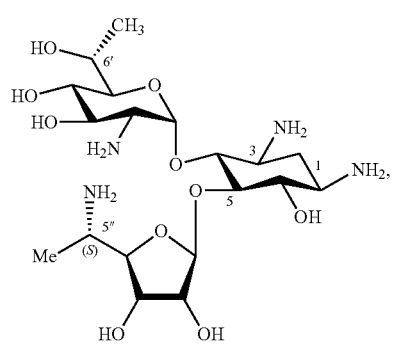
NB124

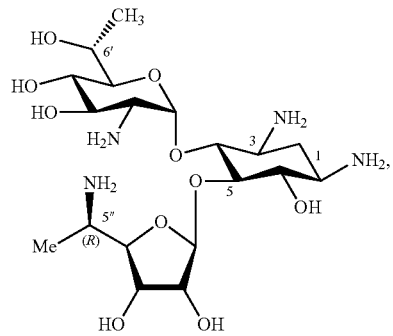
NB125

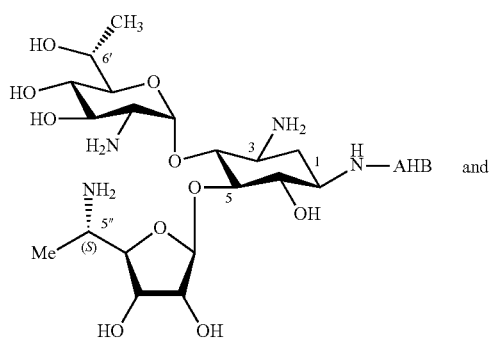
NB127

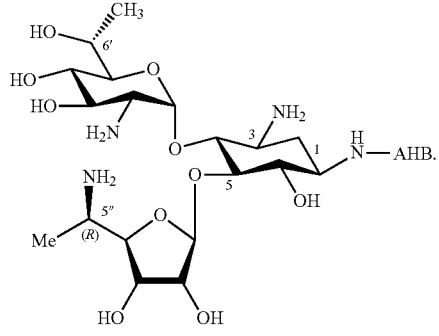
NB128

11. The compound of claim 1, characterized by a ratio of IC50 translation inhibition in eukaryotes to IC50 translation inhibition in prokaryotes lower than 15.

12. The compound of claim 11, wherein said ratio is lower than 1.

13. The compound of claim 1, characterized by a MIC in Gram-negative bacteria higher than 200 µM and a MIC in Gram-positive bacteria higher than 20 µM.

14. A pharmaceutical composition comprising the compound of claim 1 and a pharmaceutically acceptable carrier.

15. The pharmaceutical composition of claim 14, being packaged in a packaging material and identified in print, in or on said packaging material, for use in the treatment of a genetic disorder associated with a premature stop codon mutation and/or a protein truncation phenotype, said genetic disorder being selected from the group consisting of cystic fibrosis (CE), Duchenne muscular dystrophy (DMD), ataxia-telangiectasia, Hurler syndrome, hemophilia A, hemophilia B, Usher syndrome and Tay-Sachs.

16. The pharmaceutical composition of claim 14, wherein R1 is alkyl.

17. The pharmaceutical composition of claim 16, wherein said alkyl is methyl.

18. The pharmaceutical composition of claim 14, wherein R2 and R3 are each hydrogen.

19. The pharmaceutical composition of claim 14, wherein R2 is AHB and R3 is hydrogen.

20. The pharmaceutical composition of claim 14, wherein R2 is hydrogen and R3 is alkyl.

21. The pharmaceutical composition of claim 14, wherein R2 is AHB and R3 is alkyl.

22. The pharmaceutical composition of claim 15, wherein said genetic disorder is cystic fibrosis.

23. A method for treating a genetic disorder associated with a premature stop codon mutation and/or a protein truncation phenotype, the method comprising administering to a subject in need thereof a therapeutically effective amount of the compound of claim 1, wherein said genetic disorder being selected from the group consisting of cystic fibrosis (CF), Duchenne muscular dystrophy (DMD), ataxia-telangiectasia, Hurler syndrome, hemophilia A, hemophilia B, Usher syndrome and Tay-Sachs.

24. The method of claim 23, wherein said genetic disorder is cystic fibrosis.

25. The method of claim 23, wherein R1 is alkyl.

26. The method of claim 25, wherein said alkyl is methyl.

27. The method of claim 23, wherein R2 and R3 are each hydrogen.

28. The method of claim 23, wherein R2 is AHB and R3 is hydrogen.

29. The method of claim 23, wherein R2 is hydrogen and R3 is alkyl.

30. The method of claim 23, wherein R2 is AHB and R3 is alkyl.

31. A process of preparing the compound of claim 1, the process comprising:
(a) providing a donor compound having the general Formula II:

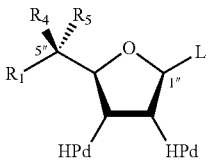

Formula II wherein:
R1 is selected from the group consisting of alkyl, cycloalkyl and aryl;
R4 is hydrogen or a donor amino-protecting group;
R5 is a donor amino-protecting group if R4 is hydrogen or hydrogen if R4 is a donor amino-protecting group;
each of HPd is a donor hydroxyl-protecting group; and
L is a leaving group;

(b) coupling said donor compound with an acceptor compound having the general formula III

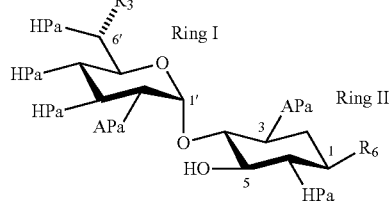

Formula III wherein:
the dashed line indicates an R configuration or an S configuration;
R3 is selected from the group consisting of hydrogen, alkyl, cycloalkyl and aryl;
R6 is an acceptor amino-protecting group or (S)-4-azido-2-O-acetyl-1-butyryl;
HPa is an acceptor hydroxyl-protecting group; and
APa is an acceptor amino-protecting group; and
(c) removing each of said amino-protecting group and said hydroxyl-protecting group, thereby obtaining the compound.

32. The process of claim 31, wherein said leaving group is trichloroacetimidate.

33. The process of claim 31, wherein said donor hydroxyl-protecting group is O-benzoyl and said donor amino-protecting group is azido.

34. The process of claim 31, wherein said acceptor hydroxyl-protecting group is O-acetyl and said acceptor amino-protecting group is azido.

35. The compound of claim 1, being:

NB118

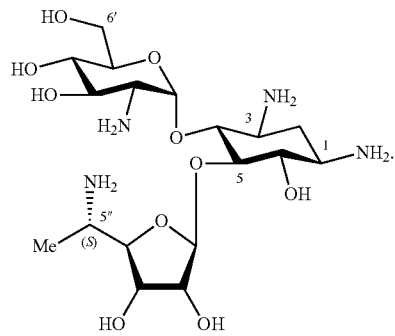

36. The compound of claim 1, being:

NB119

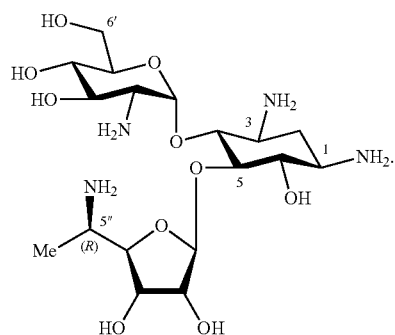

37. The compound of claim 1, being:

NB122

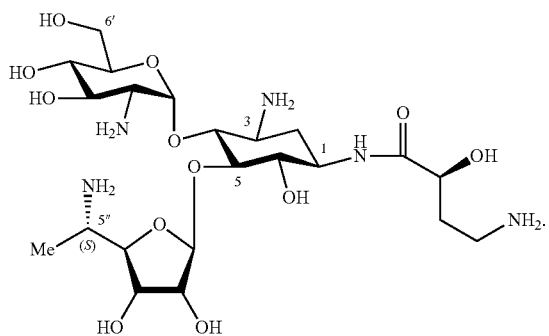

38. The compound of claim 1, being:

NB123

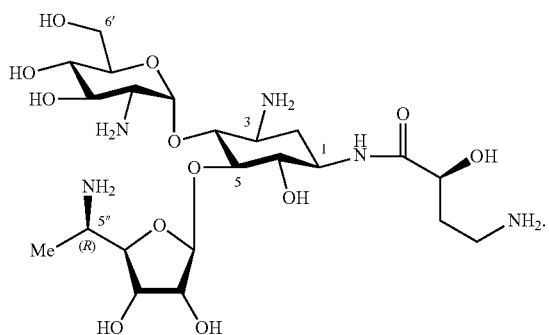

39. The compound of claim 1, being:

NB124

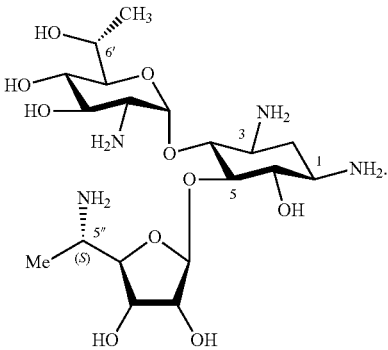

40. The compound of claim 1, being:

NB125

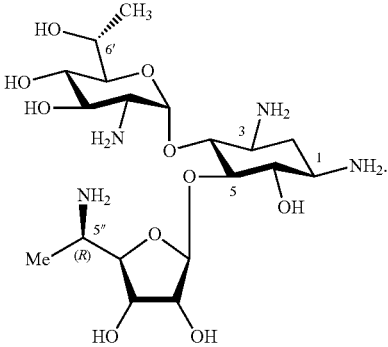

41. The compound of claim 1, being:
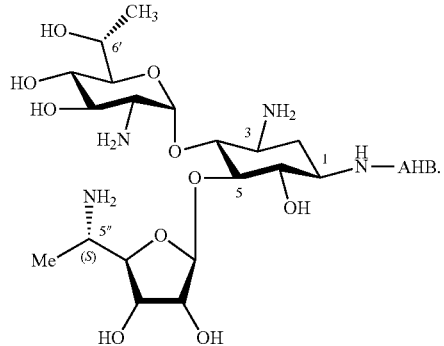
NB127
42. The compound of claim 1, being:
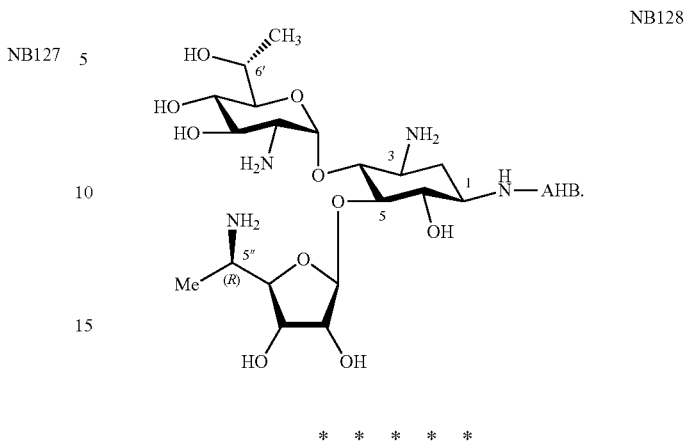
NB128
* * * * *

UNITED STATES PATENT AND TRADEMARK OFFICE
CERTIFICATE OF CORRECTION

Page 1 of 1

PATENT NO. : 8,895,519 B2
APPLICATION NO. : 13/885715
DATED : November 25, 2014
INVENTOR(S) : Baasov et al.

It is certified that error appears in the above-identified patent and that said Letters Patent is hereby corrected as shown below:

In the Specification:

Column 1, line 15, insert

--STATEMENT REGARDING FEDERALLY SPONSORED RESEARCH OR DEVELOPMENT

This invention was made with government support under Contract No. GM094792 awarded by the NIH. The government has certain rights in the invention.--

Signed and Sealed this
Twenty-third Day of February, 2016

Michelle K. Lee
*Director of the United States Patent and Trademark Office*

SEQUENCE LISTING

```
<160> NUMBER OF SEQ ID NOS: 24

<210> SEQ ID NO 1
<211> LENGTH: 43
<212> TYPE: DNA
<213> ORGANISM: Artificial Sequence
<220> FEATURE:
<223> OTHER INFORMATION: Single  strand DNA oligonucleotide

<400> SEQUENCE: 1
gatcccagaa gatgtttcga cagttttatc tctggacaga gct                    43

<210> SEQ ID NO 2
<211> LENGTH: 33
<212> TYPE: DNA
<213> ORGANISM: Artificial Sequence
<220> FEATURE:
<223> OTHER INFORMATION: Single  strand DNA oligonucleotide

<400> SEQUENCE: 2
ctgtcagaga taaaactgtc gaaacatctt ctg                               33

<210> SEQ ID NO 3
<211> LENGTH: 43
<212> TYPE: DNA
<213> ORGANISM: Artificial Sequence
<220> FEATURE:
<223> OTHER INFORMATION: Single  strand DNA oligonucleotide

<400> SEQUENCE: 3
gatcccagaa gatgttttga cagttttatc tctggacaga gct                    43

<210> SEQ ID NO 4
<211> LENGTH: 33
<212> TYPE: DNA
<213> ORGANISM: Artificial Sequence
<220> FEATURE:
<223> OTHER INFORMATION: Single  strand DNA oligonucleotide

<400> SEQUENCE: 4
ctgtcagaga taaaactgtc aaaacatctt ctg                               33
```

<210> SEQ ID NO 5
<211> LENGTH: 48
<212> TYPE: DNA
<213> ORGANISM: Artificial Sequence
<220> FEATURE:
<223> OTHER INFORMATION: Single strand DNA oligonucleotide

<400> SEQUENCE: 5
gatccaaaat ctgaatgaga ggcgaaccac caccaccacc ctcgagct                48

<210> SEQ ID NO 6
<211> LENGTH: 40
<212> TYPE: DNA
<213> ORGANISM: Artificial Sequence
<220> FEATURE:
<223> OTHER INFORMATION: Single strand DNA oligonucleotide

<400> SEQUENCE: 6
cgagggtggt ggtggttgtt cgcctctcat tcagattttg                         40

<210> SEQ ID NO 7
<211> LENGTH: 48
<212> TYPE: DNA
<213> ORGANISM: Artificial Sequence
<220> FEATURE:
<223> OTHER INFORMATION: Single strand DNA oligonucleotide

<400> SEQUENCE: 7
gatccaaaat ctgaatgaga ggtgaaccac caccaccacc ctcgagct                48

<210> SEQ ID NO 8
<211> LENGTH: 40
<212> TYPE: DNA
<213> ORGANISM: Artificial Sequence
<220> FEATURE:
<223> OTHER INFORMATION: Single strand DNA oligonucleotide

<400> SEQUENCE: 8
cgagggtggt ggtggttgtt cacctctcat tcagattttg                         40

<210> SEQ ID NO 9
<211> LENGTH: 38
<212> TYPE: DNA
<213> ORGANISM: Artificial Sequence
<220> FEATURE:
<223> OTHER INFORMATION: Single strand DNA oligonucleotide

<400> SEQUENCE: 9
tcgaccaata tagttcttgg agaaggtgga atcgagct                           38

<210> SEQ ID NO 10
<211> LENGTH: 30
<212> TYPE: DNA
<213> ORGANISM: Artificial Sequence
<220> FEATURE:
<223> OTHER INFORMATION: Single strand DNA oligonucleotide

<400> SEQUENCE: 10
cgattccacc ttctcgaaga actatattgg                                    30

<210> SEQ ID NO 11
<211> LENGTH: 38
<212> TYPE: DNA
<213> ORGANISM: Artificial Sequence
<220> FEATURE:
<223> OTHER INFORMATION: Single strand DNA oligonucleotide

```
<400> SEQUENCE: 11
tcgaccaata tagttctttg agaaggtgga atcgagct                            38

<210> SEQ ID NO 12
<211> LENGTH: 30
<212> TYPE: DNA
<213> ORGANISM: Artificial Sequence
<220> FEATURE:
<223> OTHER INFORMATION: Single  strand DNA oligonucleotide

<400> SEQUENCE: 12
cgattccacc ttctcaaaga actatattgg                                     30

<210> SEQ ID NO 13
<211> LENGTH: 38
<212> TYPE: DNA
<213> ORGANISM: Artificial Sequence
<220> FEATURE:
<223> OTHER INFORMATION: Single  strand DNA oligonucleotide

<400> SEQUENCE: 13
tcgacaactt tgcaacagtg gaggaaagcc tttgagct                            38

<210> SEQ ID NO 14
<211> LENGTH: 30
<212> TYPE: DNA
<213> ORGANISM: Artificial Sequence
<220> FEATURE:
<223> OTHER INFORMATION: Single  strand DNA oligonucleotide

<400> SEQUENCE: 14
caaaggcttt cctccactgt tgcaaagttg                                     30

<210> SEQ ID NO 15
<211> LENGTH: 38
<212> TYPE: DNA
<213> ORGANISM: Artificial Sequence
<220> FEATURE:
<223> OTHER INFORMATION: Single  strand DNA oligonucleotide

<400> SEQUENCE: 15
tcgacaactt tgcaacagtg aaggaaagcc tttgagct                            38

<210> SEQ ID NO 16
<211> LENGTH: 30
<212> TYPE: DNA
<213> ORGANISM: Artificial Sequence
<220> FEATURE:
<223> OTHER INFORMATION: Single  strand DNA oligonucleotide

<400> SEQUENCE: 16
caaaggcttt ccttcactgt tgcaaagttg                                     30

<210> SEQ ID NO 17
<211> LENGTH: 38
<212> TYPE: DNA
<213> ORGANISM: Artificial Sequence
<220> FEATURE:
<223> OTHER INFORMATION: Single  strand DNA oligonucleotide

<400> SEQUENCE: 17
tcgacaaaaa acaaattttg caccaaaagg tatgagct                            38

<210> SEQ ID NO 18
```

```
<211> LENGTH: 30
<212> TYPE: DNA
<213> ORGANISM: Artificial Sequence
<220> FEATURE:
<223> OTHER INFORMATION: Single strand DNA oligonucleotide

<400> SEQUENCE: 18 cataccttt ggtgcaaaat ttgttttttg                                30

<210> SEQ ID NO 19
<211> LENGTH: 38
<212> TYPE: DNA
<213> ORGANISM: Artificial Sequence
<220> FEATURE:
<223> OTHER INFORMATION: Single strand DNA oligonucleotide

<400> SEQUENCE: 19
tcgacaaaaa acaaattttg aaccaaaagg tatgagct                      38

<210> SEQ ID NO 20
<211> LENGTH: 30
<212> TYPE: DNA
<213> ORGANISM: Artificial Sequence
<220> FEATURE:
<223> OTHER INFORMATION: Single strand DNA oligonucleotide

<400> SEQUENCE: 20 cataccttt ggttcaaaat ttgttttttg                                30

<210> SEQ ID NO 21
<211> LENGTH: 38
<212> TYPE: DNA
<213> ORGANISM: Artificial Sequence
<220> FEATURE:
<223> OTHER INFORMATION: Single strand DNA oligonucleotide

<400> SEQUENCE: 21
tcgaccctca gctgggacca gcagctcaac ctcgagct                      38

<210> SEQ ID NO 22
<211> LENGTH: 29
<212> TYPE: DNA
<213> ORGANISM: Artificial Sequence
<220> FEATURE:
<223> OTHER INFORMATION: Single strand DNA oligonucleotide

<400> SEQUENCE: 22
cgaggttgag ctgctggtcc cagctgagg                                29

<210> SEQ ID NO 23
<211> LENGTH: 38
<212> TYPE: DNA
<213> ORGANISM: Artificial Sequence
<220> FEATURE:
<223> OTHER INFORMATION: Single strand DNA oligonucleotide

<400> SEQUENCE: 23
tcgaccctca gctgggacta gcagctcaac ctcgagct                      38

<210> SEQ ID NO 24
<211> LENGTH: 29
<212> TYPE: DNA
<213> ORGANISM: Artificial Sequence
```

```
<220> FEATURE:
<223> OTHER INFORMATION: Single strand DNA oligonucleotide

<400> SEQUENCE: 24
cgaggttgag ctgctagtcc cagctgagg                                        29
```